(12) United States Patent
Irie et al.

(10) Patent No.: US 8,119,812 B2
(45) Date of Patent: Feb. 21, 2012

(54) THIAZOLIDINONE DERIVATIVE

(75) Inventors: Takayuki Irie, Osaka (JP); Masaaki Sawa, Osaka (JP); Sayuri Ito, Tokyo (JP); Chika Tanaka, Tokyo (JP); Seong Gu Ro, Seoul (KR); Choul Hong Park, Seoul (KR)

(73) Assignees: SBI Biotech Co., Ltd. (JP); Crystalgenomics, Inc. (KR)

( * ) Notice: Subject to any disclaimer, the term of this patent is extended or adjusted under 35 U.S.C. 154(b) by 0 days.

(21) Appl. No.: 13/002,147

(22) PCT Filed: Apr. 19, 2010

(86) PCT No.: PCT/JP2010/056930
§ 371 (c)(1),
(2), (4) Date: Apr. 14, 2011

(87) PCT Pub. No.: WO2010/122979
PCT Pub. Date: Oct. 28, 2010

(65) Prior Publication Data
US 2011/0190299 A1    Aug. 4, 2011

(30) Foreign Application Priority Data
Apr. 20, 2009 (JP) ................. 2009-102461

(51) Int. Cl.
*A61K 31/427* (2006.01)
*C07D 417/06* (2006.01)
*C07D 417/14* (2006.01)

(52) U.S. Cl. ............ 548/184; 514/369; 514/254.04; 514/236.8; 514/314; 514/326; 544/133; 544/369; 546/159; 546/209; 548/181

(58) Field of Classification Search .......... 548/184
See application file for complete search history.

(56) References Cited

U.S. PATENT DOCUMENTS
2009/0253679 A1    10/2009    Leroy et al.

FOREIGN PATENT DOCUMENTS

| JP | 2009-508848 A | 3/2009 |
|---|---|---|
| WO | WO-2004/028535 A1 | 4/2004 |
| WO | WO-2004/047760 A2 | 6/2004 |
| WO | WO-2007/032028 A1 | 3/2007 |
| WO | WO-2007/071621 A1 | 6/2007 |
| WO | WO-2007/096334 A1 | 8/2007 |
| WO | WO-2007/110344 A1 | 10/2007 |
| WO | WO-2007/124288 A1 | 11/2007 |
| WO | WO-2008/046982 A2 | 4/2008 |

OTHER PUBLICATIONS

"International Application Serial No. PCT/JP2010/056930, International Search Report mailed May 18, 2010", (w/ English Translation), 4 pgs.

Zhou, H., et al., "Design, Synthesis, Cytoselective Toxicity, Structure-Activity Relationships, and Pharmacophone of Thiazolidinose Derivatives Targeting Drug-Resistant Cancer Cells", *J. Med. Chem.*, 51(5), (2008), 1242-1251.

*Primary Examiner* — Laura L. Stockton
(74) *Attorney, Agent, or Firm* — Schwegman, Lundberg & Woessner, P.A.

(57) ABSTRACT

An object of the present invention is to provide thiazolidinone derivatives. More specifically, an object of the present invention is to provide novel compounds having a CDC7 inhibitory action.

The present invention provides thiazolidinone derivatives represented by the formula (I)

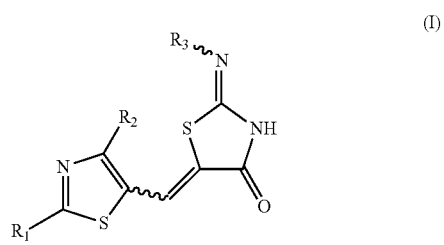

The compounds of the present invention inhibit the CDC7 protein kinase activity, and suppress cell proliferation.

8 Claims, 1 Drawing Sheet

THIAZOLIDINONE DERIVATIVE

RELATED APPLICATIONS

This application is a nationalization under 35 U.S.C. 371 of PCT/JP2010/056930, filed Apr. 19, 2010 and published as WO 2010/122979 A1 on Oct. 28, 2010, which claimed priority under 35 U.S.C. 119 to Japanese Patent Application No. 2009-102461, filed Apr. 20, 2009; which applications and publication are incorporated herein by reference in their entirety.

TECHNICAL FIELD

The present invention relates to thiazolidinone derivatives, geometric isomers and tautomers thereof, as well as salts, hydrates, or solvates thereof.

BACKGROUND ART

In general, the biological effect of proteins is modulated by various mechanisms of post-translational modifications. Specifically, it has been shown that methylation, acetylation, glycosylation, phosphorylation, or the like, is involved in the regulation of functions or structures of proteins. Among these post-translational modifications, phosphorylation is an important mechanism related to modulation of many functions such as intracellular signal transduction, cell cycle, and cell death, or the like. For example, it is thought that more than one-third of the intracellular proteins in mammalian cells are phosphorylated.

Proteins are phosphorylated by the action of protein kinases. In general, a protein kinase catalyzes a reaction of bonding a phosphate group to a specific site of a specific substrate protein. That is to say, proteins are phosphorylated on specific amino acid residues. Thus, protein kinases can be classified as follows based on amino acids at a site to be phosphorylated.

Serine/threonine kinase (Ser/S or Thr/T residue is phosphorylated)

Tyrosine kinase (Tyr/Y is phosphorylated)

Human CDC7 that is one of the serine/threonine kinases is a protein kinase involved in the start of DNA replication during the cell cycle. Specifically, it is thought that with phosphorylation of MCM (Minichromosome maintenance) protein by CDC7, CDC45 and DNA polymerase are recruited to DNA and the DNA replication starts. The phosphorylation action of CDC7 needs a cofactor. For example, ASK is identified as a cofactor that activates the phosphorylation action of CDC7.

It is thought that CDC7 involved in DNA replication can be an important target for cell proliferation diseases such as cancers. In other words, when the DNA replication necessary for the cell proliferation can be controlled by inhibiting CDC7, the cell proliferation may be suppressed. Various compounds, which have an inhibitory action against protein kinase including CDC7, have been reported to date (Patent Documents 1 to 5).

[Prior Art Documents]
[Patent Documents]
[Patent Document 1] WO2007/071621
[Patent Document 2] WO2007/096334
[Patent Document 3] WO2007/110344
[Patent Document 4] WO2007/124288
[Patent Document 5] WO2008/046982

SUMMARY OF THE INVENTION

Problems to be Solved by the Invention

An object of the present invention is to provide novel thiazolidinone derivatives, geometric isomers and tautomers thereof, as well as salts, hydrates, or solvates thereof. Alternatively, the present invention provides thiazolidinone derivatives having a CDC7 protein kinase inhibitory action. Alternatively, the present invention provides thiazolidinone derivatives having an action of cell proliferation suppression.

Means for Solving the Problems

The present invention provides thiazolidinone derivatives represented by the following formula (I), geometric isomers and tautomers thereof, as well as salts, hydrates, or solvates thereof. Furthermore, the present invention provides a production process of thiazolidinone derivatives represented by the following formula (I).

[1] A compound represented by the following formula (I), a geometric isomer or a tautomer thereof, or a salt, a hydrate, or a solvate thereof:

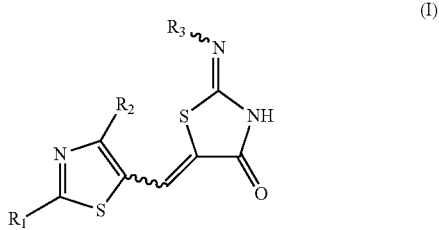

wherein $R_1$ is selected from the group consisting of a hydrogen atom, a linear or branched lower alkyl group, a halogen, a hydroxyl group, an amino group that may have a substituent, and a nonaromatic heterocyclic group that may have a substituent;

$R_2$ is a hydrogen atom, or a linear or branched lower alkyl group;

$R_3$ is selected from the group consisting of a linear or branched lower alkyl group, a cycloalkyl group that may have a substituent, an aryl group that may have a substituent, an arylalkyl group that may have a substituent, a nonaromatic heterocyclic group that may have a substituent, and a heteroaryl group that may have a substituent, or a fused ring group that may have a substituent; and a wavy line, independently for each occurrence, denotes trans (E-form), cis (Z-form) or a mixture (mixed product) thereof.

[2] The compound, a geometric isomer and a tautomer thereof, and a salt, a hydrate, or a solvate thereof described in [1], wherein $R_1$ is a group independently selected from A below:

A:
a hydrogen atom;
a halogen;
a hydroxyl group;
a linear or branched lower alkyl group;
a group represented by a formula: —$NR_{11}R_{12}$ (wherein $R_{11}$ is each independently selected from a hydrogen atom, a linear or branched lower alkyl group that may optionally be substituted by one to three halogen atoms or a cycloalkyl group, or a cycloalkyl group; or $R_{11}$ and $R_{12}$, together with the nitrogen atom to which they are attached, form a nonaromatic heterocyclic ring);

a group represented by a formula: —N($R_{13}$)[(CH$_2$)$_x$—N$R_{14}R_{15}$] (wherein x is 2 to 4; $R_{13}$ is a hydrogen atom or a lower alkyl group; $R_{14}$ and $R_{15}$ are each a hydrogen atom or a lower alkyl group, or $R_{14}$ and $R_{15}$, together with the nitrogen atom to which they are attached, form a nonaromatic heterocyclic ring);

a group represented by a formula: —NHCO—(CH$_2$)$_y$—N$R_{16}R_{17}$ (wherein y is 0 to 3; $R_{16}$ and $R_{17}$ are each a hydrogen atom or a lower alkyl group that may optionally be substituted by an amino group substituted by one or two lower alkyl groups, or $R_{16}$ and $R_{17}$, together with the nitrogen atom to which they are attached, form a nonaromatic heterocyclic ring);

a group represented by a formula: —NHCO—(CH$_2$)$_z$—$R_{18}$ (wherein z is 0 to 3; $R_{18}$ is a lower alkyl group that may optionally be substituted by one to three halogen atoms, a lower alkoxyl group, a lower alkoxycarbonyl group, a carboxyl group, a cycloalkyl group, a nonaromatic heterocyclic group that may optionally be substituted by a lower alkyl group, or an aminocarbonyl group that may be substituted by one or two lower alkyl groups).

[3] The compound, a geometric isomer and a tautomer thereof, and a salt, a hydrate, or a solvate thereof described in [1] or [2],
wherein $R_3$ is an aryl group or a heteroaryl group that may optionally be substituted by one to three groups independently selected from B below:
B:
a linear or branched lower alkyl group that may optionally be substituted by a group selected from the group consisting of one to three halogen atoms, a hydroxyl group, an amino group substituted by one or two lower alkyl groups, and a nonaromatic heterocyclic group;
a lower alkoxy group;
a hydroxyl group;
a halogen;
a nitro group;
an amino group that may optionally be substituted by one or two lower alkyl groups;
a lower alkylcarbonylamino group;
a group represented by a formula: —(CH$_2$)$_k$COOH (wherein k is 0 to 2);
a group represented by a formula: —O—$R_{31}$—$R_{32}$ (wherein $R_{31}$ is a single bond, a lower alkylene group or a cycloalkylene group; $R_{32}$ is a group selected from a hydroxyl group, a carboxyl group, a lower alkoxyl group, a lower alkoxycarbonyl group, an amino group substituted by two lower alkyl groups or by one a lower alkyl group and one lower alkoxycarbonyl group, and a nonaromatic heterocyclic group that may optionally be substituted by a lower alkyl group; and
a group represented by a formula: —CON($R_{33}$)[(CH$_2$)$_m$—$R_{34}$] (wherein m is 0 to 2; $R_{33}$ is a hydrogen atom or a lower alkyl group; $R_{34}$ is an amino group substituted by one or two lower alkyl groups).

[4] The compound, a geometric isomer and a tautomer thereof, and a salt, a hydrate, or a solvate thereof described in [3], wherein said aryl group or heteroaryl group is a phenyl group, a naphthyl group, an indolyl group, an indazolyl group, a quinolyl group, a benzimidazolyl group or a benzotriazolyl group.

[5] The compound, a geometric isomer and a tautomer thereof, and a salt, a hydrate, or a solvate thereof described in [1] or [2], wherein said $R_3$ is a benzyl group having a substituent, and wherein the benzene ring of said benzyl group is substituted with halogen, a lower alkyl group that may optionally be substituted by one to three halogen atoms, or a lower alkoxy group, or wherein the methylene group of said benzyl group is substituted by one or two lower alkyl groups.

[6] The compound, a geometric isomer and a tautomer thereof, and a salt, a hydrate, or a solvate thereof described in [1] or [2], wherein said $R_3$ is an indanyl group or a 1,3-benzodioxolyl group.

[7] The compound, a geometric isomer and a tautomer thereof, and a salt, a hydrate, or a solvate thereof described in [1] or [2], wherein said $R_3$ is a phenyl group having a substituent.

[8] The compound, a geometric isomer and a tautomer thereof, and a salt, a hydrate, or a solvate thereof described in [1] or [2], wherein said $R_3$ is a phenyl group having a substituent, and the substituent is a group represented by a formula: —O—$R_{31}$—$R_{32}$ (wherein $R_{31}$ is a single bond, a lower alkylene group or a cycloalkyne group, and $R_{32}$ is a group selected from a hydroxyl group; a carboxyl group; a lower alkoxy group; a lower alkoxycarbonyl group; an amino group substituted by two lower alkyl groups, or by one lower alkyl group and one lower alkoxy carbonyl group; and a nonaromatic heterocyclic group that may be substituted by a lower alkyl group.

[9] The compound, a geometric isomer and a tautomer thereof, and a salt, a hydrate, or a solvate thereof described in [1] or [2], wherein said $R_1$ is a group represented by a formula: —NHCO—$R_{18}$ (wherein $R_{18}$ is the same as described above).

[10] The compound, a geometric isomer and a tautomer thereof, and a salt, a hydrate, or a solvate thereof described in [1] or [2], wherein said $R_2$ is a hydrogen atom.

[11] A pharmaceutical composition comprising a compound, a geometric isomer and a tautomer thereof, or a salt, a hydrate, or a solvate thereof described in [1] to [10], and a pharmaceutically acceptable carrier.

[12] A production process of a compound described in [1], by reacting a compound represented by the following formula (II) with a compound represented by the following formula (III) in which an imino group has been modified in advance:

Formula (II):

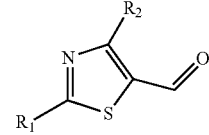

Formula (III):

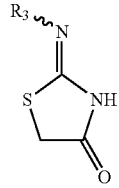

wherein $R_1$, $R_2$ and $R_3$ is the same as $R_1$, $R_2$ and $R_3$ in [1] described above.

[13] A production process of a compound represented by the following formula (I), by reacting a compound represented by the following formula (II) with a compound represented by the following formula (III):

Formula (I):

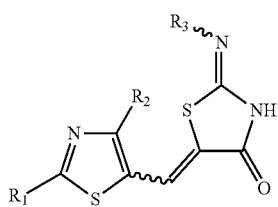

wherein R₁ is selected from the group consisting of a hydrogen atom, a linear or branched lower alkyl group, halogen, a hydroxyl group, an amino group that may have a substituent and a non-aromatic heterocyclic group that may have a substituent;
R₂ is a hydrogen atom or a linear or branched lower alkyl group;
R₃ is selected from the group consisting of a linear or branched lower alkyl group; a cycloalkyl group that may have a substituent, an aryl group that may have a substituent, an arylalkyl group that may have a substituent, a non-aromatic heterocyclic group that may have a substituent, and a heteroaryl group that may have a substituent, or is a fused ring group that may have a substituent; and
a wavy line, independently for each occurrence, denotes trans (E-form), cis (Z-form) or a mixture (mixed product) thereof;

Formula (II):

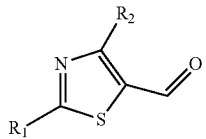

wherein R₁ and R₂ are the same as R₁ and R₂ in the above-mentioned formula (I).

Formula (III):

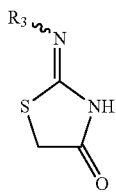

wherein R₃ is the same as R₃ in the above-mentioned formula (I).

[14] The compound, a geometric isomer and a tautomer thereof, or a salt, a hydrate, or a solvate thereof described in [1], which is selected from the group consisting of
(2Z,5Z)-5-[(4-methyl(1,3-thiazol-5-yl))methylene]-2-(phenylazamethylene)-1,3-thiazolidin-4-one,
(2Z,5Z)-N-(5{[4-oxo-2-(phenylazamethylene)-1,3-thiazolidin-5-ylidene]methyl}-1,3-thiazol-2-yl)acetamide,
(2Z,5Z)-5-[2-(ethylamino)(1,3-thiazol-5-yl)]methylene}-2-(phenylazamethylene)-1,3-thiazolidin-4-one,
(2Z,5Z)-5-[2-(butylamino)(1,3-thiazol-5-yl)]methylene}-2-(phenylazamethylene)-1,3-thiazolidin-4-one,
(2Z,5Z)-5-{[2-(dimethylamino)(1,3-thiazol-5-yl)]methylene}-2-(phenylazamethylene)-1,3-thiazolidin-4-one,
(2Z,5Z)-5-[2-(diethylamino)(1,3-thiazol-5-yl)]methylene-2-(phenylazamethylene)-1,3-thiazolidin-4-one,
(2Z,5Z)-5-[(2-{[2-(dimethylamino)ethyl]methylamino}(1,3-thiazol-5-yl))methylene]-2-(phenylazamethylene)-1,3-thiazolidin-4-one,
(2Z,5Z)-5-[(2-bromo (1,3-thiazol-5-yl))methylene]-2-(phenylazamethylene)-1,3-thiazolidin-4-one,
(2Z,5Z)-N-(4-methyl-5-[4-oxo-2-(phenylazamethylene)(1,3-thiazolidin-5-ylidene)]methyl}-1,3-thiazol-2-yl)acetamide,
(2Z,5Z)-5-[(2-amino(1,3-thiazol-5-yl))methylene]-2-(phenylazamethylene)-1,3-thiazolidin-4-one
(2Z,5Z)-2-(phenylazamethylene)-5-(1,3-thiazol-5-ylmethylene)-1,3-thiazolidin-4-one,
(2Z,5Z)-5-[(2-chloro(1,3-thiazol-5-yl))methylene]-2-(phenylazamethylene)-1,3-thiazolidin-4-one,
(2Z,5Z)-2-(dimethylamino)-N-(5-[4-oxo-2-(phenylazamethylene)(1,3-thiazolidin-5-ylidene)]methyl}-1,3-thiazol-2-yl))acetamide,
(2Z,5Z)-5-[(2-hydroxy(1,3-thiazol-5-yl))methylene]-2-[(2-methoxyphenyl)azamethylene]-1,3-thiazolidin-4-one,
(2Z,5Z)-N-[5-({2-[(2-methoxyphenyl)azamethylene]-4-oxo-1,3-thiazolidin-5-ylidene}methyl)-1,3-thiazol-2-yl]acetamide,
(2Z,5Z)-5-[(2-amino(1,3-thiazol-5-yl))methylene]-2-[(2-methoxyphenyl)azamethylene]-1,3-thiazolidin-4-one,
(2Z,5Z)-5-[(2-{[2-(dimethylamino)ethyl]amino}(1,3-thiazol-5-yl)methylene]-2-(phenylazamethylene)-1,3-thiazolidin-4-one,
(2Z,5Z)-5-{[2-[(2-morpholinoethyl)amino](1,3-thiazol-5-yl)]methylene}-2-(phenylazamethylene) -1,3-thiazolidin-4-one,
(2Z,5Z)-3-[N-(5-{[4-oxo-2-(phenylazamethylene)-1,3-thiazolidin-5-ylidene]methyl}-1,3-thiazol-2-yl)carbamoyl]propionic acid,
(2Z,5Z)-5-{[2-(cyclopentylamino)(1,3-thiazol-5-yl)methylene]-2-(phenylazamethylene)-1,3-thiazolidin-4-one,
(2Z,5Z)-4-[N-(5-{[4-oxo-2-(phenylazamethylene)-1,3-thiazolidin-5-ylidene]methyl}-1,3-thiazol-2-yl)carbamoyl]butyric acid,
(2Z,5Z)-5-[2-(cyclohexylamino)(1,3-thiazol-5-yl)methylene]-2-(phenylazamethylene)-1,3-thiazolidin-4-one,
(2Z,5Z)-5-[(2-{[4-(dimethylamino)butyl]amino}(1,3-thiazol-5-yl))methylene]-2-(phenylazamethylene)-1,3-thiazolidin-4-one,
(2Z,5Z)-5-[(2-{[3-(dimethylamino)propyl]amino}(1,3-thiazol-5-yl))methylene]-2-(phenylazamethylene)-1,3-thiazolidin-4-one,
(2Z,5Z)-3-{N-[5-({2-[(2-methoxyphenyl)azamethylene]-4-oxo-1,3-thiazolidin-5-ylidene}methyl) -1,3-thiazol-2-yl]carbamoyl}propionic acid,
(5Z)-3-[N-(5-{[2-(indol-5-ylazamethylene)-4-oxo-1,3-thiazolidin-5-ylidene]methyl]-1,3-thiazol-2-yl)carbamoyl}propionic acid,
(2Z,5Z)-3-(N-{5-[(2-[4-(carboxymethyl)phenyl]azamethylene}-4-oxo-1,3-thiazolidin-5-ylidene) methyl]-1,3-thiazol-2-yl}carbamoyl)propionic acid,
(2Z,5Z)-4-[(5-{[2-(3-carboxypropanoylamino)(1,3-thiazol-5-yl)]methylene}-4-oxo(1,3-thiazolidin-2-ylidene))azamethyl]-3-methoxybenzoic acid,
(2Z,5Z)-4-[(5-{[2-(3-carboxypropanoylamino)(1,3-thiazol-5-yl)]methylene}-4-oxo(1,3-thiazolidin-2-ylidene))azamethyl]benzoic acid, (2Z,5Z)-3-{N-[5-({2-[(4-hydroxy-2-methylphenyl)azamethylene]-4-oxo-1,3-thiazolidin-5-ylidene}methyl)-1,3-thiazol-2-yl]carbamoyl}propionic acid, (2Z,5Z)-3-{N-[5-({2-[(4-hydroxyphenyl]azamethylene}-4-oxo-1,3-thiazolidin-5-ylidene}methyl) -1,3-thiazol-2-yl]carbamoyl}propionic acid, (2Z,5Z)-3-(N-{5-[(2-[4-(acetylamino)phenyl]azamethylene}-4-oxo-1,3-thiazolidin-5-ylidene)methyl]-1,3-thiazol-2-yl}carbamoyl)propionic acid, (2Z,5Z)-3-{N-[5-({2-[(4-methoxy-2-methylphenyl)azamethylene]-4-oxo-1,3-thiazolidin-5-ylidene}methyl)-1,3-thiazol-2-yl]carbamoyl) propionic acid, (2Z,5Z)-3-{N-[5-({2-[(4-methoxyphenyl)azamethylene]-4-oxo-1,3-thiazolidin-5-ylidene}methyl) -1,3-thiazol-2-yl]carbamoyl}propionic acid, (2Z,5Z)-3-{N-[5-({2-[(4-ethylphenyl)azamethylene]-4-oxo-1,3-thiazolidin-5-ylidene}methyl)-1,3-thiazol-2-yl]carbamoyl}propionic acid, (2Z,5Z)-3-{N-[5-({2-[(2,4-dimethylphenyl)azamethylene]-4-oxo-1,3-thiazolidin-5-ylidene}methyl)-1,3-thiazol-2-yl]carbamoyl}propionic acid, (2Z,5Z)-3-{N-[5-({2-[(3,4-dichlorophenyl)azamethylene]-4-oxo-1,3-thiazolidin-5-ylidene}methyl)-1,3-thiazol-2-yl]carbamoyl}propionic acid, (5Z)-3-[N-(5-{[2-(1H-indazol-6-ylazamethylene)-4-oxo-1,3-thiazolidin-5-ylidene]methyl}-1,3-thiazol-2-yl)carbamoyl]propionic acid, (5Z)-3-[N-(5-[({2-(2H-benz[d]1,3-dioxolen-5-ylazamethylene)-4-oxo-1,3-thiazolidin-5-ylidene]methyl}-1,3-thiazol-2-yl)carbamoyl]propionic acid, (5Z)-3-[N-(5-{[2-(1H-indazol-5-ylazamethylene)-4-oxo-1,3-thiazolidin-5-ylidene]methyl]-1,3-thiazol-2-yl)carbamoyl}propionic acid, (5Z)-3-[N-(5-{[2-(indol-7-ylazamethylene)-4-oxo-1,3-thiazolidin-5-ylidene]methyl]-1,3-thiazol-2-yl)carbamoyl]propionic acid, (5Z)-3-[N-(5-{[2-(indan-4-ylazamethylene)-4-oxo-1,3-thiazolidin-5-ylidene]methyl}-1,3-thiazol-2-yl)carbamoyl]propionic acid, (5Z)-3-[N-(5-{[2-(benzimidazol-2-ylazamethylene)-4-oxo-1,3-thiazolidin-5-ylidene]methyl}-1,3-thiazol-2-yl)carbamoyl]propionic acid, (5Z)-3-{N-[5-({2-[(1-methylbenzimidazol-2-yl)azamethylene]-4-oxo-1,3-thiazolidin-5-ylidene}methyl)-1,3-thiazol-2-yl]carbamoyl}propionic acid, (2Z,5Z)-3-{N-[5-({2-[(2,3-dichlorophenyl)azamethylene]-4-oxo-1,3-thiazolidin-5-ylidene}methyl)-1,3-thiazol-2-yl]carbamoyl}propionic acid, (2Z,5Z)-3-{N-[5-({2-[(2,4-dichlorophenyl)azamethylene]-4-oxo-1,3-thiazolidin-5-ylidene}methyl)-1,3-thiazol-2-yl]carbamoyl}propionic acid, (5Z)-3-[N-(5-{[2-(2-naphthylazamethylene)-4-oxo-1,3-thiazolidin-5-ylidene]methyl}-1,3-thiazol -2-yl)carbamoyl]propionic acid, (5Z)-3-{N-[5-({2-[(3-hydroxy(2-naphthyl))azamethylene]-4-oxo-1,3-thiazolidin-5-ylidene]methyl)-1,3-thiazol-2-yl]carbamoyl}propionic acid, (5Z)-3-[N-(5-{[4-oxo-2-(6-quinolylazamethylene)-1,3-thiazolidin-5-ylidene]methyl}-1,3-thiazol -2-yl)carbamoyl] propionic acid, (5Z)-3-[N-(5-{[2-(indol-6-ylazamethylene)-4-oxo-1,3-thiazolidin-5-ylidene]methyl}-1,3-thiazol-2-yl)carbamoyl] propionic acid, (5Z)-3-[N-(5-{[2-(naphthylazamethylene)-4-oxo-1,3-thiazolidin-5-ylidene]methyl}-1,3-thiazol-2-yl)carbamoyl]propionic acid, (2Z,5Z)-3-{N-[5-({4-oxo-2-[(2,4,5-trichlorophenyl)azamethylene]-1,3-thiazolidin-5-ylidene}methyl)-1,3-thiazol-2-yl]carbamoyl}propionic acid, (5Z)-5-[(2-[2-(dimethylamino)ethyl]amino}(1,3-thiazol-5-yl))methylene]-2-(indol-5-ylazamethylene)-1,3-thiazolidin-4-one, (5Z)-5-[(2-{[2-(dimethylamino)ethyl]amino}(1,3-thiazol-5-yl))methylene]-2-(1H-indazol-6-ylazamethylene)-1,3-thiazolidin-4-one, (2Z,5Z)-5-[(2-{[2-(dimethylamino)ethyl]amino}(1,3-thiazol-5-yl)methylene]-2-[(4-hydroxy-2-methylphenyl)azamethylene]-1,3-thiazolidin-4-one, (5Z)-5-[(2-{[3-(dimethylamino)propyl]amino}(1,3-thiazol-5-yl))methylene]-2-(indol-5-ylazamethylene)-1,3-thiazolidin-4-one, (5Z)-5-[(2-[3-(dimethylamino)propyl]amino}(1,3-thiazol-5-yl))methylene]-2-(1H-indazol-6-ylazamethylene)-1,3-thiazolidin-4-one, (2Z,5Z)-5-[(2-{[3-(dimethylamino)propyl]amino}(1,3-thiazol-5-yl)methylene]-2-[(4-hydroxy-2-methylphenyl)azamethylene]-1,3-thiazolidin-4-one, (5Z)-5-[(2-[4-(dimethylamino)butyl]amino}(1,3-thiazol-5-yl))methylene]-2-(1H-indazol-6-ylazamethylene)-1,3-thiazolidin-4-one, (2Z,5Z)-5-[(2-{[4-(dimethylamino)butyl]amino}(1,3-thiazol-5-yl)methylene]-2-[(4-hydroxy-2-methylphenyl)azamethylene]-1,3-thiazolidin-4-one, (5Z)-4-(dimethylamino)-N-(5-{[2-(1H-indazol-6-ylazamethylene)-4-oxo(1,3-thiazolidin-5-ylidene)]methyl}(1,3-thiazol-2-yl))butylamide, (5Z)-3-(dimethylamino)-N-(5-[2-(1H-indazol-6-ylazamethylene)-4-oxo(1,3-thiazolidin-5-ylidene)]methyl}(1,3-thiazol-2-yl))propionamide, (5Z)-2-(1H-indazol-6-ylazamethylene)-5-({2-[(3-morpholinopropyl)amino](1,3-thiazol-5-yl)}methylene)-1,3-thiazolidin-4-one, (2Z,5Z)-2-[(4-hydroxy-2-methylphenyl)azamethylene][(3-morpholinopropyl)amino](1,3-thiazol-5-yl)}methylene)-1,3-thiazolidin-4-one, (5Z)-methyl 3-[N-(5-{[2-(1H-indazol-6-ylazamethylene)-4-oxo-1,3-thiazolidin-5-ylidene]methyl}-1,3-thiazol -2-yl)carbamoyl]propanoate, (2Z,5Z)-methyl 3-{N-[5-({2-[(4-hydroxy-2-methylphenyl)azamethylene]-4-oxo-1,3-thiazolidin-5-ylidene}methyl)-1,3-thiazol-2-yl]carbamoyl}propanoate, (5Z)-2-(1H-indazol-6-ylazamethylene)-5-({2-[(3-(1-pyrrolidinyl)propyl)amino](1,3-thiazol-5-yl)}methylene)-1,3-thiazolidin-4-one, (2Z,5Z)-2-[(4-hydroxy-2-methylphenyl)azamethylene]-5-({2-[(3-(1-pyrroridinyl)propyl)amino](1,3-thiazol-5-yl)}methylene)-1,3-thiazolidin-4-one, (5Z)-N-(5-{[2-(1H-indazol-6-ylazamethylene)-4-oxo(1,3-thiazolidin-5-ylidene)]methyl}(1,3-thiazol-2-yl))-2-(4-methylpiperazinyl)acetamide, (2Z,5Z)-N-[5-({2-[(4-hydroxy-2-methylphenyl)azamethylene]-4-oxo(1,3-thiazolidin-5-ylidene)]methyl}(1,3-thiazol-2-yl)]-2-(4-methylpiperazinyl)acetamide, (5Z)-5-[(2-amino(1,3-thiazol-5-yl)) methylene]-2-(1H-indazol-6-ylazamethylene)-1,3-thiazolidin-4-one, (2Z,5Z)-5-[(2-amino(1,3-thiazol-5-yl))methylene]-2-[(4-hydroxy-2-methylphenyl)azamethylene]-1,3-thiazolidin-4-one, (5Z)-cyclopropyl-N-(5-[2-(1H-indazol-6-ylazamethylene)-4-oxo(1,3-thiazolidin-5-ylidene)]methyl) (1,3-thiazol-2-yl))carboxamide, (2Z,5Z)-cyclopropyl-N-[5-({2-[(4-hydroxy-2-methylphenyl)azamethylene]-4-oxo(1,3-thiazolidin-5-ylidene)}methyl)(1,3-thiazol-2-yl)]carboxamide, (5Z)-N-(5-[2-(1H-indazol-6-ylazamethylene)-4-oxo-1,3-thiazolidin-5-ylidene]methyl)-1,3-thiazol-2-yl) acetamide, (5Z)-N-[5-({2-[(1-methyl(1H-indazol-6-yl))azamethylene]-4-oxo-1,3-thiazolidin-5-ylidene}meth yl)-1,3-thiazol-2-yl]acetamide, (5Z)-N-[5-({2-[(1-methylindol-5-yl)azamethylene]-4-oxo-1,3-thiazolidin-5-ylidene]methyl)-1,3-thiazol-2-yl]acetamide, (5Z)-N-[5-({2-[(1-methylindol-6-yl)azamethylene]-4-oxo-1,3-thiazolidin-5-ylidene}methyl)-1,3-thiazol-2-yl]acetamide, (2Z,5Z)-2-[(2,4-dimethylphenyl)azamethylene]-5-({2-[(3-pyrrolidinylpropyl)amino](1,3-thiazol-5-yl)}methylene)-1,3-thiazolidin-4-one, (2Z,5Z)-2-[(2,4-dimethylphenyl)azamethylene]-5-({2-[(2-pyrrolidinylethyl)amino](1,3-thiazol-5-yl)}methylene)-1,3-thiazolidin-4-one, (2Z,5Z)-N-[5-({2-[(2,4-dimethylphenyl)azamethylene]-4-oxo(1,3-thiazolidin-5-ylidene)}methyl) (1,3-thiazol-2-yl)]cyclopropylcarboxamide, (2Z,5Z)-2-[(2,4-dimethylphenyl)azamethylene]-5-({2-[(3-morpholinopropyl)amino](1,3-thiazol-5-yl)}methylene)-1,3-thiazolidin-4-one, (2Z,5Z)-5-[2-(tert-butyl)(1,3-thiazol-5-yl)]methylene}-2-[(2,4-dimethylphenyl)azamethylene]-1,3-thiazolidin-4-one, (2Z,5Z)-5-{[2-(tert-butyl)(1,3-thiazol-5-yl)]methylene}-2-[(4-hydroxy-2-methylphenyl)azamethylene]-1,3-thiazolidin-4-one, (2Z,5Z)-5-{[(2-bromo(1,3-thiazol-5-yl))methylene]-2-[(4-hydroxy-2-methylphenyl)azamethylene]-1,3-thiazolidin-4-one, (2Z,5Z)-2-[(2,4-dimethylphenyl)azamethylene]-5-[(2-bromo(1,3-thiazol-5-yl))methylene]-1,3-thiazolidin-4-one, (2Z,5Z)-2-[(2,4-dichlorophenyl)azamethylene]-5-({2-[(3-morpholinopropyl)amino](1,3-thiazol-5-yl)}methylene)-1,3-thiazolidin-4-one, (2Z,5Z)-N-[5-({2-[2-(4-chlorophenyl)-1-azaethylidene]-4-oxo-1,3-thiazolidin-5-ylidene)methyl) -1,3-thiazol-2-yl]acetamide, (2Z,5Z)-N-[5-({2-[2-(3-chlorophenyl)-1-azaethylidene]-4-oxo-1,3-thiazolidin-5-ylidene}methyl) -1,3-thiazol-2-yl]acetamide, (2Z,5Z)-N-[5-({2-[2-(3,4-dichlorophenyl)-1-azaethylidene]-4-oxo-1,3-thiazolidin-5-ylidene}methyl)-1,3-thiazol-2-yl]acetamide, (2Z,5Z)-N-[5-({2-[2-(2,4-dichlorophenyl)-1-azaethylidene]-4-oxo-1,3-thiazolidin-5-ylidene}methyl)-1,3-thiazol-2-yl]acetamide, (2Z,5Z)-N-[5-({2-[2-(3-chloro-4-fluorophenyl)-1-azaethylidene]-4-oxo-1,3-thiazolidin-5-ylidene}methyl)-1,3-thiazol-2-yl]acetamide, (2Z,5Z)-N-[5-({2-[2-(2-chlorophenyl)-1-azaethylidene]-4-oxo(1,3-thiazolidin-5-ylidene)}methyl) (1,3-thiazol-2-yl)]cyclopropylcarboxamide, (2Z,5Z)-cyclopropyl-N-[5-({2-[2-(3-methoxyphenyl)-1-azaethylidene]-4-oxo(1,3-thiazolidin-5-ylidene)}methyl)(1,3-thiazol-2-yl)]carboxamide, (2Z,5Z)-N-[5-({2-[2-(3-bromophenyl)-1-azaethylidene]-4-oxo(1,3-thiazolidin-5-ylidene)}methyl) (1,3-thiazol-2-yl)]cyclopropylcarboxamide, (2Z,5Z)-N-[5-({2-[2-(3-chlorophenyl)-1-azaethylidene]-4-oxo(1,3-thiazolidin-5-ylidene)}methyl) (1,3-thiazol-2-yl)]cyclopropylcarboxamide, (2Z,5Z)-cyclopropyl-N-{5-[(4-oxo-2-{2-[3-(trifluoromethyl)phenyl]-1-azaethylidene}(1,3-thiazolidin-5-ylidene))methyl](1,3-thiazol-2-yl)}carboxamide, (2Z,5Z)-N-[5-({2-[2-(3-chloro-4-fluorophenyl)-1-azaethylidene]-4-oxo(1,3-thiazolidin-5-ylidene)}methyl)(1,3-thiazol-2-yl)]cyclopropylcarboxamide, (5Z)-cyclopropyl-N-[5-({2-[(1-methylindol-5-yl)azamethylene]-4-oxo(1,3-thiazolidin-5-ylidene) }methyl)-1,3-thiazol-2-yl]carboxamide, (2Z,5Z)-cyclopropyl-N-(5-{[4-oxo-2-(2-phenyl-1-azaethylidene)(1,3-thiazolidin-5-ylidene)]meth yl}(1,3-thiazol-2-yl)) carboxamide, (2Z,5Z)-cyclopropyl-N-(5-[2-(2-methyl-2-phenyl-1-azapropylidene)-4-oxo(1,3-thiazolidin-5-ylidene)]methyl}(1,3-thiazol-2-yl)) carboxamide, (2Z,5Z)-2-[(2,4-dimethylphenyl)azamethylene]-5-({2-[(2,2,2-trifluoroethyl)amino](1,3-thiazol-5-yl)}methylene)-1,3-thiazolidin-4-one, (2Z,5Z)-2-[(4-hydroxy-2-methylphenyl)azamethylene]-5-({2-[(2,2,2-trifluoroethyl)amino](1,3-thiazol-5-yl)}methylene)-1,3-thiazolidin-4-one, (2Z,5Z)-N-[5-({2-[(2,4-dimethylphenyl)azamethylene]-4-oxo(1,3-thiazolidin-5-ylidene)}methyl) (1,3-thiazol-2-yl)]-3,3,3-trifluoropropionamide, (2Z,5Z)-3,3,3-trifluoro-N-[5-({2-[(4-hydroxy-2-methylphenyl)azamethylene]-4-oxo(1,3-thiazolidin-5-ylidene)}methyl)(1,3-thiazol-2-yl)]propionamide, (2Z,5Z)-N-[5-({2-[2-(2,5-dichlorophenyl)-1-azaethylidene]-4-oxo(1,3-thiazolidin-5-ylidene)}methyl)(1,3-thiazol-2-yl)]cyclopropylcarboxamide, (2Z,5Z)-N-[5-({2-[2-(2,3-dichlorophenyl)-1-azaethylidene]-4-oxo(1,3-thiazolidin-5-ylidene)}methyl)(1,3-thiazol-2-yl)]cyclopropylcarboxamide, (2Z,5Z)-N-[5-({2-[(2,4-dimethylphenyl)azamethylene]-4-oxo(1,3-thiazolidin-5-ylidene)}methyl) (1,3-thiazol-2-yl)](1-methyl(4-piperidyl))carboxamide, (2Z,5Z)-N-[5-({2-[(4-hydroxy-2-methylphenyl)azamethylene]-4-oxo(1,3-thiazolidin-5-ylidene)}methyl)(1,3-thiazol-2-yl)](1-methyl(4-piperidyl))carboxamide, (5Z)-N-(5-{[2-({1-[2-(dimethylamino)ethyl]indol-5-yl}azamethylene)-4-oxo(1,3-thiazolidin-5-yl idene)]methyl}(1,3-thiazol-2-yl))cyclopropylcarboxamide, (5Z)-cyclopropyl-N-{5-[(2-{[1-(2-morpholinoethyl)indol-5-yl]azamethylene}-4-oxo(1,3-thiazolidin-5-ylidene))methyl](1,3-thiazol-2-yl)}carboxamide, (5Z)-cyclopropyl-N-{5-[(4-oxo-2-{[1-(2-(1-pyrroridinyl)ethyl)indol-5-yl]azamethylene}-(1,3-thiazolidin-5-ylidene))methyl](1,3-thiazol-2-yl)}carboxamide, (5Z)-cyclopropyl-N-{5-[(4-oxo-2-[1-(2-piperidinoethyl)indol-5-yl]azamethylene}-(1,3-thiazolidin-5-ylidene))methyl](1,3-thiazol-2-yl)}carboxamide, (5Z)-cyclopropyl-N-{5-[(4-oxo-2-{[1-(3-piperidinopropyl)indol-5-yl]azamethylene}-(1,3-thiazolidin-5-ylidene))methyl](1,3-thiazol-2-yl)}carboxamide, (2Z,5Z)-cyclopropyl-N-{5-[(2-{[2-methyl-4-(2-piperidinoethoxy)phenyl]azamethylene}-4-oxo(1,3-thiazolidin-5-ylidene))methyl](1,3-thiazol-2-yl)}carboxamide, (5Z)-N-(5-{[2-({1-[3-(dimethylamino)propyl]indol-5-yl}azamethylene)-4-oxo(1,3-thiazolidin-5-ylidene)]methyl}(1,3-thiazol-2-yl))cyclopropylcarboxamide, (2Z,5Z)-cyclopropyl-N-{5-[(2-{[2-methyl-4-(2-(1-pirroridinyl)ethoxy)phenyliazamethylene}-4-oxo(1,3-thiazolidin-5-ylidene))methyl](1,3-thiazol-2-yl)}carboxamide, (2Z,5Z)-cyclopropyl-N-{5-[(2-{[2-methyl-4-(2-morpholinoethoxy)phenyl]azamethylene)-4-oxo(1,3-thiazolidin-5-ylidene))methyl](1,3-thiazol-2-yl)}carboxamide, (2Z,5Z)-N-(5-({[2-({4-[2-(dimethylamino)ethoxy]-2-methylphenyl}azamethylene)-4-oxo(1,3-thiazolidin-5-ylidene)]methyl}(1,3-thiazol-2-yl))cyclopropylcarboxamide, (2Z,5Z)-N-(5-({[2-({4-[3-(dimethylamino)propoxy]-2-methylphenyl}azamethylene)-4-oxo(1,3-thiazolidin-5-ylidene)]methyl}(1,3-thiazol-2-yl))cyclopropylcarboxamide, (2Z,5Z)-N-[5-({2-[(2,4-dimethylphenyl)azamethylene]-4-oxo(1,3-thiazolidin-5-ylidene)}methyl) (1,3-thiazol-2-yl)](ethylamino)carboxamide, (2Z,5Z)-(ethylamino)-N-[5-({2-[(4-hydroxy-2-methylphenyl)azamethylene]-4-oxo(1,3-thiazolidin-5-ylidene)}methyl)(1,3-thiazol-2-yl)]carboxamide, (2Z,5Z)-N-(5-({[2-({4-[2-(dimethylamino)ethoxy]-2-fluorophenyl]azamethylene)-4-oxo(1,3-thiazolidin-5-ylidene)}methyl)(1,3-thiazol-2-yl))cyclopropylcarboxamide, (2Z,5Z)-N-(5-({[2-({4-[2-(dimethylamino)ethoxy]phenyl}azamethylene)-4-oxo(1,3-thiazolidin-5-ylidene)}methyl)(1,3-thiazol-2-yl))cyclopropylcarboxamide, (5Z)-(ethylamino)-N-{5-[(2-{[1-(2-morpholinoethyl)indol-5-yl]azamethylene]-4-oxo(1,3-thiazolidin-5-ylidene))methyl) (1,3-thiazol-2-yl)}carboxamide, (5Z)-N-[5-({2-[(2,4-dimethylphenyl)azamethylene]-4-oxo (1,3-thiazolidin-5-ylidene)}methyl)(1,3-thiazol-2-yl)]ethoxycarboxamide, (2Z,5Z)-(dimethylamino)-N-[5-({2-[(2,4-dimethylphenyl)azamethylene]-4-oxo(1,3-thiazolidin-5-ylidene)}methyl)(1,3-thiazol-2-yl)]carboxamide, (2Z,5Z)-N-(5-[2-({4-[2-(dimethylamino)ethoxy]-2-methylphenyl]azamethylene)-4-oxo(1,3-thiazolidin-5-ylidene)}methyl)(1,3-thiazol-2-yl))ethoxy carboxamide, (2Z,5Z)-N-[5-({2-[(2,4-dimethylphenyl)azamethylene]-4-oxo(1,3-thiazolidin-5-ylidene)}}methyl) (1,3-thiazol-2-yl)](1-(4-methyl)piperazinyl)carboxamide, (2Z,5Z)-(dimethylamino)-N-(5-[2-({4-[2-(dimethylamino)ethoxy]-2-methylphenyl]azamethylene)-4-oxo(1,3-thiazolidin-5-ylidene)}methyl (1,3-thiazol-2-yl))carboxamide, (2Z,5Z)-[2-(dimethylamino)ethyl]methylamino}-N-[5-({2-[(2,4-dimethylphenyl)azamethylene]-4-oxo(1,3-thiazolidin-5-ylidene)}methyl)(1,3-thiazol-2-yl)]carboxamide, (2Z,5Z)-cyclopropyl-N-(5-{[2-({2-methyl-4-[2-(1-(4-methyl)piperazinyl)ethoxy]phenyl azamethylene)-4-oxo(1, 3-thiazolidin-5-ylidene)}methyl)(1,3-thiazol-2-yl))carboxamide, (2Z,5Z)-2-[(5-{[2-(cyclopropylcarbonylamino)(1,3-thiazol-5-yl)]methylene}-4-oxo(1,3-thiazolidin-2-ylidene))azamethyl]-5-methoxybenzoic acid, (2Z,5Z)-N-(5-{[2-({4-[2-(dimethylamino)ethoxy]-2-methylphenyl}azamethylene)-4-oxo(1,3-thiazolidin-5-ylidene)]methyl}(1,3-thiazol-2-yl))methoxycarboxamide, (2Z,5Z)-cyclopropyl-N-{5-[(2-[2-methyl-4-(1-methyl(4-piperidyloxy))phenyl]azamethylene)-4-oxo(1,3-thiazolidin-5-ylidene))methyl](1,3-thiazol-2-yl)}carboxamide, (2Z,5Z)-N-(5-[2-({4-[2-(diethylamino)ethoxy]-2-methylphenyl]azamethylene)-4-oxo(1,3-thiazolidin-5-ylidene)]methyl}(1,3-thiazol-2-yl))cyclopropylcarboxamide, (2Z,5Z)-N-(2-{4-[(5-[2-(cyclopropylcarbonylamino)(1,3-thiazol-5-yl)]methylene}-4-oxo(1,3-thiazolidin-2-ylidene))azamethyl]-3-methylphenoxy}ethyl)methoxy-N-methylcarboxamide, (2Z,5Z)-N-(5-[2-({4-[2-(dimethylamino)ethoxy]-2-methoxyphenyl}azamethylene)-4-oxo(1,3-thiazolidin-5-ylidene)]methyl}(1,3-thiazol-2-yl))cyclopropylcarboxamide, (2Z,5Z)-cyclopropyl-N-{5-[(2-[2-methyl-4-(1-methylpyrrolidin-3-yloxy)phenyl]azamethylene}-4-oxo(1,3-thiazolidin-5-ylidene))methyl](1,3-thiazol-2-yl)}carboxamide, (2Z,5Z)-4-{4-[(5-{[2-(cyclopropylcarbonylamino)(1,3-thiazol-5-yl)]methylene-4-oxo(1,3-thiazolidin-2-ylidene))azamethyl]-3-methylphenoxy}butyric acid, (2Z,5Z)-N-[2-(dimethylamino)ethyl]{4-[(5-[2-(cyclopropylcarbonylamino)(1,3-thiazol-5-yl)}methylene]-4-oxo(1,3-thiazolidin-2-ylidene))azamethyl]-3-methylphenyl]carboxamide, (2Z,5Z)-N-[2-(dimethylamino)ethyl]{4-[(5-{[2-(cyclopropylcarbonylamino)(1,3-thiazol-5-yl)]methylene}-4-oxo(1,3-thiazolidin-2-ylidene))azamethyl]-3-methylphenyl}-N-methylcarboxamide, (2Z,5Z)-N-[5-({2-[(4-chloro-2-methylphenyl)azamethylene]-4-oxo(1,3-thiazolidin-5-ylidene)}methyl)(1,3-thiazol-2-yl)](1-methyl(4-piperidyl))carboxamide, (2Z,5Z)-N-[5-({2-[(4-methoxy-2-methylphenyeazamethylene]-4-oxo(1,3-thiazolidin-5-ylidene)}methyl)(1,3-thiazol-2-yl)](1-methyl(4-piperidyl))carboxamide, (2Z,5Z)-N-[5-({2-[(2,4-dichlorophenyl)azamethylene]-4-oxo(1,3-thiazolidin-5-ylidene)}methyl) (1,3-thiazol-2-yl)](1-methyl(4-piperidyl))carboxamide, (2Z,5Z)-N-(5-[2-({4-[2-(dimethylamino)ethoxy]-2-chlorophenyl}azamethylene)-4-oxo(1,3-thiazolidin-5-ylidene)]methyl}(1,3-thiazol-2-yl)cyclopropylcarboxamide, (2Z,5Z)-N-{5-[(2-[2-chloro-4-(1-methyl(4-piperidyloxy))phenyl]azamethylene}-4-oxo(1,3-thiazolidin-5-ylidene))methyl](1,3-thiazol-2-yl)}cyclopropylcarboxamide, (2Z,5Z)-ethyl 4-{4-[(5-[2-(cyclopropylcarbonylamino)(1,3-thiazol-5-yl)]methylene}-4-oxo(1,3-thiazolidin-2-ylidene))azamethyl]-3-methylphenoxy}cyclohexanecarboxylate, (2Z,5Z)-N-{5-[(2-[4-((3S)-1-methylpyrrolidin-3-yloxy)-2-(trifluoromethyl)phenyl]azamethylene}-4-oxo(1,3-thiazolidin-5-ylidene))methyl](1,3-thiazol-2-yl)}cyclopropylcarboxamide, (2Z,5Z)-4-{4-[(5-[2-(cyclopropylcarbonylamino)(1,3-thiazol-5-yl)]methylene}-4-oxo(1,3-thiazolidin-2-ylidene)) azamethyl]-3-(trifluoromethyl) phenoxy}cyclohexanecarboxylic acid, (2Z,5Z)-cyclopropyl-N-{5-[(2-[4-(1-methyl(4-piperidyloxy))-2-(trifluoromethyl)phenyl]azamethylene}-4-oxo (1,3-thiazolidin-5-ylidene))methyl](1,3-thiazol-2-yl)}carboxamide, (2Z,5Z)-N-(5-[2-({4-[2-(diethylamino)ethoxy]-2-(trifluoromethyl)phenyl}azamethylene)-4-oxo (1,3-thiazolidin-5-ylidene)]methyl}(1,3-thiazol-2-yl))cyclopropylcarboxamide, (2Z,5Z)-4-{4-[(5-{[2-(cyclopropylcarbonylamino)(1,3-thiazol-5-yl)]methylene}-4-oxo(1,3-thiazolidin-2-ylidene)) azamethyl]-3-methylphenoxy}cyclohexanecarboxylic acid, (5Z)-N-(5-[2-(indol-5-ylazamethylene)-4-oxo-1,3-thiazolidin-5-ylidene]methyl}-1,3-thiazol-2-yl)acetamide, (2Z,5Z)-N-(5-{[2-(azapentylidene)-4-oxo-1,3-thiazolidin-5-ylidene]methyl}-1,3-thiazol-2-yl)acetamide, (2Z,5Z)-N-[5-({2-[2-(2-chlorophenyl)-1-azaethylidene]-4-oxo-1,3-thiazolidin-5-ylidene}methyl) -1,3-thiazol-2-yl] acetamide, (5Z)-N-(5-[2-(indanylazamethylene)-4-oxo-1,3-thiazolidin-5-ylidene]methyl}-1,3-thiazol-2-yl)acetamide, (5Z)-N-(5-[2-(indol-6-ylazamethylene)-4-oxo-1,3-thiazolidin-5-ylidene]methyl}-1,3-thiazol-2-yl)acetamide,
(2Z,5Z)-N-[5-({2-[(2,4-dimethylphenyl)azamethylene]-4-oxo-1,3-thiazolidin-5-ylidene}methyl)-1,3-thiazol-2-yl]acetamide,
(2Z,5Z)-N-[5-({2-[(4-hydroxy-2-methylphenyl)azamethylene]-4-oxo-1,3-thiazolidin-5-ylidene}methyl)-1,3-thiazol-2-yl]acetamide,
(2Z,5Z)-N-[5-({2-[(2,4-dimethoxyphenyl)azamethylene]-4-oxo-1,3-thiazolidin-5-ylidene]methyl) -1,3-thiazol-2-yl]acetamide,
(2Z,5Z)-N-{5-[(2-{[3-(hydroxymethyl)-2-methylphenyl]azamethylene}-4-oxo-1,3-thiazolidin-5-ylidene)methyl]-1,3-thiazol-2-yl}acetamide,
(2Z,5Z)-N-[5-({2-[(4-methoxy-2-methylphenyl)azamethylene]-4-oxo-1,3-thiazolidin-5-ylidene}methyl)-1,3-thiazol-2-yl]acetamide,
(2Z,5Z)-N-{5-[(2-[2-(isopropyl)phenyl]azamethylene}-4-oxo-1,3-thiazolidin-5-ylidene)methyl]-1,3-thiazol-2-yl}acetamide,
(2Z,5Z)-N-[5-({2-[(2,3-dimethylphenyl)azamethylene]-4-oxo-1,3-thiazolidin-5-ylidene}methyl)-1,3-thiazol-2-yl]acetamide,
(5Z)-N-(5-[2-(indan-4-ylazamethylene)-4-oxo-1,3-thiazolidin-5-ylidene]methyl}-1,3-thiazol-2-yl)acetamide,
(2Z,5Z)-N-[5-({2-[(3-methoxy-2-methylphenyl)azamethylene]-4-oxo-1,3-thiazolidin-5-ylidene}methyl)-1,3-thiazol-2-yl]acetamide,
(5Z)-N-(5-{[2-(2H-benzo[3,4-d]1,3-dioxolan-5-ylazamethylene)-4-oxo-1,3-thiazolidin-5-ylidene}methyl]-1,3-thiazol-2-yl)acetamide,
(5Z)-5-[(2-amino(1,3-thiazol-5-yl))methylene]-2-(indol-6-ylazamethylene)-1,3-thiazolidin-4-one
(2Z,5Z)-N-[5-({2-[(3-hydroxy-2-methylphenyl)azamethylene]-4-oxo-1,3-thiazolidin-5-ylidene}methyl)-1,3-thiazol-2-yl]acetamide,
(2Z,5Z)-5-[(2-amino(1,3-thiazol-5-yl))methylene]-2-[(4-hydroxy-2-methylphenyl)azamethylene]-1,3-thiazolidin-4-one,
(2Z,5Z)-5-[(2-amino(1,3-thiazol-5-yl))methylene]-2-[(2,4-dimethoxyphenyl)azamethylene]-1,3-thiazolidin-4-one,
(5Z)-5-[(2-amino(1,3-thiazol-5-yl))methylene]-2-(indan-4-ylazamethylene)-1,3-thiazolidin-4-one,
(2Z,5Z)-5-[(2-amino(1,3-thiazol-5-yl))methylene]-2-[(3-methoxy-2-methylphenyl)azamethylene]-1,3-thiazolidin-4-one,
(2Z,5Z)-5-[(2-amino(1,3-thiazol-5-yl))methylene]-2-[(4-methoxy-2-methylphenyl)azamethylene]-1,3-thiazolidin-4-one,
(2Z,5Z)-N-[5-({2-[(2-methyl-4-nitrophenyl)azamethylene]-4-oxo-1,3-thiazolidin-5-ylidene}methyl)-1,3-thiazol-2-yl]acetamide,
(5Z)-N-(5-[2-(indol-7-ylazamethylene)-4-oxo-1,3-thiazolidin-5-ylidene]methyl}-1,3-thiazol-2-yl)acetamide,
(5Z)-N-(5-{[2-(benzimidazol-5-ylazamethylene)-4-oxo-1,3-thiazolidin-5-ylidene]methyl}-1,3-thiazol-2-yl)acetamide,
(5Z)-N-(5-[2-(benzotriazol-5-ylazamethylene)-4-oxo-1,3-thiazolidin-5-ylidene]methyl}-1,3-thiazol-2-yl)acetamide,
(2Z,5Z)-N-[5-({2-[(2-hydroxyphenyl)azamethylene]-4-oxo-1,3-thiazolidin-5-ylidene}methyl)-1,3-thiazol-2-yl]acetamide,
(2Z,5Z)-5-[(2-amino(1,3-thiazol-5-yl))methylene]-2-[2-(2-chlorophenyl)-1-azaethylidene]-1,3-thiazolidin-4-one,
(2Z,5Z)-N-[5-({2-[(2-bromophenyl)azamethylene]-4-oxo-1,3-thiazolidin-5-ylidene}methyl)-1,3-thiazol-2-yl]acetamide,
(2Z,5Z)-5-[(2-amino(1,3-thiazol-5-yl))methylene]-2-[(2,3-dimethylphenyl)azamethylene]-1,3-thiazolidin-4-one,
(2Z,5Z)-5-[(2-amino(1,3-thiazol-5-yl))methylene]-2-[(2,4-dimethylphenyl)azamethylene]-1,3-thiazolidin-4-one,
(2Z,5Z)-N-(5-[2-({4-[2-(dimethylamino)ethoxy]-2-methylphenyl}azamethylene)-4-oxo-1,3-thiazolidin-5-ylidene]methyl-1,3-thiazol-2-yl)acetamide,
(2Z,5Z)-N-{5-[(2-{[2-methyl-4-(2-(1-pyrrolidinyl)ethoxy)phenyliazamethylene}-4-oxo-1,3-thiazolidin-5-ylidene)methyl]-1,3-thiazol-2-yl]acetamide,
(2Z,5Z)-N-(5-{[2-({4-[3-(dimethylamino)propoxy]-2-methylphenyl}azamethylene)-4-oxo-1,3-thiazolidin-5-ylidene]methyl}-1,3-thiazol-2-yl)acetamide,
(2Z,5Z)-N-{5-[(2-[4-(2-methoxyethoxy)-2-methylphenyl]azamethylene}-4-oxo-1,3-thiazolidin-5-ylidene)methyl]-1,3-thiazol-2-yl}acetamide,
(2Z,5Z)-N-{4-[(5-[2-(acetylamino)(1,3-thiazol-5-yl)]methylene]-4-oxo(1,3-thiazolidin-2-ylidene))azamethyl}-3-methylphenyl}acetamide,
(2Z,5Z)-N-{5-[(2-[4-(2-hydroxyethoxy)-2-methylphenyl]azamethylene}-4-oxo-1,3-thiazolidin-5-ylidene)methyl]-1,3-thiazol-2-yl}acetamide,
(2Z,5Z)-N-{5-[(2-{[4-(3-hydroxypropoxy)-2-methylphenyl]azamethylene}-4-oxo-1,3-thiazolidin-5-ylidene)methyl]-1,3-thiazol-2-yl}acetamide,
(2Z,5Z)-N-[5-({2-[(4-hydroxy-2,3-dimethylphenyl)azamethylene]-4-oxo-1,3-thiazolidin-5-ylidene}methyl)-1,3-thiazol-2-yl]acetamide,
(2Z,5Z)-N-[5-({2-[(2-chloro-4-hydroxyphenyl)azamethylene]-4-oxo-1,3-thiazolidin-5-ylidene}methyl)-1,3-thiazol-2-yl]acetamide,
(2Z,5Z)-N-{5-[(2-[2-methyl-4-(2-morpholinoethoxy)phenyl]azamethylene}-4-oxo-1,3-thiazolidin-5-ylidene)methyl]-1,3-thiazol-2-yl}acetamide,
(2Z,5Z)-N-{5-[(2-[4-hydroxy-2-(trifluoromethyl)phenyl]azamethylene}-4-oxo-1,3-thiazolidin-5-ylidene)methyl]-1,3-thiazol-2-yl}acetamide,
(2Z,5Z)-N-[5-({2-[(3-fluoro-4-hydroxyphenyl)azamethylene]-4-oxo-1,3-thiazolidin-5-ylidene}methyl)-1,3-thiazol-2-yl]acetamide,
(2Z,5Z)-N-{5-[(2-{[2-methyl-4-(methylamino)phenyl]azamethylene}-4-oxo-1,3-thiazolidin-5-yl idene)methyl]-1,3-thiazol-2-yl}acetamide,
(2Z,5Z)-N-{5-[(2-[4-(dimethylamino)-2-methylphenyl]azamethylene}-4-oxo-1,3-thiazolidin-5-ylidene)methyl]-1,3-thiazol-2-yl}acetamide
(2Z,5Z)-ethyl 2-{-4-[(5-{[2-cyclopropylcarbonylamino)(1,3-thiazol-5-yl)]methylene}-4-oxo(1,3-thiazolidin-2-ylidene)]azamethyl]-3-methylphenoxy}acetate,
(2Z,5Z)-2-{4-[(5-[2-cyclopropylcarbonylamino)(1,3-thiazol-5-yl)]methylene}-4-oxo(1,3-thiazolidin-2-ylidene)]azamethyl]3-methylphenoxy}acetic acid,
(2Z,5Z)-5-[(2-amino(1,3-thiazol-5-yl))methylene]-2-{[2-methyl-4-(1-methyl(4-piperidyloxy))phenyl]azamethylene}-1,3-thiazolidin-4-one,
(2Z,5Z)-5-[(2-amino(1,3-thiazol-5-yl))methylene]-2-({4-[3-(dimethylamino)propoxy]-2-methylphenyl}azamethylene)-1,3-thiazolidin-4-one,
(2Z,5Z)-5-[(2-amino(1,3-thiazol-5-yl))methylene]-2-({2-methyl-4-[2-(4-methylpiperazinyl)ethoxy]phenyl}azamethylene)-1,3-thiazolidin-4-one,
(2Z,5Z)-5-[(2-amino(1,3-thiazol-5-yl))methylene]-2-{[2-chloro-4-(2-piperidylethoxy)phenyl]azamethylene}-1,3-thiazolidin-4-one, (2Z,5Z)-cyclopropyl-N-[5-({2-[(4-methoxy-2-methylphenyl)azamethylene]-4-oxo(1,3-thiazolidin-5-ylidene)}methyl)(1,3-thiazol-2-yl)]carboxamide, (2Z,5Z)-2-({4-[2-(dimethylamino)ethoxy]-2-methylphenyl}azamethylene)-5-[(2-piperidyl(1,3-thiazol-5-yl))methylene]-1,3-thiazolidin-4-one, (2Z,5Z)-2-{[2-methyl-4-(1-methylpyrroridin-3-yloxy)phenyl]azamethylene}-5-[(2-piperidyl(1,3-thiazol-5-yl))methylene]-1,3-thiazolidin-4-one, (2Z,5Z)-2-[2-methyl-4-(2-morpholin-4-ylethoxy)phenyl]azamethylene}-5-[(2-piperidyl(1,3-thiazol-5-yl))methylene]-1,3-thiazolidin-4-one, (2Z,5Z)-2-({4-[2-(dimethylamino)ethoxy]-2-methylphenyl}azamethylene)-5-{[2-(ethylamino)(1,3-thiazol-5-yl)]methylene}-1,3-thiazolidin-4-one, (2Z,5Z)-2-({4-[2-(dimethylamino)ethoxy]-2-methylphenyl}azamethylene)-5-[2-(cyclopropylmethyl)amino](1,3-thiazol-5-yl)}methylene)-1,3-thiazolidin-4-one, (2Z,5Z)-2-({4-[2-(dimethylamino)ethoxy]-2-methylphenyl}azamethylene)-5-[2-(cyclopentylamino)(1,3-thiazol-5-yl)]methylene}-1,3-thiazolidin-4-one, and (2Z,5Z)-5-[2-(cyclopropylamino)(1,3-thiazol-5-yl)]methylene]-2-{[2-methyl-4-(1-methyl(4-piperidyloxy))phenyl]azamethylene}-1,3-thiazolidin-4-one.

Effects of the Invention

The present invention provides novel thiazolidinone derivatives. Compounds provided by the present invention are useful as CDC7 protein kinase inhibitors. The CDC7 protein kinase is an enzyme that is closely involved in a cell cycle, particularly in the start of DNA replication. Therefore, the compound having a CDC7 protein kinase inhibitory action, which is provided by the present invention, can suppress cell proliferation. It has been confirmed that the thiazolidinone derivatives of the present invention exhibit a strong cell proliferation suppression action.

MODE FOR CARRYING OUT THE INVENTION

Figure 1:
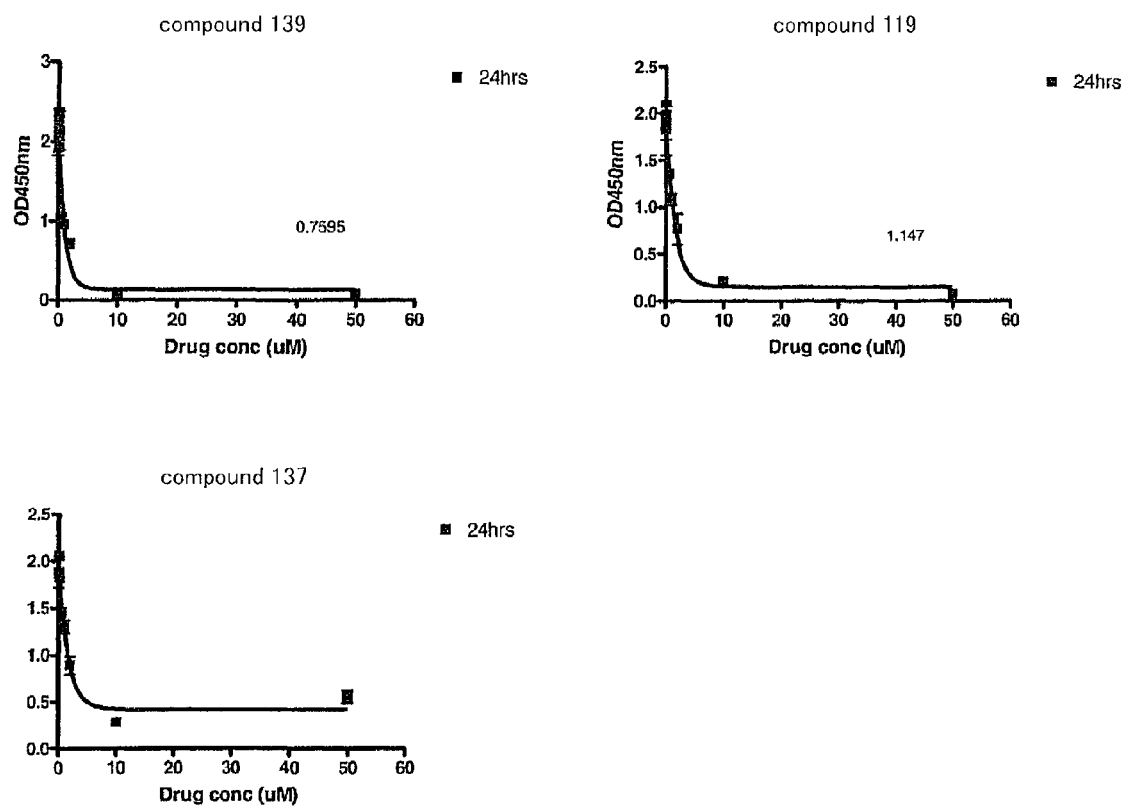
FIG. 1 is a graph showing results in which the inhibiting activity on cell proliferation was examined by incubation for 24 hours after adding the candidate compounds. The results for compounds 119, 137 and 139 are shown. In the graph, the vertical axis shows the absorbance at 450 nm, and the horizontal axis shows the final concentration (μM) of each compound.

Hereinafter, the meaning of terms, symbols, and the like, used in the present specification are described, and the present invention is described in detail.

The term "lower" used herein means a group having one to eight carbon atoms, preferably one to seven carbon atoms, more preferably one to six carbon atoms, and further preferably one to four carbon atoms, unless otherwise specified.

The term "may have a substituent" used herein means that one or two or more of any types of substituents may be included in any chemically possible positions, unless otherwise specified. When two or more types of substituents are present, they may be the same or may be different from each other.

The term "alkyl group" used herein denotes a monovalent group derived by removing any one hydrogen atom from aliphatic hydrocarbon that contains no heteroatom or no unsaturated carbon-carbon bond in the skeleton. Specific examples of the "lower alkyl group" include an alkyl group having one to six carbon atoms ($C_{1-6}$ alkyl group). More specific examples include a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group.

The term "lower alkylene group" used herein denotes a divalent group derived by further removing any one hydrogen atom from the above-defined "lower alkyl group."

Specific examples of the lower alkylene group include an alkylene group having one to six carbon atoms ($C_{1-6}$ alkylene group). More specific examples include a methylene group, an ethylene group, a trimethylene group, a propylene group, a tetramethylene group, a pentamethylene group, and a hexamethylene group.

The term "lower alkoxy group" used herein denotes an oxy group to which the above-defined "lower alkyl group" is bonded.

Specific examples of the "lower alkoxy group" include an alkoxy group having one to six carbon atoms ($C_{1-6}$ alkoxy group), and more specific examples include a methoxy group, an ethoxy group, a 1-propyloxy group, a 2-propyloxy group, 2-methyl-1-propyloxy group, a 2-methyl-2-propyloxy group, a 1-butyloxy group, a 2-butyloxy group, 1-pentyloxy group, a 2-pentyloxy group, a 3-pentyloxy group, a 2-methyl-1-butyloxy group, a 3-methyl-1-butyloxy group, a 2-methyl-2-butyloxy group, 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group.

The term "lower alkoxycarbonyl group" used herein denotes a carbonyl group to which the above-defined "lower alkoxy group" is bonded.

Specific examples of the "lower alkoxycarbonyl group" include a carbonyl group to which a $C_{1-6}$ alkoxy group is bonded ($C_{1-6}$ alkoxycarbonyl group). More specific examples include a methoxycarbonyl group, an ethoxycarbonyl group, a 1-propyloxycarbonyl group, and a 2-propyloxycarbonyl group.

The term "lower alkylcarbonylamino group" used herein denotes an amino group to which the carbonyl group, to which the above-defined "lower alkyl group" is bonded, is bonded.

Specific examples of the lower alkylcarbonylamino group include an alkylcarbonylamino group having 1 to 6 carbon atoms ($C_{1-6}$ alkylcarbonylamino group), and more specific examples include an acetylamino group, a propionylamino group, and a butyrylamino group.

The term "halogen" used herein denotes a fluorine atom, a chlorine atom, a bromine atom, or an iodine atom.

The term "lower alkyl group substituted by one to three halogen atoms" used herein denotes a lower alkyl group in which the same or different one to three "halogens" are bonded to the "lower alkyl group" (which is also referred to as a lower halogenated alkyl group).

Specific examples of the lower alkyl group substituted by one to three halogen atoms include a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, 2-bromoethyl group, a 2-chloroethyl group, a 2-fluoroethyl group, a 2-iodoethyl group, a pentafluoroethyl group, a 3-chloropropyl group, a 4-fluorobutyl group, a 6-iodohexyl group, and a 2,2-dibromoethyl group.

The term "alkyl group substituted by a hydroxyl group" used herein denotes a group in which any hydrogen atom in the above-defined "alkyl group" is substituted with a hydroxyl group.

Specific examples of such a group include a hydroxymethyl group, a 2-hydroxyethyl group, a 1-hydroxyethyl group, a 3-hydroxy propyl group, a 2-hydroxy propyl group, a 1-hydroxy propyl group, and a 4-hydroxy butyl group.

The term "cycloalkyl group" used herein denotes a monovalent group derived by removing any one hydrogen atom from a cyclic saturated hydrocarbon ring.

Specific examples of the cycloalkyl group include a cycloalkyl group having three to eight carbon atoms ($C_{3-8}$ cycloalkyl group), and more specific examples include a cyclopropyl group, a cyclobutyl group, a cyclopentyl group, a cyclohexyl group, a cycloheptyl group, and a cyclooctyl group.

The term "cycloalkylene group" used herein denotes a divalent group derived by further removing any one hydrogen atom from the above-defined "cycloalkyl group."

Specific examples of the cycloalkylene group include a cycloalkylene group having three to eight carbon atoms ($C_{3-8}$ cycloalkylene group), and more specific examples include a cyclopropylene group, a cyclobutylene group, a cyclopentylene group, and a cyclohexylene group.

The term "alkyl group substituted with a cycloalkyl group" used herein denotes a group in which any hydrogen atom in the above-identified "alkyl group" is replaced by the above-identified "cycloalkyl group".

Specific examples of such a group include a cyclopropyl methyl group, a cyclobutyl methyl group, a cyclopentyl methyl group, a cyclohexyl methyl group, a cycloheptyl methyl group, a cyclooctyl methyl group, a 1-cyclopropyl ethyl group, a 2-cyclopropyl ethyl group, a 1-cyclobutyl ethyl group, a 2-cyclobutyl ethyl group, a 1-cyclopentyl ethyl group, a 2-cyclopentyl ethyl group, a 1-cyclohexyl ethyl group, a 2-cyclohexyl ethyl group, a 1-cycloheptyl ethyl group, a 2-cycloheptyl ethyl group, a 1-cyclooctyl ethyl group, a 2-cyclooctyl ethyl group, and a cyclopropylpropyl group.

The term "aryl group" used herein denotes an aromatic hydrocarbon cyclic group.

Specific examples of the aryl group include an aryl group having six to ten carbon atoms ($C_{6-10}$ aryl group), and more specific examples include a phenyl group, a 1-naphthyl group, and a 2-naphthyl group.

The term "arylalkyl group" used herein denotes a group in which any hydrogen atom in the above-defined "alkyl group" is replaced by the above-defined "aryl group."

Specific examples of the arylalkyl group include a $C_{6-10}$ aryl $C_{1-5}$ alkyl group, and more specific examples include a benzyl group, a phenethyl group, and a 3-phenyl-1-propyl group.

The term "non-aromatic heterocyclic group" used herein denotes a monocyclic or polycyclic non-aromatic monovalent group that includes one to three heteroatoms (sulfur, oxygen and nitrogen atoms) in the atoms constituting a ring, and may include a double bond in the ring.

Specific examples of the non-aromatic heterocyclic group include five- to seven-membered ring non-aromatic heterocyclic group (5- to 7-membered non-aromatic heterocyclic group). More specific examples include a pyrrolidinyl group, a dihydropyrrolyl group, an imidazolidinyl group, a pyrazolidinyl group, an oxazolidinyl group, a thiazolidinyl group, a piperidyl group, a dihydropyridinyl group, a tetrahydropyridinyl group, a dihydropyrimidinyl group, a tetrahydropyrimidinyl group, a hexahydropyrimidinyl group, a 1,3-oxadinyl group, a pyranyl group, a dihydropyranyl group, a tetrahydropyranyl group, a tetrahydrofuranyl group, a dihydrofuranyl group, a piperazinyl group, a morpholinyl group, a thiomorpholinyl group, and a 1,3-dioxolanyl group.

The term "non-aromatic heterocyclic group substituted by a lower alkyl group" used herein denotes a group in which any one of the hydrogen atoms of the above-defined "non-aromatic heterocyclic group" is replaced by the above-defined "lower alkyl group."

Specific examples of such a "non-aromatic heterocyclic group substituted by a lower alkyl group" include a 1-methylpyrrolidin-2-yl group, a 1-methylpyrrolidin-3-yl group, a 1-methylimidazolidin-2-yl group, a 1-methylimidazolidin-3-yl group, a 1-methylpyrazolidin-3-yl group, a 1-methylpyrazolidin-4-yl group, a 1-methylpiperidin-2-yl group, a 1-methylpiperidin-3-yl group, a 1-methylpiperidin-4-yl group, a 4-methylpiperazin-1-yl group, a 1-methylpiperazin-4-yl group, a 1-ethylpyrrolidin-2-yl group, a 1-ethylpyrrolidin-3-yl group, a 1-ethylimidazolidin-2-yl group, a 1-ethylimidazolidin-3-yl group, a 1-ethylpyrazolidin-3-yl group, a 1-ethylpyrazolidin-4-yl group, a 1-ethylpiperidin-2-yl group, a 1-ethylpiperidin-3-yl group, a 1-ethylpiperidin-4-yl group, a 4-ethylpiperazin-1-yl group, and a 1-ethylpiperazin-4-yl group.

The term "alkyl group substituted by a non-aromatic heterocyclic group" used herein denotes a group in which any hydrogen atom in the above-defined "alkyl group" is replaced by the above-defined "non-aromatic heterocyclic group."

Specific examples of such a group include a morpholin-4-yl-methyl group, a 1-(morpholin-4-yl)ethyl group, a 2-(morpholin-4-yl)ethyl group, a pyrrolidin-1-ylmethyl group, a 1-(pyrrolidin-1-yl)ethyl group, a 2-(pyrrolidin-1-yl)ethyl group, a piperidin-1-ylmethyl group, a 1-(piperidin-1-yl)ethyl group, a 2-(piperidin-1-yl)ethyl group, and a 3-(piperidin-1-yl)propyl group.

The term "heteroaryl group" used herein denotes a monovalent group derived from an aromatic ring including one or a plurality of heteroatoms (sulfur, oxygen and nitrogen atoms) in the atoms constituting a ring. The ring can be monocyclic or polycyclic.

Specific examples of the heteroaryl group include five- to ten-membered ring heteroaryl group (5- to 10-membered heteroaryl group). More specific examples include a pyridyl group, a thiophenyl group, a furanyl group, a pyrrolyl group, an oxazolyl group, an isoxazolyl group, a thiazolyl group, a thiadiazolyl group, an isothiazolyl group, an imidazolyl group, a triazolyl group, a pyrazolyl group, a furazanyl group, a thiadiazolyl group, an oxadiazolyl group, a pyridazinyl group, a pyrimidinyl group, a pyrazinyl group, a triazinyl group, an indolyl group, an isoindolyl group, an indazolyl group, a chromenyl group, a quinolyl group, an isoquinolyl group, a cinnolinyl group, a quinazolinyl group, a naphthyridinyl group, a phthalazinyl group, a purinyl group, a pteridinyl group, a thienofuranyl group, an imidazothiazolyl group, a benzofuranyl group, a benzothiophenyl group, a benzooxazolyl group, a benzothiazolyl group, a benzothiadiazolyl group, a benzimidazolyl group, a benzotriazolyl group, an imidazopyridinyl group, a pyrrolopyridinyl group, and a pyrrolopyrimidinyl group.

The term "fused ring group" used herein denotes a monovalent group derived from a polycyclic compound in which "cycloalkane" and "arene" are fused, or a polycyclic compound in which "non-aromatic heterocycle" and "arene" are condensed.

The "cycloalkane" denotes a cyclic saturated hydrocarbon ring, and specifically includes cycloalkane having three to eight carbon atoms. More specific examples include cyclopropane, cyclobutane, cyclopentane, cyclohexane, cycloheptane, and cyclooctane.

The "arene" denotes an aromatic hydrocarbon ring, and specifically includes arene having six to ten carbon atoms. More specific examples include benzene, and naphthalene.

The "non-aromatic heterocycle" denotes a monocyclic or polycyclic non-aromatic heterocycle that includes one to three heteroatoms (sulfur, oxygen and nitrogen atoms) in the atoms constituting the ring and that may have a double bond in the ring. Specific examples include five- to seven-membered ring non-aromatic heterocycle. More specific examples include pyrrolidine, dihydropyrrole, imidazolidine, pyrazolidine, oxazolidine, thiazolidine, piperidine, dihydropyridine, tetrahydropyridine, dihydropyrimidine, tetrahydropyrimidine, hexahydropyrimidine, 1,3-oxazine, pyrane, dihydropyrane, tetrahydropyrane, tetrahydrofuran, dihydrofuran, piperazine, morpholine, thiomorpholine, and 1,3-dioxolane.

Specific examples of such a fused group includes an indanyl group, a 1,2,3,4-tetrahydronaphthyl group, a 3,4-dihydro-2H-1,4-benzooxadinyl group, a 3,4-dihydro-2H-1,4-benzothiazinyl group, a 1,3-benzodioxolyl group, a 2,3-dihydro-1,4-benzodioxinyl group, a chromanyl group, an isochromanyl group, a 3,4-dihydro-2H-1-benzothiopyranyl group, a 3,4-dihydro-1H-2-benzothiopyranyl group, an indolinyl group, an isoindolinyl group, a 1,2,3,4-tetrahydroquinolyl group, and a 1,2,3,4-tetrahydroisoquinolyl group.

The term "amino group substituted by one or two lower alkyl groups" used herein denotes an amino group in which a hydrogen atom(s) of the amino group is replaced by one or two of the "lower alkyl groups."

Specific examples of a mono alkylamino group, in which a hydrogen atom of the amino group is substituted by one lower alkyl group, include a methylamino group, an ethylamino group, and a propylamino group.

Specific examples of a dialkylamino group, in which hydrogen atoms of the amino group are replaced by two lower alkyl groups, include a dimethyl amino group, a diethyl amino group, a methylethylamino group, and a methylpropylamino group.

The term "amino group substituted by one lower alkyl group and one lower alkoxycarbonyl group" used herein denotes an amino group in which hydrogen atoms of the amino group are replaced by the above-defined "lower alkyl group" and the above-defined "lower alkoxycarbonyl group."

Specific examples of such a group include an N-methoxycarbonyl-N-methylamino group, an N-methoxycarbonyl-N-ethylamino group, an N-ethoxycarbonyl-N-methylamino group, and an N-methoxycarbonyl-N-ethylamino group.

The term "linear or branched lower alkyl group substituted by an amino group substituted by one or two lower alkyl groups" used herein denotes a group in which any hydrogen atom in the above-defined "lower alkyl group" is replaced by the above-defined "amino group substituted by one or two lower alkyl groups."

Specific examples of such a group include a methylaminomethyl group, a 1-(methylamino)ethyl group, a 2-(methylamino)ethyl group, a 1-(methylamino)propyl group, a 2-(methylamino)propyl group, a 3-(methylamino)propyl group, a dimethylaminomethyl group, a 1-(dimethylamino)ethyl group, a 2-(dimethylamino)ethyl group, a 1-(dimethylamino)propyl group, a 2-(dimethylamino)propyl group, a 3-(dimethylamino)propyl group, an ethylaminomethyl group, a 1-(ethylamino)ethyl group, a 2-(ethylamino)ethyl group, a 1-(ethylamino)propyl group, a 2-(ethylamino)propyl group, a 3-(ethylamino)propyl group, a diethylamino methyl group, a 1-(diethylamino)ethyl group, a 2-(diethylamino)ethyl group, a 1-(diethylamino)propyl group, a 2-(diethylamino)propyl group, and a 3-(diethylamino)propyl group.

The term "aminocarbonyl group substituted by one or two lower alkyl groups" used herein denotes a carbonyl group to which the above-defined "amino group substituted by one or two lower alkyl groups" is bonded.

Specific examples of such a group include a methylaminocarbonyl group, an ethylaminocarbonyl group, a propylaminocarbonyl group, a dimethylaminocarbonyl group, a diethylaminocarbonyl group, a methylethylaminocarbonyl group, and a methylpropylaminocarbonyl group.

The term "solvate" used herein denotes a group of molecules in which one or more types of solvent molecules and compounds are associated with each other in a stoichiometric manner or a non-stoichiometric manner.

Furthermore, the "hydrate" used herein denotes a solvate in which a solvent molecule is water.

The present invention relates to compounds represented by the following formula (I), geometric isomers and tautomers thereof, or salts, hydrates, or solvates thereof.

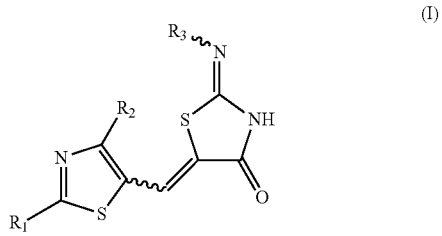

(I)

wherein $R_1$ is selected from the group consisting of a hydrogen atom, a linear or branched lower alkyl group, a halogen, a hydroxyl group, an amino group that may have a substituent, and a nonaromatic heterocyclic group that may have a substituent;

$R_2$ is a hydrogen atom, or a linear or branched lower alkyl group;

$R_3$ is selected from the group consisting of a linear or branched lower alkyl group, a cycloalkyl group that may have a substituent, an aryl group that may have a substituent, an arylalkyl group that may have a substituent, a nonaromatic heterocyclic group that may have a substituent, and a heteroaryl group that may have a substituent, or a fused ring group that may have a substituent; and a wavy line, independently for each occurrence, denotes trans (E-form), cis (Z-form) or a mixture (mixed product) thereof.

Hereinafter, preferable embodiments of the compound in accordance with the present invention are described.

When $R_1$ is a linear or branched lower alkyl group, $R_1$ can be selected from, for example, a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group. Among them, a t-butyl group is preferable.

When $R_1$ is a halogen, fluorine, chlorine, or bromine, is preferable.

When $R_1$ is an amino group that may have a substituent or a non-aromatic heterocyclic group that may have a substituent, $R_1$ can be selected from, for example, the group shown by the following (1) to (4):

(1) —$NR_{11}R_{12}$ (wherein $R_{11}$ is each independently selected from a hydrogen atom, a linear or branched lower alkyl group that may optionally be substituted by one to three halogen atoms or a cycloalkyl group, or a cycloalkyl group; or $R_{11}$ and $R_{12}$, together with the nitrogen atom to which they are attached, form a nonaromatic heterocyclic ring);

(2) —$N(R_{13})[(CH_2)_x—NR_{14}R_{15}]$ (wherein x is 2 to 4; $R_{13}$ is a hydrogen atom or a lower alkyl group; $R_{14}$ and $R_{15}$ are each a hydrogen atom or a lower alkyl group, or $R_{14}$ and $R_{15}$, together with the nitrogen atom to which they are attached, form a nonaromatic heterocyclic ring);

(3) —NHCO—$(CH_2)_y$—$NR_{16}R_{17}$ (wherein y is 0 to 3; $R_{16}$ and $R_{17}$ are each a hydrogen atom or a lower alkyl group that may optionally be substituted by an amino group substituted by one or two lower alkyl groups, or $R_{16}$ and $R_{17}$, together with the nitrogen atom to which they are attached, form a nonaromatic heterocyclic ring);

(4) —NHCO—$(CH_2)_n$—$R_{18}$ (wherein z is 0 to 3; $R_{18}$ is a lower alkyl group that may optionally be substituted by one to three halogen atoms, a lower alkoxyl group, a lower alkoxycarbonyl group, a carboxyl group, a cycloalkyl group, a non-aromatic heterocyclic group that may optionally be substituted by a lower alkyl group, or an aminocarbonyl group that may be substituted by one or two lower alkyl groups).

When $R_1$ is an amino group represented by a formula: —N—$R_{11}$—$R_{12}$, $R_{11}$ or $R_{12}$ can be selected from, for example, a hydrogen atom, a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, a 2,3-dimethyl-2-butyl group, a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, 2-bromoethyl group, a 2-chloroethyl group, a 2-fluoroethyl group, a 2-iodoethyl group, a pentafluoroethyl group, a 3-chloropropyl group, a 4-fluorobutyl group, a 6-iodohexyl group, 2,2-dibromoethyl group, a cyclopropyl group, a cyclobutyl group, a cyclopentyl group, a cyclohexyl group, a cycloheptyl group, a cyclooctyl group, a cyclopropyl methyl group, a cyclobutyl methyl group, a cyclopentyl methyl group, a cyclohexyl methyl group, a cycloheptyl methyl group, a cyclooctyl methyl group, a 1-cyclopropyl ethyl group, a 2-cyclopropyl ethyl group, a 1-cyclobutyl ethyl group, a 2-cyclobutyl ethyl group, a 1-cyclopentyl ethyl group, a 2-cyclopentyl ethyl group, a 1-cyclohexyl ethyl group, a 2-cyclohexyl ethyl group, a 1-cycloheptyl ethyl group, a 2-cycloheptyl ethyl group, a 1-cyclooctyl ethyl group, a 2-cyclooctyl ethyl group, and a cyclopropylpropyl group. In the present invention, a hydrogen atom, a methyl group, an ethyl group, an n-butyl group, a 2,2,2-trifluoroethyl group, a cyclopropyl group, a cyclopentyl group, a cyclohexyl group or a cyclopropyl methyl group, are preferable as $R_{11}$ or $R_{12}$ In other embodiments, $R_{11}$ and $R_{12}$ can form a nonaromatic heterocyclic group together with the nitrogen atom to which they are attached.

Such a non-aromatic heterocyclic group can be selected from, for example, pyrrolidinyl, dihydropyrrolyl, imidazolidinyl, pyrazolidinyl, oxazolidinyl, thiazolidinyl, piperidyl, dihydropyridinyl, tetrahydropyridinyl, dihydropyrimidinyl, tetrahydropyrimidinyl, hexahydropyrimidinyl, 1,3-oxadinyl, pyranyl, dihydropyranyl, tetrahydropyranyl, tetrahydrofuranyl, dihydrofuranyl, piperazinyl, morpholinyl, thiomorpholinyl, or 1,3-dioxolanyl. Among them, a 1-piperidyl group is preferable.

When $R_1$ is an amino group represented by a formula: —$N(R_{13})[(CH_2)_x—NR_{14}R_{15}]$, $R_{13}$ can be selected from, for example, a hydrogen atom, a methyl group, an ethyl group, a 1-propyl group or an isopropyl group. In the present invention, preferable $R_{13}$ is a hydrogen atom and a methyl group.

Either one of $R_{14}$ and $R_{15}$ is a lower alkyl group and the other is a hydrogen atom, or both of $R_{14}$ and $R_{15}$ are lower alkyl groups. Among them, the case that both of $R_{14}$ and $R_{15}$ are lower alkyl groups is preferable.

The alkyl moiety of $R_{14}$ and $R_{15}$ can be selected from, for example, a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group. Among them, a methyl group is preferable.

In other embodiments, $R_{14}$ and $R_{15}$ can form a nonaromatic heterocyclic group together with the nitrogen atom to which they are attached.

Such a non-aromatic heterocyclic group can be selected from, for example, pyrrolidinyl, dihydropyrrolyl, imidazolidinyl, pyrazolidinyl, oxazolidinyl, thiazolidinyl, piperidyl, dihydropyridinyl, tetrahydropyridinyl, dihydropyrimidinyl, tetrahydropyrimidinyl, hexahydropyrimidinyl, 1,3-oxadinyl, pyranyl, dihydropyranyl, tetrahydropyranyl, tetrahydrofuranyl, dihydrofuranyl, piperazinyl, morpholinyl, thiomorpholinyl, or 1,3-dioxolanyl. Among them, a 1-pyrrolidinyl group or a 4-morpholinyl group is preferable.

When $R_1$ is an amino group represented by a formula: —NHCO—$(CH_2)_y$—$NR_{16}R_{17}$, $R_{16}$ or $R_{17}$ can be selected from, for example, a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, a 2,3-dimethyl-2-butyl group, a methylaminomethyl group, a 1-(methylamino)ethyl group, a 2-(methylamino)ethyl group, a 1-(methylamino)propyl group, a 2-(methylamino)propyl group, a 3-(methylamino)propyl group, a dimethylamino group, a 1-(dimethylamino)ethyl group, a 2-(dimethylamino) ethyl group, a 1-(dimethylamino)propyl group, a 2-(dimethylamino)propyl group, a 3-(dimethylamino)propyl group, an ethylaminomethyl group, a 1-(ethylamino)ethyl group, a 2-(ethylamino)ethyl group, a 1-(ethylamino)propyl group, a 2-(ethylamino)propyl group, a 3-(ethylamino)propyl group, a diethylaminomethyl group, a 1-(diethylamino)ethyl group, a 2-(diethylamino)ethyl group, a 1-(diethylamino)propyl group, a 2-(diethylamino)propyl group, or a 3-(diethylamino) propyl group. Among them, a hydrogen atom, a methyl group or a 2-(dimethylamino)ethyl group is preferable.

In other embodiments, $R_{16}$ and $R_{17}$ can form a nonaromatic heterocyclic group that may be substituted by a lower alkyl group, together with the nitrogen atom to which they are attached.

Such a non-aromatic heterocyclic group can be selected from, for example, pyrrolidinyl, dihydropyrrolyl, imidazolidinyl, pyrazolidinyl, oxazolidinyl, thiazolidinyl, piperidyl, dihydropyridinyl, tetrahydropyridinyl, dihydropyrimidinyl, tetrahydropyrimidinyl, hexahydropyrimidinyl, 1,3-oxadinyl, pyranyl, dihydropyranyl, tetrahydropyranyl, tetrahydrofuranyl, dihydrofuranyl, piperazinyl, morpholinyl, thiomorpholinyl, or 1,3-dioxolanyl.

Furthermore, these groups can be substituted by a lower alkyl group. These non-aromatic heterocyclic groups substituted by a lower alkyl group can be selected from, for example, a 1-methylpyrrolidin-2-yl group, a 1-methylpyrrolidin-3-yl group, a 1-methylimidazolidin-2-yl group, a 1-methylimidazolidin-3-yl group, a 1-methylpyrazolidin-3-yl group, a 1-methylpyrazolidin-4-yl group, a 1-methylpiperidin-2-yl group, a 1-methylpiperidin-3-yl group, a 1-methylpiperidin-4-yl group, 4-methylpiperazin-1-yl group, a 1-methylpiperazin-4-yl group, a 1-ethylpyrrolidin-2-yl group, a 1-ethylpyrrolidin-3-yl group, a 1-ethylimidazolidin-2-yl group, a 1-ethylimidazolidin-3-yl group, a 1-ethylpyrazolidin-3-yl group, a 1-ethylpyrazolidin-4-yl group, a 1-ethylpiperidin-2-yl group, a 1-ethylpiperidin-3-yl group, 1-ethylpiperidin-4-yl group, a 4-ethylpiperazin-1-yl group, or a 1-ethylpiperazin-4-yl group. Among them, a 4-methyl piperazin-1-yl group is preferable.

When $R_1$ is an amino group represented by a formula: —NHCO—$(CH_2)_z$—$NR_{18}$, $R_{18}$ can be selected from, for example, a lower alkyl group that may optionally be substituted by one to three halogen atoms, a carboxyl group, a cycloalkyl group, a nonaromatic heterocyclic group that may optionally be substituted by a lower alkyl group, or a lower alkoxycarbonyl group or a lower alkoxy group.

When $R_{18}$ is a lower alkyl group that may optionally be substituted by one to three halogen atoms, $R_{18}$ can be selected from, for example, a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, a 2,3-dimethyl-2-butyl group, trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, 2-bromoethyl group, a 2-chloroethyl group, a 2-fluoroethyl group, a 2-iodoethyl group, a pentafluoroethyl group, a 3-chloropropyl group, a 4-fluorobutyl group, a 6-iodohexyl group, or a 2,2-dibromoethyl group. Among them, a methyl group or a 2,2,2-trifluoroethyl group is preferable.

When $R_{18}$ is a cycloalkyl group, $R_{18}$ can be selected from, for example, a cyclopropyl group, a cyclobutyl group, a cyclopentyl group, a cyclohexyl group, a cycloheptyl group, or a cyclooctyl group. Among them, a cyclopropyl group is preferable.

When $R_{18}$ is a nonaromatic heterocyclic group that may optionally be substituted by a lower alkyl group, $R_{18}$ can be selected from, for example, pyrrolidinyl, dihydropyrrolyl, imidazolidinyl, pyrazolidinyl, oxazolidinyl, thiazolidinyl, piperidyl, dihydropyridinyl, tetrahydropyridinyl, dihydropyrimidinyl, tetrahydropyrimidinyl, hexahydropyrimidinyl, 1,3-oxadinyl, pyranyl, dihydropyranyl, tetrahydropyranyl, tetrahydrofuranyl, dihydrofuranyl, piperazinyl, morpholinyl, thiomorpholinyl, 1,3-dioxolanyl, 1-methylpyrrolidin-2-yl group, a 1-methylpyrrolidin-3-yl group, a 1-methylimidazolidin-2-yl group, a 1-methylimidazolidin-3-yl group, a 1-methylpyrazolidin-3-yl group, a 1-methylpyrazolidin-4-yl group, a 1-methylpiperidin-2-yl group, a 1-methylpiperidin-3-yl group, a 1-methylpiperidin-4-yl group, 4-methylpiperazin-1-yl group, a 1-methylpiperazin-4-yl group, a 1-ethylpyrrolidin-2-yl group, a 1-ethylpyrrolidin-3-yl group, a 1-ethylimidazolidin-2-yl group, a 1-ethylimidazolidin-3-yl group, a 1-ethylpyrazolidin-3-yl group, a 1-ethylpyrazolidin-4-yl group, a 1-ethylpiperidin-2-yl group, a 1-ethylpiperidin-3-yl group, 1-ethylpiperidin-4-yl group, a 4-ethylpiperazin-1-yl group, or a 1-ethylpiperazin-4-yl group. Among them, a 1-methylpiperidin-4-yl group is preferable.

When $R_{18}$ is a lower alkoxycarbonyl group, $R_{18}$ can be selected from, for example, a methoxycarbonyl group, an ethoxycarbonyl group, a 1-propyloxycarbonyl group, or a 2-propyloxycarbonyl group. Among them, a methoxycarbonyl group is preferable.

When $R_{18}$ is a lower alkoxy group, $R_{18}$ can be selected from, for example, a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, or a 2,3-dimethyl-2-butyloxy group. Among them, a methoxy group or an ethoxy group is preferable.

When $R_{18}$ is an aminocarbonyl group that may optionally be substituted by one or two lower alkyl groups, $R_{18}$ can be selected from, for example, a methylaminocarbonyl group, an ethylaminocarbonyl group, a propylaminocarbonyl group, a dimethylaminocarbonyl group, a diethylaminocarbonyl group, a methylethylaminocarbonyl group, or a methylpropylaminocarbonyl group. Among them, a methylaminocarbonyl group or a dimethylaminocarbonyl group is preferred.

When $R_2$ is a linear or branched lower alkyl group, $R_2$ can be selected from, for example, a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, or a 2,3-dimethyl-2-butyl group. Among them, an n-butyl group is preferable.

When $R_3$ is a linear or branched lower alkyl group, $R_3$ can be selected from, for example, a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, or a 2,3-dimethyl-2-butyl group. Among them, an n-butyl group is preferable.

When $R_3$ is a cycloalkyl group that may have a substituent, such a cycloalkyl group can be selected from, for example, a cyclopropyl group, a cyclobutyl group, a cyclopentyl group, a cyclohexyl group, a cycloheptyl group, or a cyclooctyl group.

Additionally, the substituent of a cycloalkyl group can be selected from, for example, a lower alkyl group, a lower alkoxy group, a halogen, or a hydroxyl group.

When $R_3$ is an arylalkyl group that may have a substituent, such an arylalkyl group can be selected from, for example, a benzyl group, a phenethyl group, or a 3-phenyl-1-propyl group. Among them, a benzyl group is preferable.

Furthermore, the arylalkyl group can be substituted by more than one substituent at its aryl moiety or an alkyl moiety, or both of the aryl moiety and the alkyl moiety.

The substituents in the aryl moiety can be selected from, for example, fluorine, chlorine, bromine, iodine, a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, a 2,3-dimethyl-2-butyl group, a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, 2-bromoethyl group, a 2-chloroethyl group, a 2-fluoroethyl group, a 2-iodoethyl group, a pentafluoroethyl group, a 3-chloropropyl group, a 4-fluorobutyl group, a 6-iodohexyl group, 2,2-dibromoethyl group, a methoxy group, an ethoxy group, a 1-propyloxy group, 2-propyloxy group, 2-methyl-1-propyloxy group, a 2-methyl-2-propyloxy group, a 1-butyloxy group, a 2-butyloxy group, 1-pentyloxy group, a 2-pentyloxy group, a 3-pentyloxy group, a 2-methyl-1-butyloxy group, a 3-methyl-1-butyloxy group, a 2-methyl-2-butyloxy group, 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group. Among them, chlorine, fluorine, bromine, a trifluoromethyl group, or a methoxy group is preferable.

The substituents in the alkyl moiety can be selected from, for example, a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, or a 2,3-dimethyl-2-butyl group. Among them, a methyl group is preferable.

When $R_3$ is a non-aromatic heterocyclic group that may have a substituent, the non-aromatic heterocyclic group can be selected from, for example, pyrrolidinyl, dihydropyrrolyl, imidazolidinyl, pyrazolidinyl, oxazolidinyl, thiazolidinyl, piperidyl, dihydropyridinyl, tetrahydropyridinyl, dihydropyrimidinyl, tetrahydropyrimidinyl, hexahydropyrimidinyl, 1,3-oxadinyl, pyranyl, dihydropyranyl, tetrahydropyranyl, tetrahydrofuranyl, dihydrofuranyl, piperazinyl, morpholinyl, thiomorpholinyl, or 1,3-dioxolanyl.

Furthermore, the substituents of the non-aromatic heterocyclic group can be selected from a lower alkyl group, a cycloalkyl group, a lower alkoxy group, halogen, a hydroxyl group, or the like.

When $R_3$ is an aryl group or a heteroaryl group which may have a substituent, the aryl group can be selected from, for example, a phenyl group, and a naphthyl group. Among them, a phenyl group is preferable. Furthermore, the heteroaryl group can be selected from, for example, a pyridyl group, a thiophenyl group, a furanyl group, a pyrrolyl group, an oxazolyl group, an isoxazolyl group, a thiazolyl group, a thiadiazolyl group, an isothiazolyl group, an imidazolyl group, a triazolyl group, a pyrazolyl group, a furazanyl group, a thiadiazolyl group, an oxadiazolyl group, a pyridazinyl group, a pyrimidinyl group, a pyrazinyl group, a triazinyl group, an indolyl group, an isoindolyl group, an indazolyl group, a chromenyl group, a quinolyl group, an isoquinolyl group, a cinnolinyl group, a quinazolinyl group, a naphthyridinyl group, a phthalazinyl group, a purinyl group, a pteridinyl group, a thienofuranyl group, an imidazo thiazolyl group, a benzofuranyl group, a benzothio phenyl group, a benzooxazolyl group, a benzothiazolyl group, a benzothiadiazolyl group, a benzimidazolyl group, a benzotriazolyl group, an imidazopyridinyl group, a pyrrolopyridinyl group, or a pyrrolopyrimidinyl group. Among them, an indolyl group (for example, an indole-5-yl group, an indole-6-yl group, and an indole-7-yl group), an indazolyl group (for example, a 1H-indazole-6-yl group), a quinolyl group (for example, a quinolin-6-yl group), a benzimidazolyl group (for example, a benzimidazole-2-yl group, a benzimidazole-5-yl group), or a benzotriazolyl group (for example, a benzotriazole-5-yl group) is preferable.

Substituents of the aryl group or the heteroaryl group which may have a substituent can be independently selected from, for example, one to three groups from the following group B.

Group B:
a linear or branched lower alkyl group which may be substituted with a group selected from the group consisting of one to three halogen atoms, a hydroxyl group, an amino group substituted by one or two lower alkyl groups and a non-aromatic heterocyclic group;
a lower alkoxy group;
a hydroxyl group;
halogen;
a nitro group;
an amino group that may be substituted by one or two lower alkyl groups;
a lower alkylcarbonylamino group;
a group represented by a formula: —$(CH_2)_k$COOH (wherein k is 0 to 2);
a group represented by a formula: —O—$R_{31}$—$R_{32}$, wherein $R_{31}$ is a single bond, a lower alkylene group, or a cycloalkylene group; and $R_{32}$ is a group selected from a hydroxyl group; a carboxyl group; a lower alkoxy group; a lower alkoxycarbonyl group; two lower alkyl groups, or an amino group substituted by one lower alkyl group and one lower alkoxy carbonyl group; and a non-aromatic heterocyclic group that may be substituted by a lower alkyl group; and
a group represented by a formula: —CON($R_{33}$)[$(CH_2)_m$—$R_{34}$], wherein m is 0 to 2, $R_{33}$ is a hydrogen atom or a lower alkyl group, and $R_{34}$ is an amino group substituted by one or two lower alkyl groups.

When the substituent of the aryl group or the heteroaryl group which may have a substituent is a linear or branched lower alkyl group that may be substituted by a group selected from the group consisting of one to three halogen atoms, a hydroxyl group, an amino group substituted by one or two lower alkyl groups and a non-aromatic heterocyclic group, such a substituent can be selected from, for example, a methyl group, an ethyl group, a 1-propyl group, an isopropyl group, an n-butyl group, an s-butyl group, a t-butyl group, an isobutyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, a 2,3-dimethyl-2-butyl group, a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, a 2-bromoethyl group, a 2-chloroethyl group, a 2-fluoroethyl group, 2-iodoethyl group, a pentafluoroethyl group, a 3-chloropropyl group, a 4-fluorobutyl group, a 6-iodohexyl group, a 2,2-dibromoethyl group, a methylamino methyl group, a 1-(methylamino)ethyl group, a 2-(methylamino)ethyl group, a 1-(methylamino) propyl group, a 2-(methylamino)propyl group, a 3-(methylamino)propyl group, a dimethylamino methyl group, a 1-(dimethylamino)ethyl group, a 2-(dimethylamino)ethyl group, a 1-(dimethylamino)propyl group, a 2-(dimethylamino)propyl group, a 3-(dimethylamino)propyl group, an ethylamino methyl group, a 1-(ethylamino)ethyl group, a 2-(ethylamino)ethyl group, a 1-(ethylamino)propyl group, a 2-(ethylamino)propyl group, a 3-(ethylamino)propyl group, a diethylamino methyl group, a 1-(diethylamino)ethyl group, a 2-(diethylamino)ethyl group, a 1-(diethylamino)propyl group, a 2-(diethylamino)propyl group, a 3-(diethylamino) propyl group, a hydroxy methyl group, a 2-hydroxy ethyl group, a 1-hydroxy ethyl group, a 3-hydroxy propyl group, a 2-hydroxy propyl group, a 1-hydroxy propyl group, a 4-hydroxy butyl group, a morpholin-4-ylmethyl group, a 1-(morpholin-4-yl)ethyl group, a 2-(morpholin-4-yl)ethyl group, a pyrrolidin-1-ylmethyl group, a 1-(pyrrolidin-1-yl)ethyl group, a 2-(pyrrolidin-1-yl)ethyl group, a piperidin-1-ylmethyl group, a 1-(piperidin-1-yl)ethyl group, a 2-(piperidin-1-yl)ethyl group, or a 3-(piperidin-1-yl)propyl group. Among them, a methyl group, an ethyl group, an isopropyl group, a trifluoromethyl group, a 2-(dimethylamino)ethyl group, a 3-(dimethylamino)propyl group, a 2-(morpholin-4-yl)ethyl group, a 2-(pyrrolidin-1-yl)ethyl group, a 2-(piperidin-1-yl) ethyl group, a 3-(piperidin-1-yl)propyl group, and a hydroxy methyl group are preferable.

When the substituent of the aryl group or the heteroaryl group which may have a substituent is a lower alkoxy group, such a substituent can be selected from, for example, a methoxy group, an ethoxy group, a 1-propyloxy group, a 2-propyloxy group, 2-methyl-1-propyloxy group, a 2-methyl-2-propyloxy group, a 1-butyloxy group, a 2-butyloxy group, 1-pentyloxy group, a 2-pentyloxy group, a 3-pentyloxy group, a 2-methyl-1-butyloxy group, a 3-methyl-1-butyloxy group, a 2-methyl-2-butyloxy group, 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1- butyloxy group, a 2,2-dimethyl-1-butyloxy group, a 2-ethyl-1-butyloxy group, a 3,3-dimethyl-2-butyloxy group, and a 2,3-dimethyl-2-butyloxy group. Among them, a methoxy group is preferable.

When the substituent of the aryl group or the heteroaryl group which may have a substituent is halogen, such a substituent is preferably fluorine or chlorine.

When the substituent of the aryl group or the heteroaryl group which may have a substituent is an amino group that may be substituted with one or two lower alkyl groups, such a substituent can be selected from, for example, an amino group, a methylamino group, an ethylamino group, a propylamino group, a dimethylamino group, a diethylamino group, a methylethylamino group, and a methylpropylamino group. Among them, a methylamino group or a dimethylamino group is preferable.

When the substituent of the aryl group or the heteroaryl group which may have a substituent is a lower alkylcarbonylamino group, such a substituent can be selected from, for example, an acetylamino group, a propionylamino group, and a butyrylamino group. Among them, an acetylamino group is preferable.

When the substituent of the aryl group or the heteroaryl group which may have a substituent is a group represented by a formula: —$(CH_2)_k$COOH, wherein k is 0 to 2, such a substituent can be selected from, for example, a carboxyl group (k=0), a carboxy methyl group (k=1), and a carboxyethyl group (k=2). Among them, a carboxyl group or a carboxy methyl group is preferable.

When the substituent of the aryl group or the heteroaryl group which may have a substituent is a group represented by a formula: —O—$R_{31}$—$R_{32}$, wherein $R_{31}$ is a single bond, a lower alkylene group or a cycloalkyne group; $R_{32}$ is a group selected from a hydroxyl group; a carboxyl group; a lower alkoxy group; a lower alkoxycarbonyl group; an amino group substituted with two lower alkyl groups or one lower alkyl group and one lower alkoxy carbonyl group; and a non-aromatic heterocyclic group that may be substituted with lower alkyl group, $R_{11}$ can be selected from, for example, a single bond, a methylene group, an ethylene group, a trimethylene group, a propylene group, a tetramethylene group, a pentamethylene group, a hexamethylene group, a cyclopropylene group, a cyclobutylene group (for example, 1,1-cyclobutylene, 1,2-cyclobutylene), a cyclopentylene group (for example, 1,1-cyclopentylene, 1,2-cyclopentylene, 1,3-cyclopentylene), and a cyclohexylene group (for example, 1,2-cyclohexylene, 1,3-cyclohexylene, 1,4-cycloxylene). Among them, a single bond, an ethylene group, a trimethylene group or a cyclohexylene group is preferable.

Furthermore, $R_{32}$ can be selected from, for example, a hydroxyl group, a carboxyl group, a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, a 2,3-dimethyl-2-butyloxy group, a methoxy carbonyl group, an ethoxy carbonyl group, a 1-propyloxy carbonyl group, a 2-propyloxy carbonyl group, a dimethyl amino group, a diethyl amino group, a methylethyl amino group, a methylpropyl amino group, an N-methoxycarbonyl-N-methylamino group, an N-methoxycarbonyl-N-ethylamino group, an N-ethoxycarbonyl-N-methylamino group, an N-methoxycarbonyl-N-ethylamino group, a pyrrolidinyl group, a dihydropyrrolyl group, an imidazolidinyl group, a pyrazolidinyl group, an oxazolidinyl group, a thiazolidinyl group, a piperidyl group, a dihydropyridinyl group, a tetrahydropyridinyl group, a dihydropyrimidinyl group, a tetrahydropyrimidinyl group, a hexahydropyrimidinyl group, a 1,3-oxadinyl group, a pyranyl group, a dihydropyranyl group, a tetrahydropyranyl group, a tetrahydrofuranyl group, a dihydrofuranyl group, a piperazinyl group, a morpholinyl group, a thiomorpholinyl group, 1,3-dioxolanyl group, a 1-methylpyrrolidin-2-yl group, a 1-methylpyrrolidin-3-yl group, a 1-methylimidazolidin-2-yl group, a 1-methylimidazolidin-3-yl group, a 1-methylpyrazolidin-3-yl group, a 1-methylpyrazolidin-4-yl group, a 1-methylpiperidin-2-yl group, a 1-methylpiperidin-3-yl group, a 1-methylpiperidin-4-yl group, 4-methylpiperazin-1-yl group, a 1-methylpiperazin-4-yl group, a 1-ethylpyrrolidin-2-yl group, a 1-ethylpyrrolidin-3-yl group, a 1-ethylimidazolidin-2-yl group, a 1-ethylimidazolidin-3-yl group, a 1-ethylpyrazolidin-3-yl group, a 1-ethylpyrazolidin-4-yl group, a 1-ethylpiperidin-2-yl group, a 1-ethylpiperidin-3-yl group, 1-ethylpiperidin-4-yl group, a 4-ethylpiperazin-1-yl group, or a 1-ethylpiperazin-4-yl group. Among them, a hydroxyl group, a carboxyl group, a methoxy group, an ethoxy carbonyl group, a dimethyl amino group, a diethyl amino group, an N-methoxycarbonyl-N-methylamino group, a pyrrolidinyl group (for example, pyrrolidin-1-yl group), a piperidinyl group (for example, piperidin-1-yl group), a morpholinyl group (for example, a morpholin-4-yl group), a 1-methylpyrrolidin-3-yl group, a 1-methyl piperidin-4-yl group, or a 4-methyl piperidin-1-yl group is preferable.

When the substituent of the aryl group or the heteroaryl group which may have a substituent is a group represented by a formula: —CON($R_{33}$)[($CH_2)_m$—$R_{34}$], wherein m is 0 to 2, $R_{13}$ is a hydrogen atom or a lower alkyl group, and $R_{34}$ is an amino group that is substituted by one or two lower alkyl groups, $R_{33}$ can be selected from, for example, a hydrogen atom, a methyl group, an ethyl group, 1-propyl group, an isopropyl group, an n-butyl group, an s-butyl group, a t-butyl group, and an isobutyl group. Among them, a hydrogen atom or a methyl group is preferable.

Furthermore, $R_{34}$ can be selected from, for example, a methyl amino group, an ethyl amino group, a propyl amino group, a dimethyl amino group, a diethyl amino group, a methylethylamino group, and a methyl propyl amino group. Among them, a dimethyl amino group is preferable.

When $R_3$ is a fused ring group of a cycloalkyl group or a non-aromatic heterocyclic group and an aryl group, such a fused ring group can be selected from, for example, an indanyl group, a 1,2,3,4-tetrahydronaphthyl group, a 3,4-dihydro-2H-1,4-benzooxadinyl group, a 3,4-dihydro-2H-1,4-benzothiazinyl group, a 1,3-benzodioxolyl group, a 2,3-dihydro-1,4-benzodioxinyl group, a chromanyl group, an isochromanyl group, a 3,4-dihydro-2H-1-benzothiopyranyl group, a 3,4-dihydro-1H-2-benzothiopyranyl group, an indolinyl group, an isoindolinyl group, a 1,2,3,4-tetrahydroquinolyl group, and a 1,2,3,4-tetrahydroisoquinolyl group. Among them, an indanyl group (for example, an indan-4-yl group, an indan-1-yl group), or a 1,3-benzodioxolyl group (for example, a 1,3-benzodioxole-5-yl group) is preferable.

Furthermore, the fused ring group may have a substituent. The substituent can be specifically selected from a lower alkyl group, a cycloalkyl group, a lower alkoxy group, halogen, a hydroxyl group, or the like.

In the formula (I), a wavy line, independently for each occurrence, denotes trans (E-form), cis (Z-form) or a mixture (mixed product) thereof. Each isomer indicated by the wavy line can be specifically represented by the following formulae (I-I) to (I-IV).

The isomers represented by the formulae (I-I) to (I-IV) can be mutually converted into each other in a solvent in the presence of, for example, an acid or a base. In the present specification, the "mixture of cis and trans" or the "mixture of an E-form and a Z-form" means that such states are included. Although depending upon the isolation method, when isolation is carried out, the isomer can generally have geometric isomerism represented by the formula (I-I).

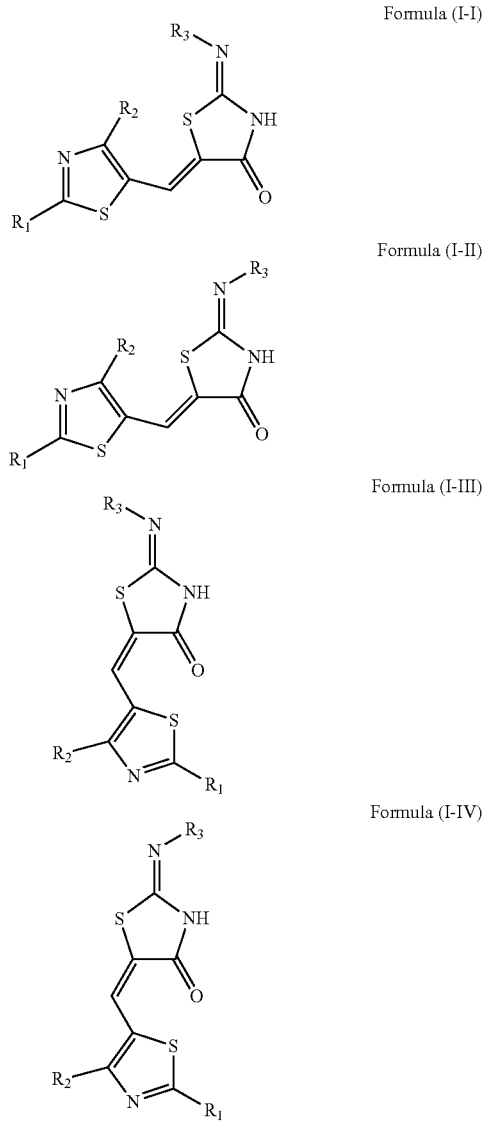

Formula (I-I)

Formula (I-II)

Formula (I-III)

Formula (I-IV)

The compound of the present invention may have an isomer, for example, depending upon the type of substituent. The present specification may describe a chemical structure of only one embodiment in such isomers. However, the present invention includes all types of isomers (geometric isomer, optical isomer, stereoisomer, tautomer, and the like) having chemical structures that can be generated, and also includes an isomer separated therefrom, or mixtures of the isomers.

Various isomers can also be purified and isolated by using usual separation methods, for example, recrystallization, a diastereomeric salt method, an enzyme fractionation method, various types of chromatographies (for example, thin-layer chromatography, column chromatography, and the like). Alternatively, a mixture of isomers can be employed as long as the intended actions are maintained.

Furthermore, the compound of the present invention may form a salt. Any salts may be included in the present invention as long as they are pharmaceutically acceptable salts.

Specific examples of such salts include an inorganic acid salt, an organic acid salt, an inorganic base salt, an organic base salt, an acidic or basic amino acid salt. Among them, examples of the inorganic acid salt include hydrochloride, hydrobromate, sulfate, nitrate, and phosphate. On the other hand, examples of the organic acid salt include acetate, succinate, fumarate, maleate, tartrate, citrate, lactate, stearate, benzoate, methanesulfonate, and p-toluene sulfonate.

Furthermore, the compound of the present invention may be a pharmaceutically acceptable prodrug. The pharmaceutically acceptable prodrug in the present specification is a derivative of the compound of the present invention that has been modified by a group capable of chemically or metabolically degrading the compound of the present invention. The prodrug is a derivative that is demodified after it is given to a living body, generates an original compound, and exhibits the original drug effect.

Furthermore, various types of hydrates or solvates of the compounds and pharmaceutically acceptable salts of the present invention may be included in the present invention.

Furthermore, the compounds in accordance with the present invention may have polymorphisms. Substances of such polymorphisms may be included in the present invention.

Typical Production Process of Compounds of the Present Invention

The compound represented by the formula (I) in accordance with the present invention can be produced by applying various known organic synthesis reactions. At this time, depending upon the type of functional group, the functional group may be substituted with an appropriate protecting group in the stage of raw materials or intermediate products. For selection, introduction and deprotection of such a protecting group, for example, the method described in "Greene's Protective Groups in Organic Synthesis (the 4th edition, Wiley-Interscience, 2007)" can be employed. In the production of the compounds of the present invention, commercially available compounds, or compounds produced in usual methods can be used for compounds of raw materials.

(The Production Process 1-1)

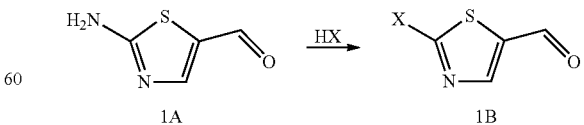

Wherein X is a halogen.

The production process 1-1 is the method for obtaining the compound shown by formula 1A by reacting the compound shown by formula 1A with an aqueous halogen acid (HX).

The reaction is carried out by stirring at −78° C. to room temperature, generally for 10 minutes to 24 hours, using an equal amount of the compound shown by formula 1A and the HX, or an excessive amount of either one of them. As the reaction solvent, protic polar solvent such as water, ethanol, methanol, propanol is preferably used, but is not limited thereto. In some case, it is preferable to carry out the reaction in the presence of catalyst such as $NaNO_2$, copper halide (for example, when X is Br, it is CuBr).

(The Production Process 1-2)

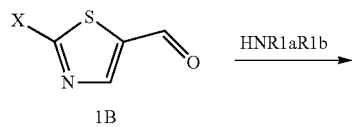

Wherein X is a halogen; $R_{1a}$ is $R_{11}$ or $R_{13}$; $R_{1b}$ is $R_{12}$ when $R_{1b}$ is $R_{11}$, or $R_{1b}$ is $—(CH_2)_x—NR_{14}R_{15}$ when $R_{1b}$ is $R_{13}$; where x, $R_{11}$, $R_{12}$, $R_{13}$, $R_{14}$ and $R_{15}$ are the same as the x, $R_{11}$, $R_{12}$, $R_{13}$, $R_{14}$ and $R_{15}$ mentioned above.

The production process 1-2 is the method for obtaining the compound shown by formula 1C by reacting the compound shown by formula 1B with $HNR_{1a}R_{1b}$. The reaction is carried out by stirring at in the 0° C. to heated reflux temperature, generally for 10 minutes to 24 hours, using an equal amount of the compound shown by formula 1B and the $HNR_{1a}R_{1b}$, or an excessive amount of either one of them. As the reaction solvent, aromatic hydrocarbons (for example, toluene, xylene), ethers (for example, diethylether, THF, dioxane), halogenated hydrocarbon (for example, dichloromethane, chloroform), N,N-dimethylformamide(DMF) or dimethylsulfoxide(DMSO) can be used. As the base, organic base (for example, triethylamine, diisopropylethylamine, n-butyllithium) or inorganic base (for example, sodium carbonate, potassium carbonate, sodium hydride) can be used.

(The Production Process 1-3)

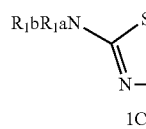

Wherein L is an elimination group; $R_{1c}$ is $—(CH_2)_y—NR_{16}R_{17}$ or $—(CH_2)_z—R_{18}$; where y=1 to 3, z, $R_{16}$, $R_{17}$ and $R_{18}$ are the same as the z, $R_{16}$, $R_{17}$ and $R_{18}$ mentioned above.

The production process 1-3 is the method for obtaining the compound shown by formula 1D by reacting the compound shown by formula 1A with $R_{1c}COL$. The elimination group includes, for example, a halogen, a methanesulfonyloxy group, p-toluenesulfonyloxy group. The reaction is carried out by stirring at 0° C. to heated reflux temperature, generally for 10 minutes to 24 hours, using an equal amount of the compound shown by formula 1A and $R_{1c}COL$, or an excessive amount of either one of them. As the reaction solvent, aromatic hydrocarbons (for example, toluene, xylene), ethers (for example, diethylether, THF, dioxane), halogenated hydrocarbon (for example, dichloromethane, chloroform), N,N-dimethylformamide (DMF) or dimethylsulfoxide (DMSO) can be used. In some case, it is preferable that this reaction is carried out in the presence of carbodiimides such as dicyclocarbodiimide (DCC), diisopropylcarbodiimide (DIC), 1-ethyl-3-(3-dimethylaminopropyl)carbodiimide hydrochloride (EDC).

(The Production Process 1-4)

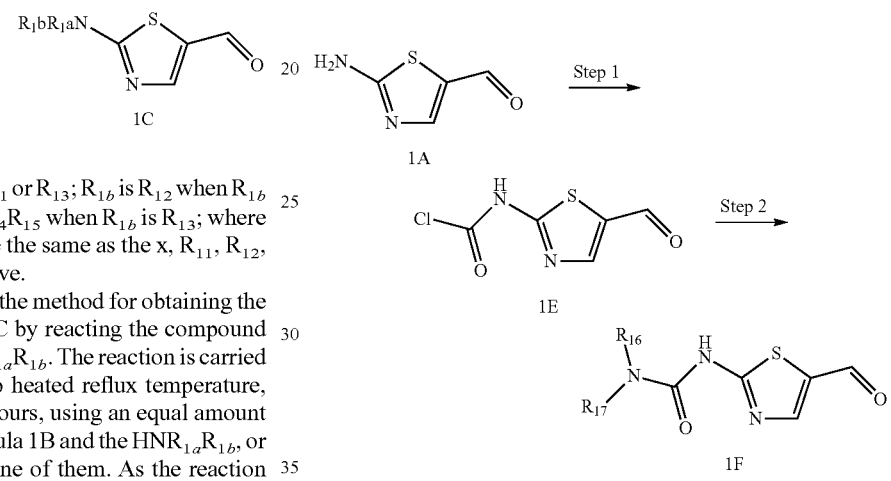

wherein $R_{16}$ and $R_{17}$ is the same as $R_{16}$ and $R_{17}$ mentioned above.

The first process of the production process 1-4 is the method for obtaining the compound shown by formula 1E by reacting the compound shown by formula 1A with triphosgene or phosgene. The reaction is carried out by stirring at 0° C. to heated reflux temperature, generally for 10 minutes to 24 hours, using an equal amount of the compound shown by formula 1A and triphosgene or phosgene, or an excessive amount of either one of them. As the reaction solvent, aromatic hydrocarbons (for example, toluene, xylene), ethers (for example, diethylether, THF, dioxane), halogenated hydrocarbon (for example, dichloromethane, chloroform), N,N-dimethylformamide (DMF) or dimethylsulfoxide (DMSO) can be used.

The second process of the production process 1-4 is the method for obtaining the compound shown by formula 1F by reacting the compound shown by formula 1E with $R_{16}R_{17}NH$. The reaction is carried out by stirring at 0° C. to heated reflux temperature, generally for 10 minutes to 24 hours, using an equal amount of the compound shown by formula 1A and $R_{16}R_{17}NH$, or an excessive amount of either one of them. As the reaction solvent, aromatic hydrocarbons (for example, toluene, xylene), ethers (for example, diethylether, THF, dioxane), halogenated hydrocarbon (for example, dichloromethane, chloroform), N,N-dimethylformamide (DMF) or dimethylsulfoxide (DMSO) can be used.

(The Production Process 2-1)

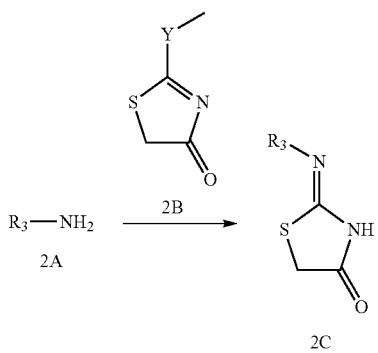

Wherein Y is an oxygen or a sulfur; R₃ is the same as R₃ mentioned above.

The production process 2-1 is the method for obtaining the compound shown by formula 2C by reacting the compound shown by formula 2A with the compound shown by formula 2B. The reaction is carried out by stirring at 0° C. to heated reflux temperature, generally for 10 minutes to 24 hours, using an equal amount of the compound shown by formula 2A and the compound shown by formula 2B, or an excessive amount of either one of them. As the reaction solvent, protic polar solvent such as water, ethanol, methanol, propanol is preferably used.

(The Production Process 3-1)

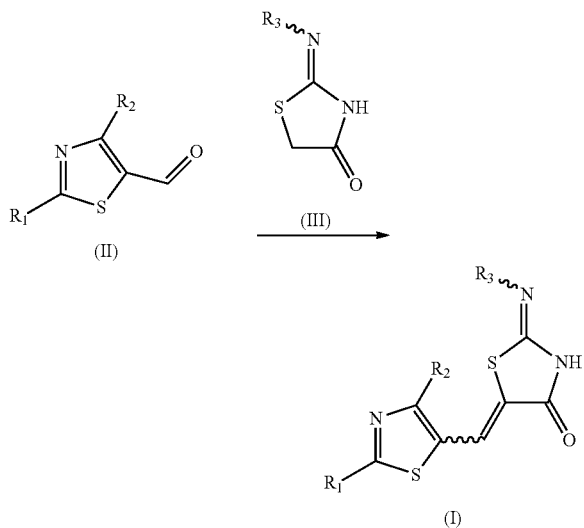

Wherein $R_1$, $R_2$ and $R_3$ are the same as $R_1$, $R_2$ and $R_3$ mentioned above.

The production process 3-1 is the method for obtaining the compound shown by formula (I) by reacting the compound shown by formula (II) with the compound shown by formula (III). The reaction is carried out by stirring at 0° C. to heated reflux temperature, generally for 10 minutes to 24 hours, using an equal amount of the compound shown by formula (II) and the compound shown by formula (III), or an excessive amount of either one of them. As the reaction solvent, protic polar solvent such as water, ethanol, methanol, propanol is preferably used. In the reaction, the base that can be selected from, for example, a pyrimidine, a pyridine, an imidazole, a triethylamine, a diisopropylethylamine, an n-butyllithium is preferably used.

The compounds of the present invention, which can be obtained by the production process mentioned above, can be isolated or purified by employing usual chemical operations such as extraction, concentration, distillation, crystallization, filtration, recrystallization, various chromatographies, and the like.

Furthermore, the present invention provides a pharmaceutical composition including the compound of the present invention, and a pharmaceutically acceptable carrier.

When the compounds or salts, hydrates, or solvates thereof in accordance with the present invention are administered, the administration form is not particularly limited. They may be administered by oral administration or parenteral administration in conventional methods. They can be formulated and administered in dosage forms of, for example, tablets, powder, granules, capsules, syrup, troches, inhalant, suppositories, injection, ointment, eye ointment, eye drop, nasal drop, ear drop, cataplasm, lotion, and the like.

In the preparation, commonly used excipient, binder, lubricant, colorant, flavoring agent, as well as stabilizer, emulsifying agent, absorption promoter, surfactant, pH regulating agents, antiseptics, anti-oxidant, and the like, can be used as necessary, and the preparation is achieved by usual methods while blending components that are generally used as raw materials of pharmaceutical formulation.

For example, in the production of oral formulations, an excipient, and further, as necessary, a binder, a disintegrator, a lubricant, colorant, a flavoring agent, and the like, are added to the compounds or salts, hydrates, or solvates thereof in accordance with the present invention, and the mixture is formed into powder, fine granules, granules, tablets, coating tablets, capsules, and the like, by usual methods.

For example, in the production of liquid agents such as syrup and injection formulations, pH regulating agents, resolvents, tonicity agents, and the like, optionally together with dissolution aids, stabilizers, and the like, are added to the compounds or salts, hydrates, or solvates thereof in accordance with the present invention, and then the mixture is formed into preparations by usual methods.

The dosage amount of the compounds in accordance with the present invention can be appropriately selected depending on the severity of symptom, age, sex, body weight, dosage form, type of the salt, particular type of disease, and the like.

In the case of oral administration, the compounds are administered appropriately to an adult at a dose of about 10 mg to 2000 mg per day, and preferably 50 mg to 1000 mg per day. The compounds are administered once to several times a day.

In the case of intravenous administration, the compounds are administered appropriately to an adult at a dose of about 1 mg to 1000 mg per day, and preferably from 10 mg to 100 mg. The compounds are administered once to several times a day.

EXAMPLES

For example, the compounds of the present invention can be produced by processes described in the following Examples. However, the Examples are just illustrative, and the compounds of the present invention are not limited to the compounds described in the Examples mentioned below.

Compounds 88, 89, 90, 91, 93, 94, 95, 96, 97, 98, 106 and 107 were synthesized by using the materials that have a substituent corresponding to these compounds, according to the following production scheme.

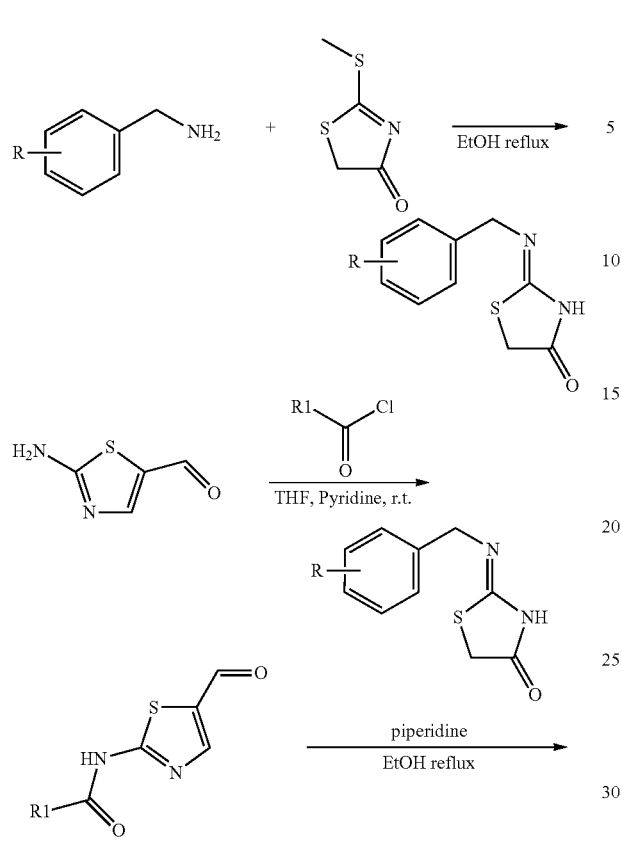
Compounds 104 and 105 were synthesized by using the materials that have a substituent corresponding to these compounds, according to the following production scheme.
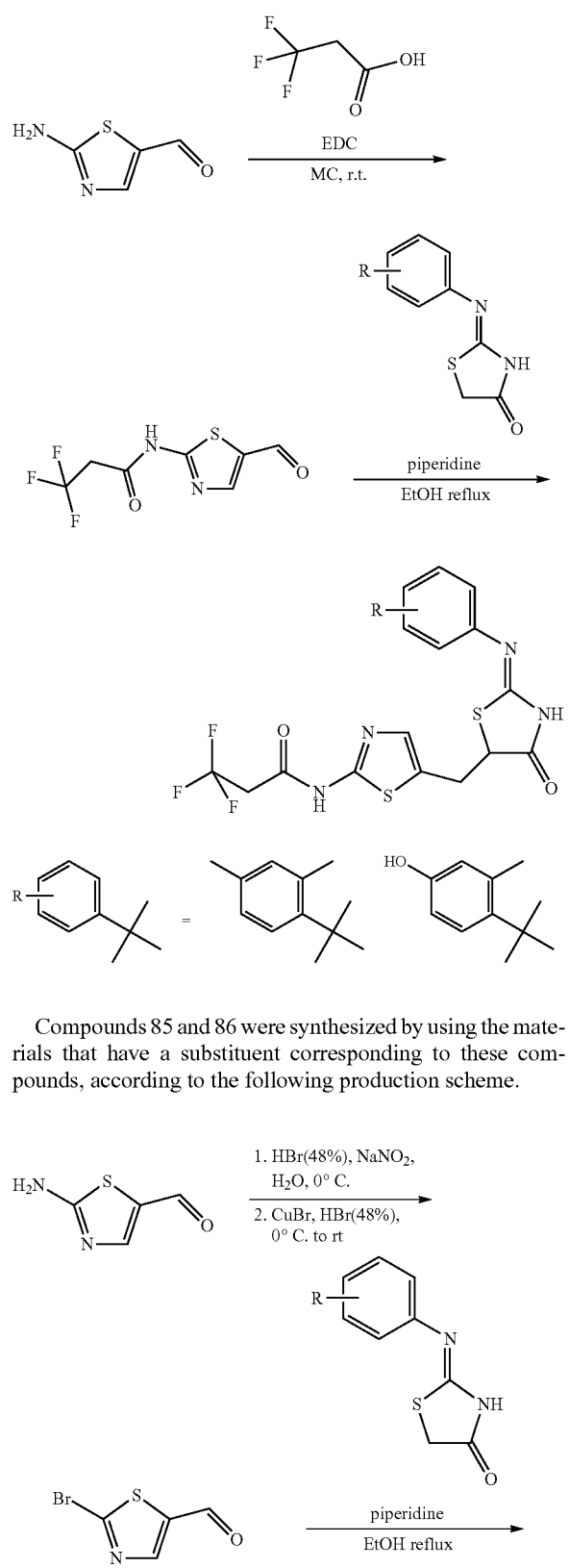
Compounds 85 and 86 were synthesized by using the materials that have a substituent corresponding to these compounds, according to the following production scheme.

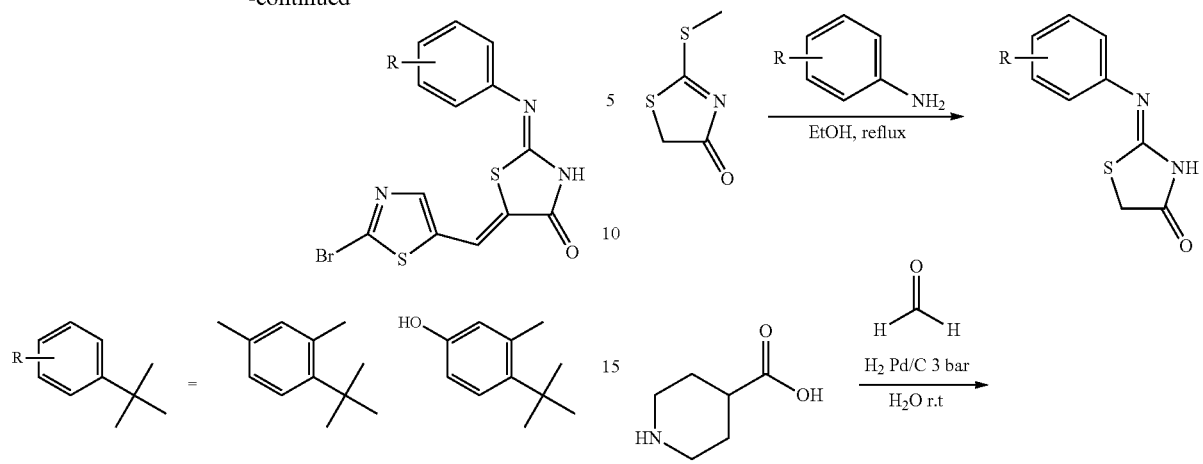

Compounds 102 and 103 were synthesized by using the materials that have a substituent corresponding to these compounds, according to the following production scheme.

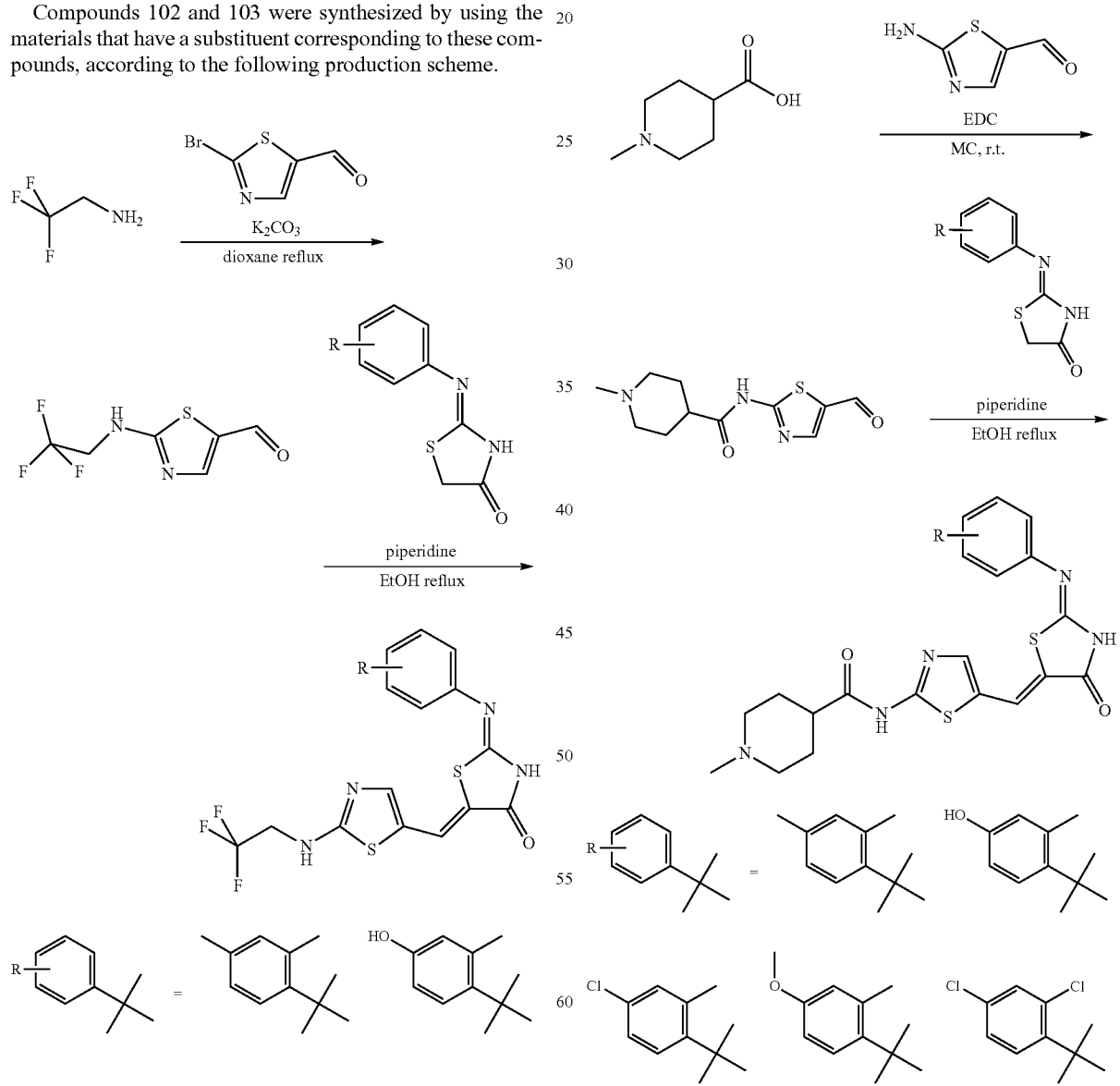

Compounds 108, 109, 143, 144 and 145 were synthesized by using the materials that have a substituent corresponding to these compounds, according to the following production scheme.

Compounds 71 and 72 were synthesized according to the following production scheme.

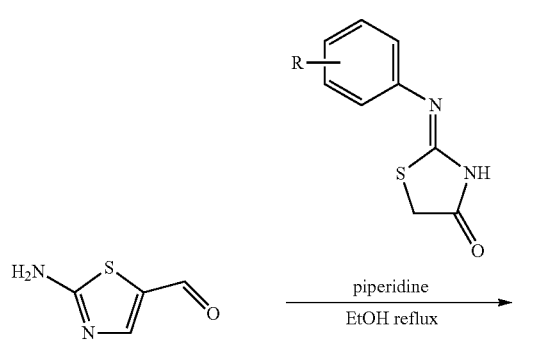

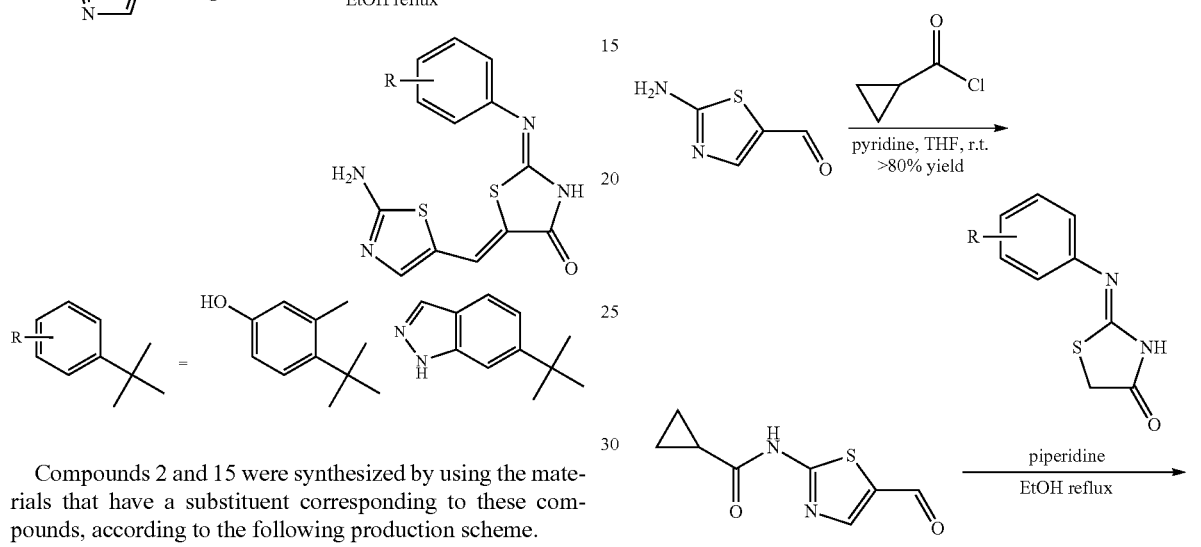

Compounds 2 and 15 were synthesized by using the materials that have a substituent corresponding to these compounds, according to the following production scheme.

Compounds 74 and 81 were synthesized by using the materials that have a substituent corresponding to these compounds, according to the following production scheme.

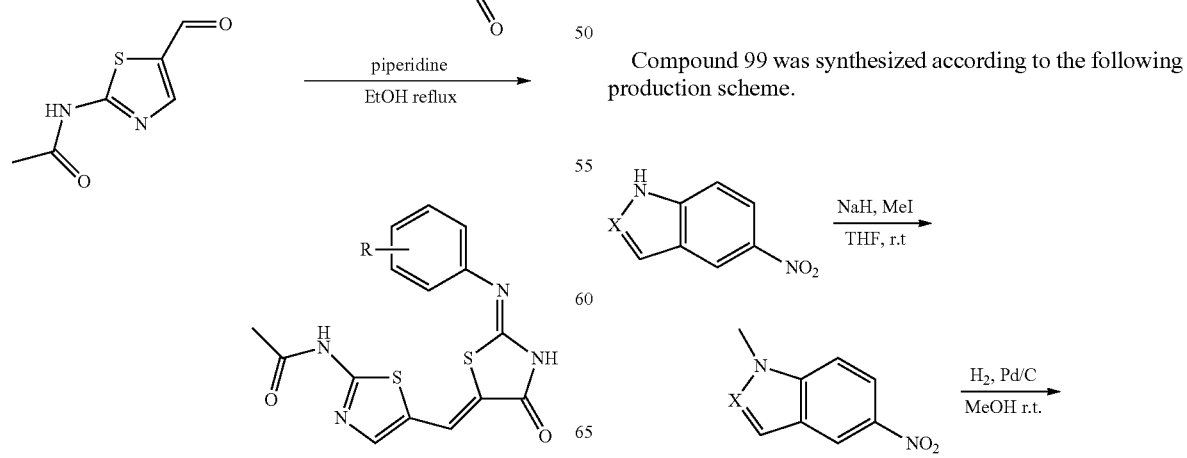

Compound 99 was synthesized according to the following production scheme.

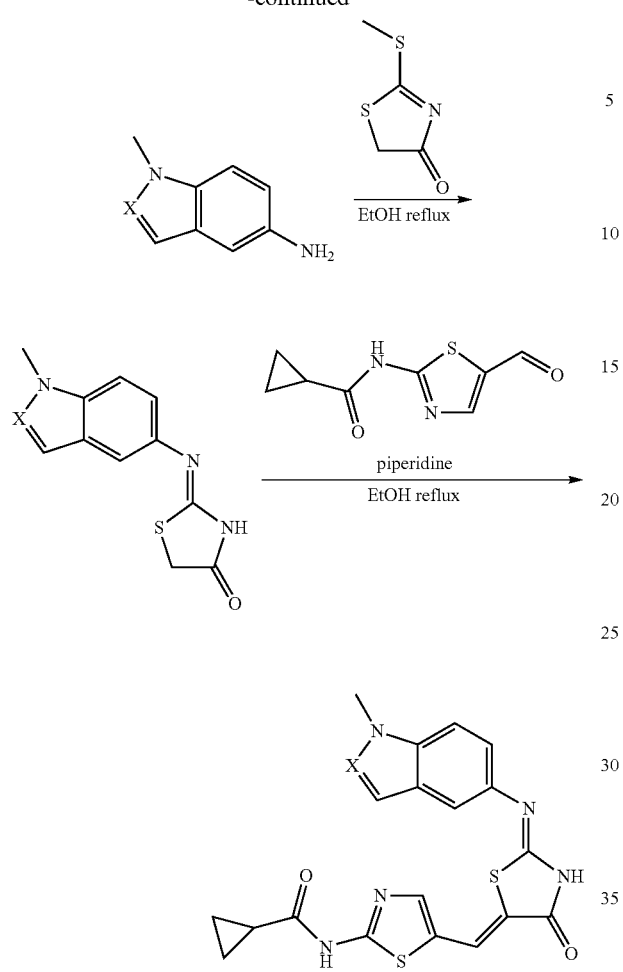
X = N
Compound 129 was synthesized by using the materials that have a substituent corresponding to these compounds, according to the following production scheme.
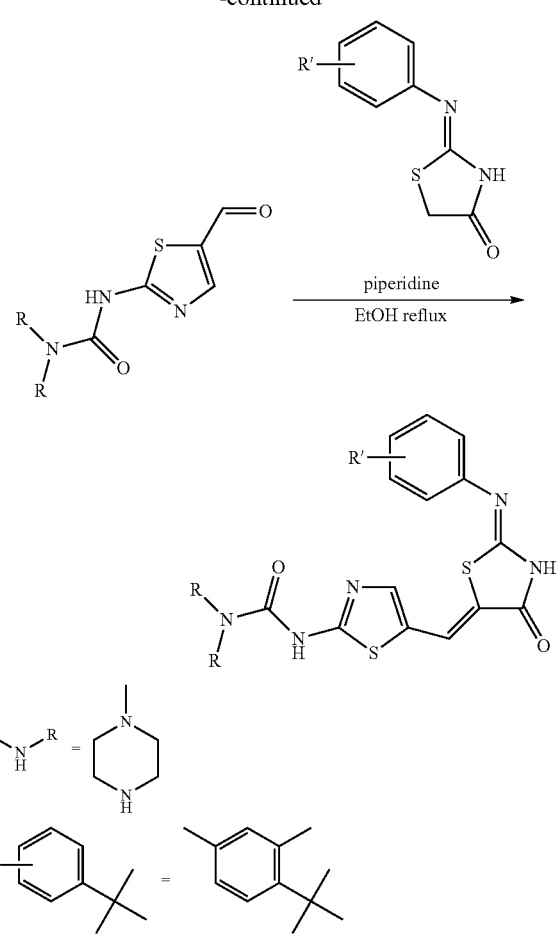
Compounds 127 and 131 were synthesized according to the following production scheme.
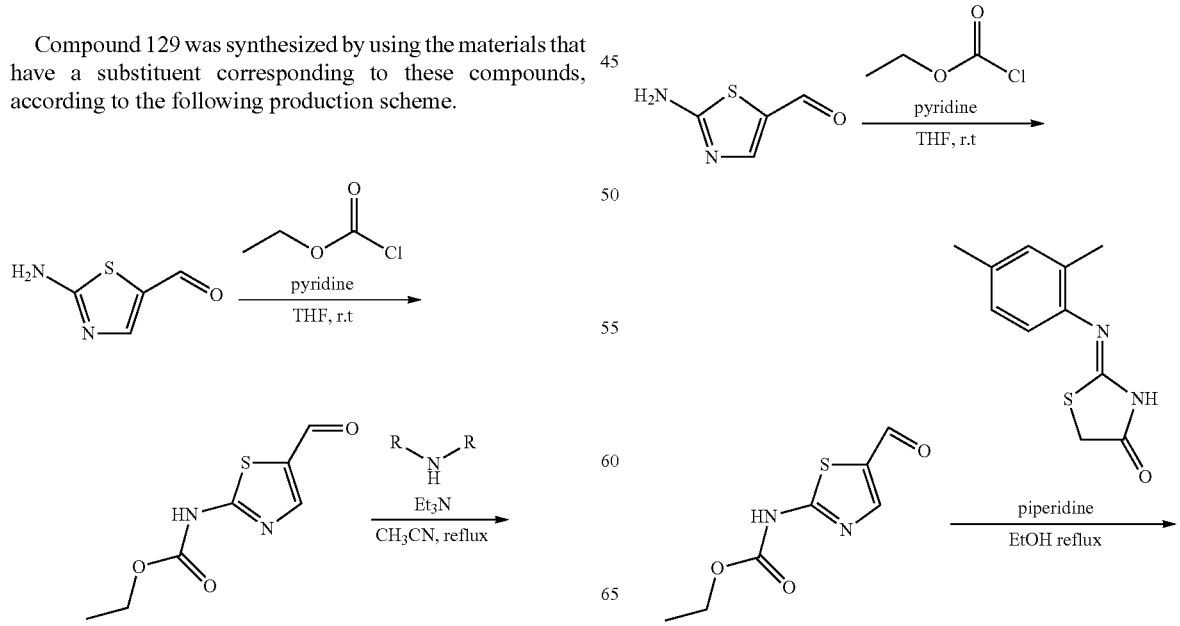

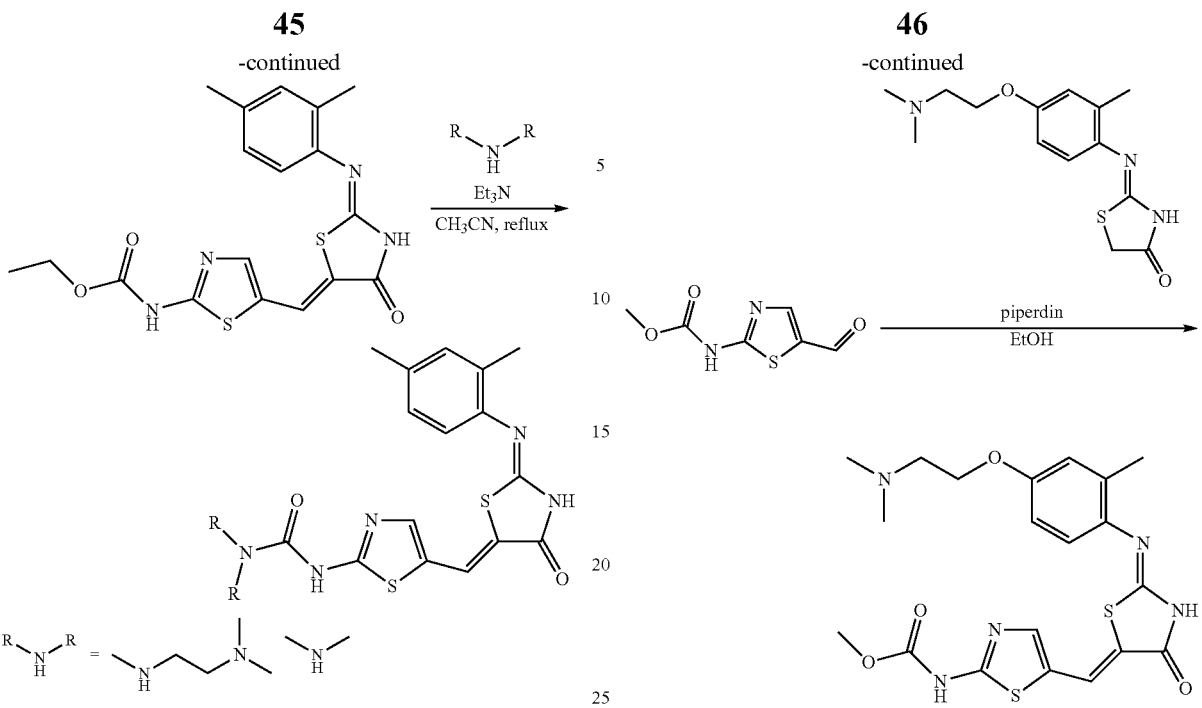
Compound 126 was synthesized according to the following production scheme.
Compound 130 was synthesized according to the following production scheme.
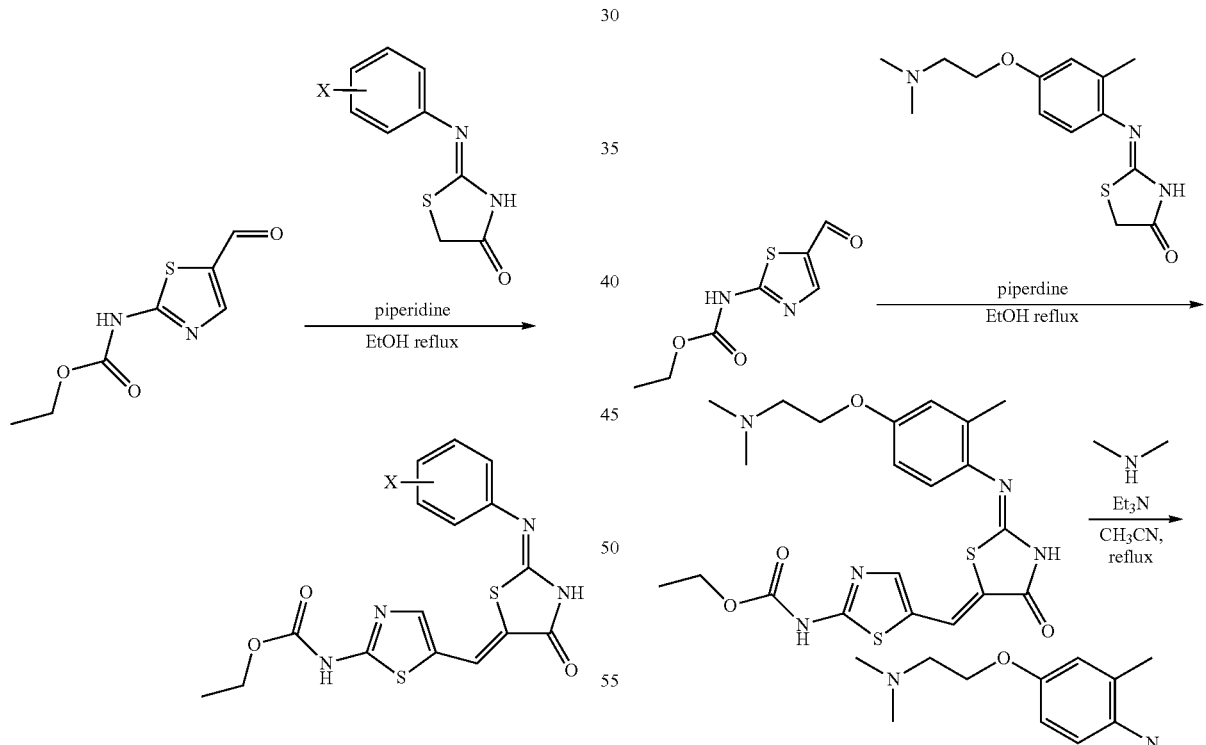
Compound 134 was synthesized according to the following production scheme.
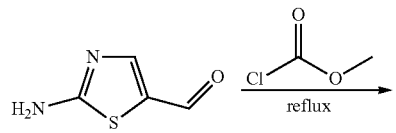
Compounds 110, 111, 112, 113, 114 and 116 were synthesized according to the following production scheme.

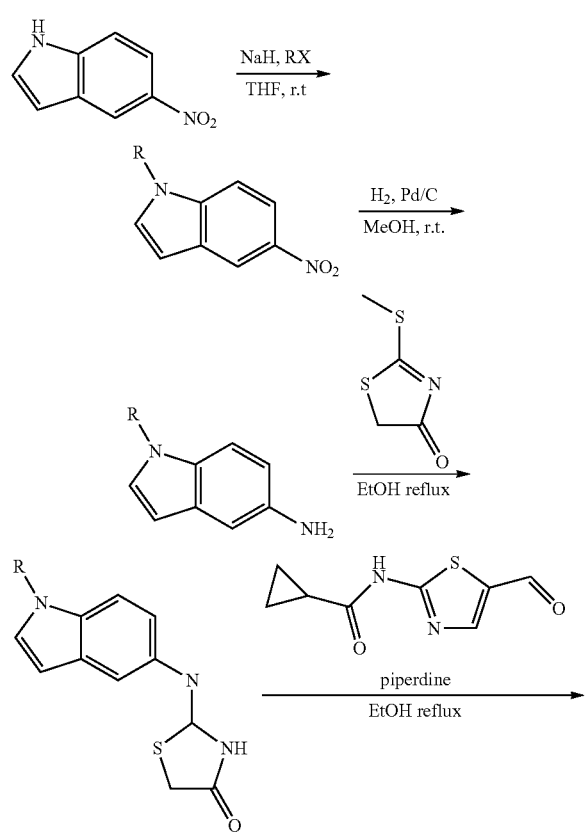
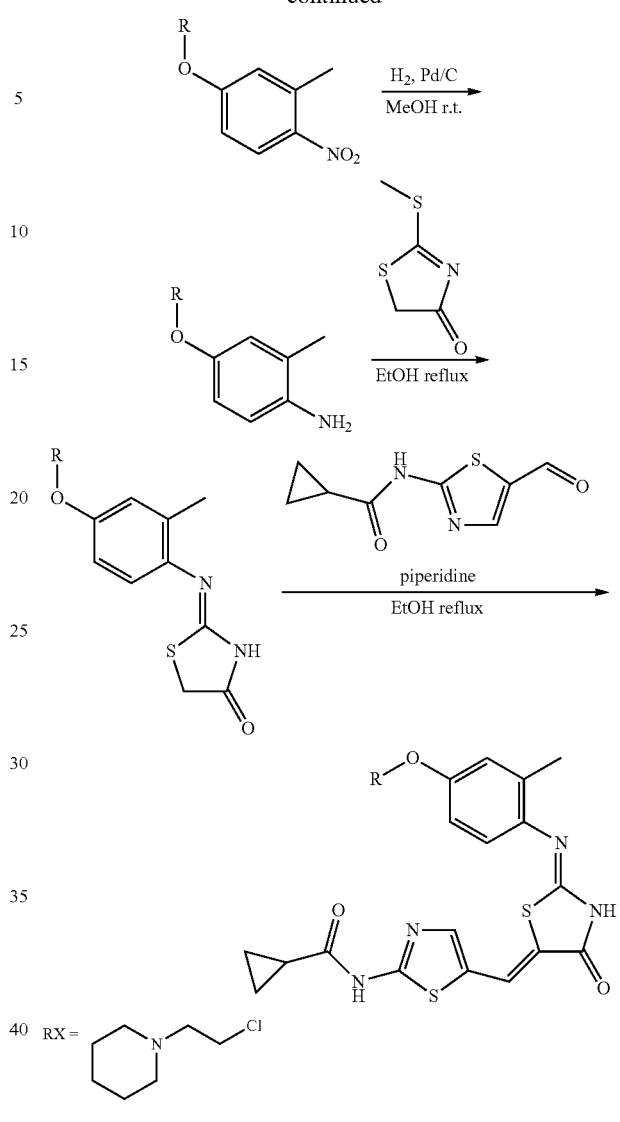
Compound 115 was synthesized by using the materials that have a substituent corresponding to these compounds, according to the following production scheme.
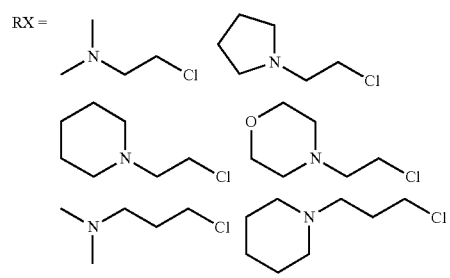
Compounds 135, 136 and 139 were synthesized according to the following production scheme.
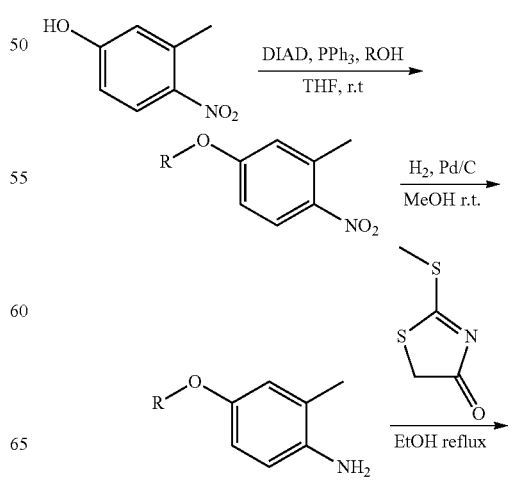

-continued
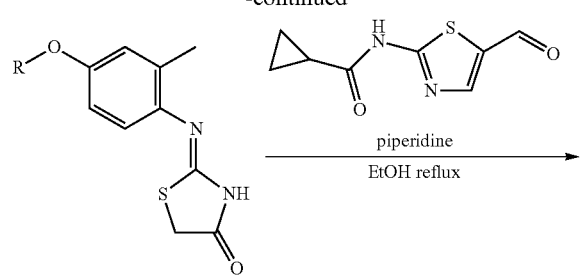
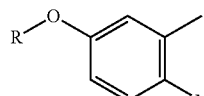
ROH =
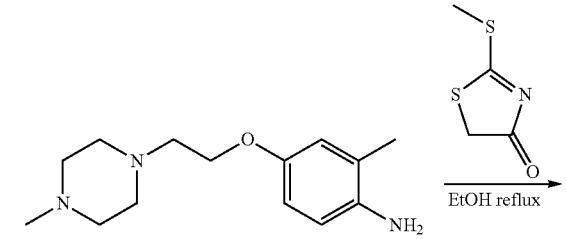
Compound 132 was synthesized according to the following production scheme.
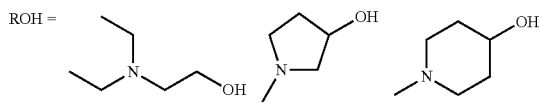
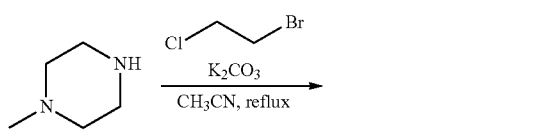
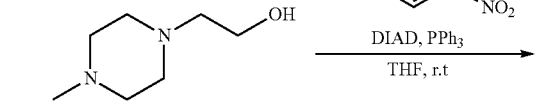
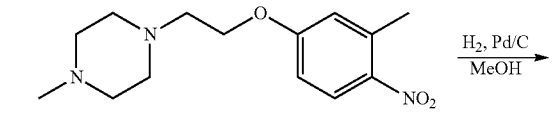
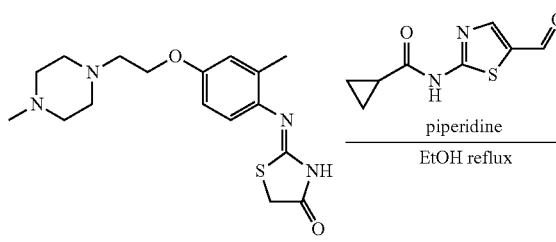
-continued
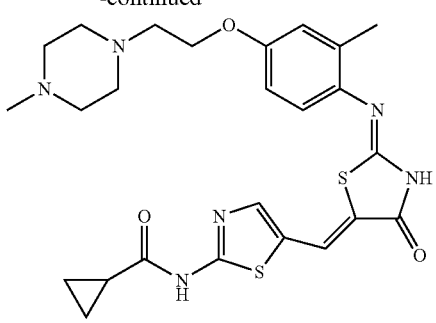
Compound 140 was synthesized according to the following production scheme.
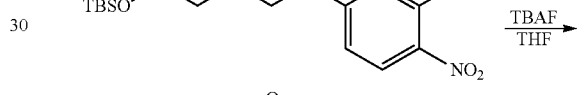
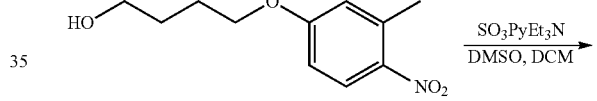
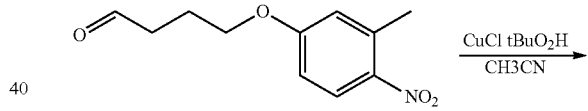
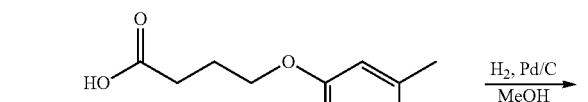
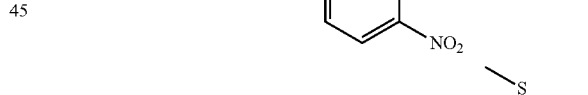
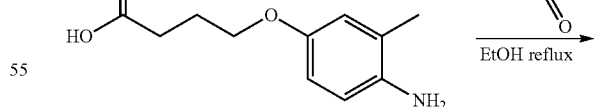
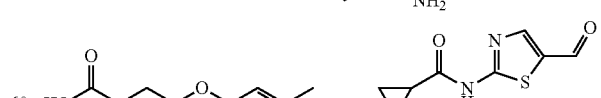

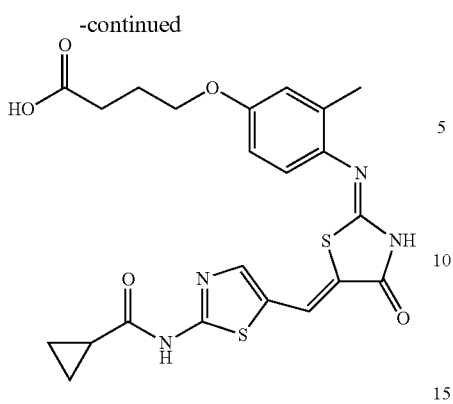
Compounds 146 and 147 were synthesized according to the following production scheme.
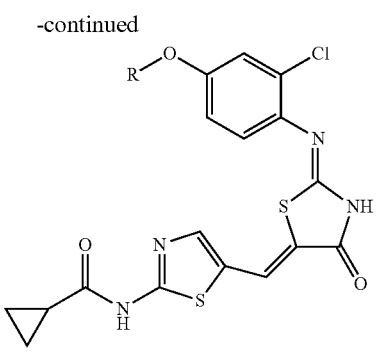
Compounds 141 and 142 were synthesized according to the following production scheme.
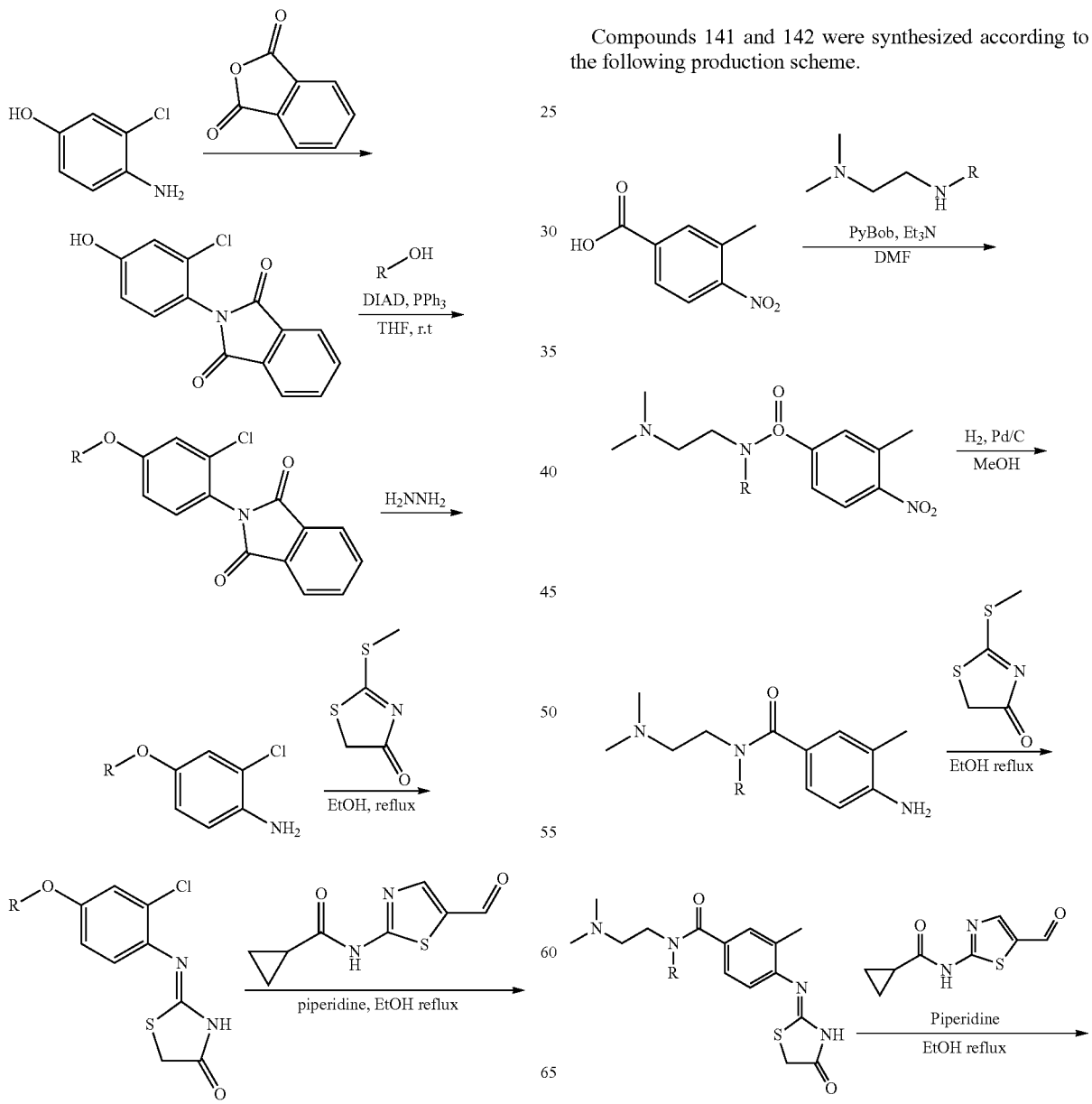

53

-continued

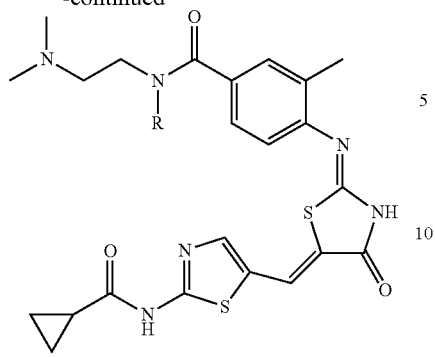

R = H or Me

Compound 133 was synthesized according to the following production scheme.

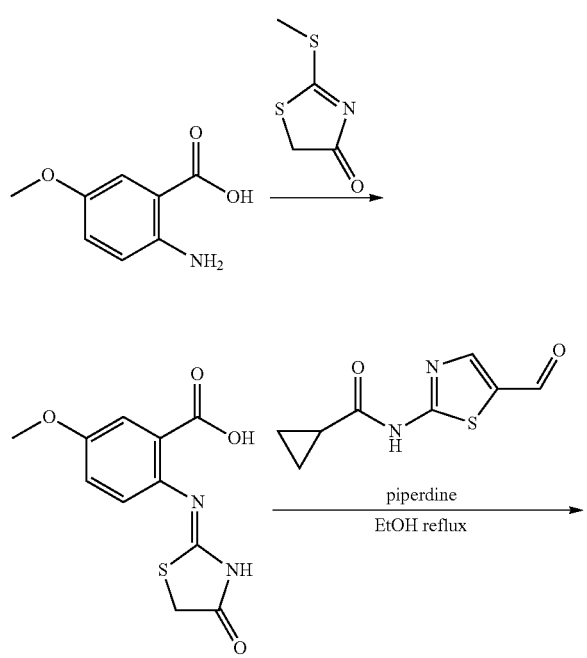

54

-continued

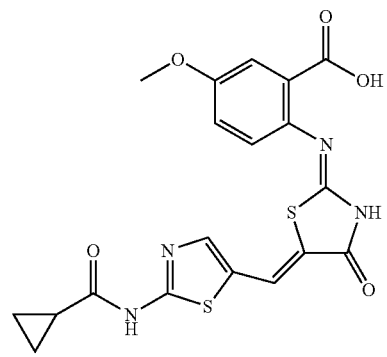

The Example compounds shown in the Tables below were produced by using the corresponding raw materials by the above-mentioned production processes or production processes similar thereto. Table 2 to 24 and 26 to 29 shows the structure, the name, and the physicochemical data of each of the Example compounds.

HPLC of the compounds shown in Tables 2 to 21 below was conducted under the following conditions.

TABLE 1

| | Method A | | | | | Method B | | | |
|---|---|---|---|---|---|---|---|---|---|
| | A: 0.1% Formic acid aqueous solution B: ACN | | | | | A: 0.1% TFA aqueous solution B: ACN | | | |
| Mobile phase | Time (min) | Flow rate (ml/min) | A % | B % | Mobile phase | Time (min) | Flow rate (ml/min) | A % | B % |
| Gradient | 7 | 1 | 100 | 0 | Gradient | 2 | 1 | 95 | 5 |
| | 8.5 | 1 | 100 | 0 | | 13 | 1 | 5 | 95 |
| | 11 | 1 | 5 | 95 | | 18 | 1 | 5 | 95 |
| | 12 | 1 | 5 | 95 | | 19 | 1 | 95 | 5 |
| | | | | | | 20 | 1 | 95 | 5 |
| Wave length | | 254 nm | | | Wave length | | 254 nm | | |

TABLE 2

| Compound No. | Structure | Name | Dtctd Mass |
|---|---|---|---|
| 1 | ![structure] | (2Z,5Z)-5-[(4-methyl(1,3-thiazol-5-yl))methylene]-2-(phenylazamethylene)-1,3-thiazolidin-4-one | 301.9 |

TABLE 2-continued

| | | | |
|---|---|---|---|
| 2 | | (2Z,5Z)-N-(5{[4-oxo-2-(phenylazamethylene)-1,3-thiazolidin-5-ylidene)methyl}-1,3-thiazol-2-yl)acetamide, | 345.0 |
| 3 | | (2Z,5Z)-5-{[2-(ethylamino)(1,3-thiazol-5-yl)]methylene}-2-(phenylazamethylene)-1,3-thiazolidin-4-one | 331.2 |
| 4 | | (2Z,5Z)-5-{[2-(butylamino)(1,3-thiazol-5-yl)]methylene}-2-(phenylazamethylene)-1,3-thiazolidin-4-one, | 358.2 |
| 5 | | (2Z,5Z)-5-{[2-(dimethylamino)(1,3-thiazol-5-yl)]methylene}-2-(phenylazamethylene)-1,3-thiazolidin-4-one, | 331.0 |
| 6 | | (2Z,5Z)-5-{[2-(diethylamino)(1,3-thiazol-5-yl)]methylene}-2-(phenylazamethylene)-1,3-thiazolidin-4-one, | 359.0 |

TABLE 2-continued

| # | Structure | Name | MS |
|---|---|---|---|
| 7 | 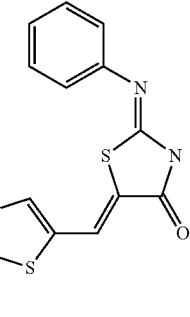 | (2Z,5Z)-5-[(2-{[2-(dimethylamino)ethyl]methylamino}(1,3-thiazol-5-yl))methylene]-2-phenylazamethylene)-1,3-thiazolidin-4-one, | 388.0 |
| 8 | 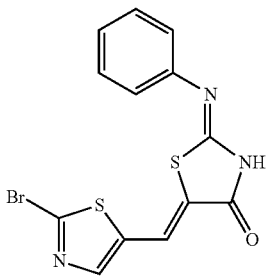 | (2Z,5Z)-5-[(2-bromo(1,3-thiazol-5-yl))methylene]-2-(phenylazamethylene)-1,3-thiazolidin-4-one | 367.0 |

| Compound No. | 1H NMR | HPLC |
|---|---|---|
| 1 | $^1$H NMR (300 MHz, DMSO-d6) δ = 9.18(s, 1H), 7.83-7.76(m, 2H), 7.43(bs, 2H), 7.22(t, J = 7.4 Hz, 1H), 7.07(s, 1H), 2.55(s, 3H) | A Method 8.576 |
| 2 | $^1$H NMR (300 MHz, DMSO-d6) δ = 7.95-7.83(m, 2H), 7.72-7.67(m, 1H), 7.38(t, J = 7.8 Hz, 2H), 7.15(bs, 1H), 7.00(bs, 1H), 2.12(s, 3H) | A Method 8.210 |
| 3 | $^1$H NMR (300 MHz, DMSO-d6) δ = 8.37(bs, 1H), 7.70(bs, 1H), 7.62(bs, 1H), 7.39(t, J = 7.6 Hz, 2H), 7.16(t, J = 7.2 Hz, 1H), 6.98(bs, 1H), 1.89(bs, 2H), 1.12(bs, 3H) | A Method 8.490 |
| 4 | $^1$H NMR (300 MHz, DMSO-d6) δ = 8.35(bs, 1H), 7.69(bs, 1H), 7.61(bs, 1H), 7.39(t, J = 7.5 Hz, 2H), 7.16(t, J = 7.2 Hz, 1H), 7.01(bs, 1H), 3.44(bs, 2H), 1.54-1.50(m, 2H), 1.31(bs, 2H), 0.90-0.85(m, 3H) | A Method 9.296 |
| 5 | $^1$H NMR (300 MHz, DMSO-d6) δ = 7.72(bs, 3H) 7.39(t, J = 7.8 Hz, 2H), 7.16(t, J = 7.8 Hz, 1H), 7.02(bs, 1H), 3.08(bs, 6H) | A Method 8.55 |
| 6 | $^1$H NMR (300 MHz, DMSO-d6) δ = 7.70(bs, 3H), 7.39(t, J = 7.5 Hz, 2H), 7.16(t, J = 6.0 Hz, 1H), 7.01(bs, 1H), 3.47(bs, 4H), 1.14(bs, 6H) | A method 9.24 |
| 7 | $^1$H NMR (300 MHz, DMSO-d6) δ = 7.71(bs, 3H), 7.39(t, J = 7.6 Hz, 2H), 7.16(t, J = 5.5 Hz, 1H), 7.01(bs, 1H), 3.61(bs, 2H), 3.07-3.06(m, 2H), 2.49(bs, 3H), 2.18(bs, 6H) | A Method 6.16 |
| 8 | $^1$H NMR (300 MHz, DMSO-d6) δ = 7.74-7.57(m, 3H), 7.40(t, J = 7.5 Hz, 2H), 7.17(t, J = 7.2 Hz, 1H), 7.01(bs, 1H) | A Method 7.60 |

TABLE 3

| Compound No. | Structure | Name | Dtctd Mass |
|---|---|---|---|
| 9 | 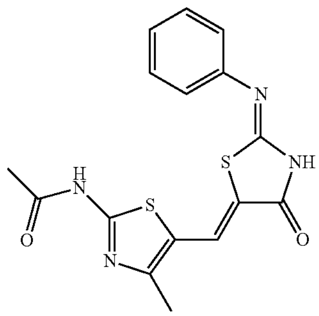 | (2Z,5Z)-N-(4-methyl-5-{[4-oxo-2-(phenylazamethylene)(1,3-thiazolidin-5-ylidene)]methyl}-1,3-thiazol-2-yl)acetamide | 359.1 |
| 10 | 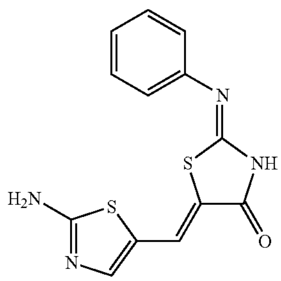 | (2Z,5Z)-5 [(2-amino(1,3-thiazol-5-yl))methylene]-2-(phenylazamethylene)-1,3-thiazolidin-4-one | 303.0 |
| 11 | 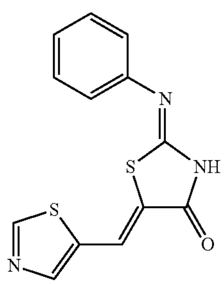 | (2Z,5Z)-2-(phenylazamethylene)-5-(1,3-thiazol-5-ylmethylene)-1,3-thiazolidin-4-one | 287.4 |
| 12 | 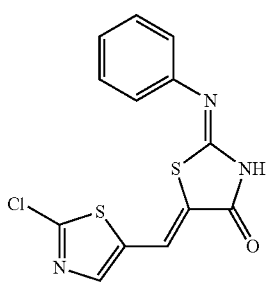 | (2Z,5Z)-5-[(2-chloro(1,3-thiazol-5-yl))methylene]-2-(phenylazamethylene)-1,3-thiazolidin-4-one | 322.8 |
| 13 | 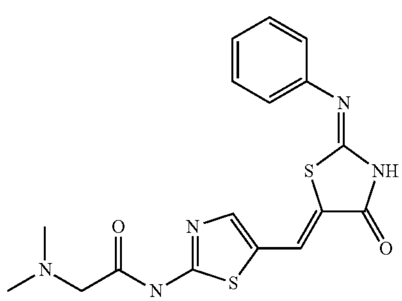 | (2Z,5Z)-2-(dimethylamino)-N-(5-{[4-oxo-2-(phenylazamethylene)(1,3-thiazolidin-5-ylidene)]methyl}-1,3-thiazol-2-yl))acetamide | 387.3 |

TABLE 3-continued

| | | | |
|---|---|---|---|
| 14 | *(structure)* | (2Z,5Z)-5-[(2-hydroxy(1,3-thiazol-5-yl))methylene]-2-[(2-methoxyphenyl)azamethylene]-1,3-thiazolidin-4-one | 334.2 |
| 15 | *(structure)* | (2Z,5Z)-N-[5-({2-[(2-methoxyphenyl)azamethylene]-4-oxo-1,3-thiazolidin-5-ylidene}methyl)-1,3-thiazol-2-yl]acetamide | 375.0 |
| 16 | *(structure)* | (2Z,5Z)-5-[(2-amino(1,3-thiazol-5-yl))methylene]-2-[(2-methoxyphenyl)azamethylene]-1,3-thiazolidin-4-one | 332.0 |

| Compound No. | 1H NMR | HPLC |
|---|---|---|
| 9 | $^1$H NMR (300 MHz, DMSO-d6) δ = 7.76-7.66(m, 2H), 7.41(t, J = 7.5 Hz, 2H), 7.18(t, J = 7.2 Hz, 1H), 7.03(bs, 1H), 2.42(d, J = 8.4 Hz, 3H), 2.42(s, 3H) | A Method 7.24 |
| 10 | $^1$H NMR (300 MHz, DMSO-d6) δ = 7.73(bs, 2H), 7.63(bs, 1H), 7.50(bs, 1H), 7.13(bs, 1H), 7.06(bs, 1H), 6.92(s, 2H), 3.73(s, 3H) | A Method 7.11 |
| 11 | $^1$H NMR (300 MHz, DMSO-d6) δ = 9.25(bs, 1H), 8.35(bs, 1H), 7.97(bs, 1H), 7.74(bs, 1H), 7.40(t, J = 7.5 Hz, 2H), 7.21(t, J = 7.3 Hz, 1H), 7.05(d, J = 7.2 Hz, 1H) | A Method 8.26 |
| 12 | $^1$H NMR (300 MHz, DMSO-d6) δ = 9.56(s, 1H), 8.39(s, 1H), 7.75(bs, 1H), 7.41(m, 2H), 7.20(t, J = 7.3 Hz, 1H), 7.05(d, J = 7.2 Hz, 1H) | B Method 13.85 |
| 13 | $^1$H NMR (300 MHz, DMSO-d6) δ = 7.98-7.68(m, 4H), 7.40(t, J = 7.5 Hz, 2H), 7.18(bs, 1H), 7.04(bs, 1H), 2.55-2.54(m, 2H), 2.26(bs, 6H) | A Method 5.624 |
| 14 | $^1$H NMR (300 MHz, DMSO-d6) δ = 11.96(bs, 1H), 7.58(bs, 2H), 7.18(bs, 1H), 7.09(bs, 1H), 6.95(s, 2H), 3.74(s, 3H) | A Method 6.90 |
| 15 | $^1$H NMR (300 MHz, DMSO-d6) δ = 7.89(s, 1H), 7.76(s, 1H), 7.16(bs, 1H) 7.08(bs, 1H) 6.94(s 2H), 3.73(s, 3H), 2.11(s, 3H) | A Method 7.763 |
| 16 | $^1$H NMR (300 MHz, DMSO-d6) δ = 7.73(s, 3H), 7.63(bs, 1H), 7.50(bs, 1H), 7.13(bs, 1H), 7.06(bs, 1H), 6.92(s, 2H), 3.73(s, 3H) | A Method 7.242 |

TABLE 4

| Compound No. | Structure | Name | Dtctd Mass |
|---|---|---|---|
| 17 | 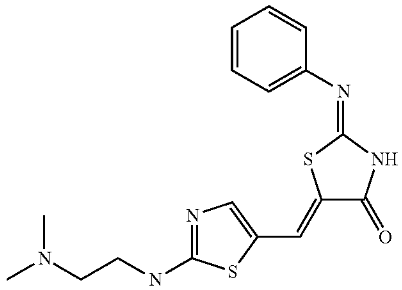 | (2Z,5Z)-5-[(2-{[2-(dimethylamino)ethyl]amino}(1,3-thiazol-5-yl)methylene]-2-(phenylazamethylene)-1,3-thiazolidin-4-one | 373.2 |
| 18 | 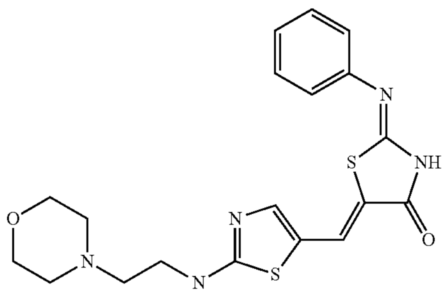 | (2Z,5Z)-5-{[2-[(2-morpholinoethyl)amino](1,3-thiazol-5-yl)]methylene}-2-(phenylazamethylene)-1,3-thiazolidin-4-one | 417.1 |
| 19 | 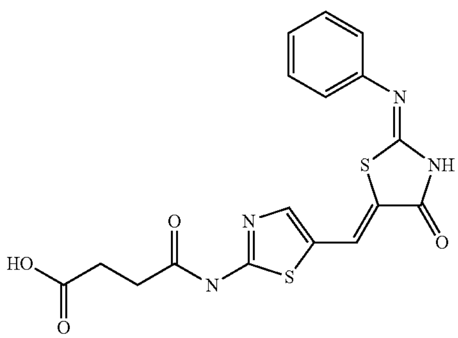 | (2Z,5Z)-3-[N-(5-{[4-oxo-2-(phenylazamethylene)-1,3-thiazolidin-5-ylidene]methyl}-1,3-thiazol-2-yl)carbamoyl]propionic acid | 403.0 |
| 20 | 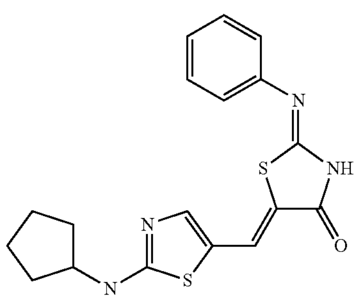 | (2Z,5Z)-5-{[2-(cyclopentylamino)(1,3-thiazol-5-yl)methylene]-2-(phenylazamethylene)-1,3-thiazolidin-4-one | 370.4 |
| 21 | 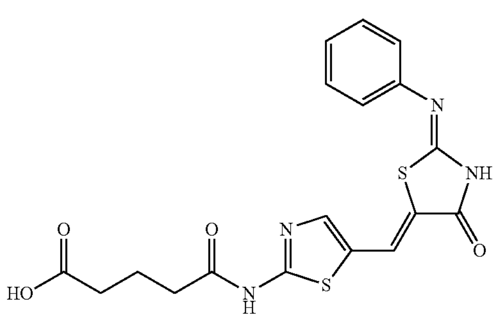 | (2Z,5Z)-4-[N-(5-{[4-oxo-2-(phenylazamethylene)-1,3-thiazolidin-5-ylidene]methyl}-1,3-thiazol-2-yl)carbamoyl]butyric acid | 416.7 |

TABLE 4-continued

| | | | |
|---|---|---|---|
| 22 | | (2Z,5Z)-5-{[2-(cyclohexylamino)(1,3-thiazol-5-yl)methylene]-2-(phenylazamethylene)-1,3-thiazolidin-4-one | 384.3 |
| 23 | | (2Z,5Z)-5-[(2-{[4-(dimethylamino)butyl]amino}(1,3-thiazol-5-yl))methylene]-2-(phenylazamethylene)-1,3-thiazolidin-4-one | 401.3 |
| 24 | | (2Z,5Z)-5-[(2-{[3-(dimethylamino)propyl]amino}(1,3-thiazol-5-yl))methylene]-2-(phenylazamethylene)-1,3-thiazolidin-4-one | 387.4 |

| Compound No. | 1H NMR | HPLC |
|---|---|---|
| 17 | $^1$H NMR (300 MHz, CD$_3$OD) δ = 7.68(bs, 2H), 7.48(bs, 1H), 7.39(t, J = 7.5 Hz, 2H), 7.19(bs, 1H), 7.08(bs, 1H), 3.72(bs, 2H), 3.24-3.22(m, 2H) 2.79(s, 6H) | A Method 6.48 |
| 18 | $^1$H NMR (300 MHz, CD$_3$OD) δ = 7.74(s, 1H), 7.38-7.18(m, 6H), 3.94(bm, 2H), 3.59-3.31(m, 4H), 2.56(bs, 2H), 2.40(m, 4H) | A Method 6.65 |
| 19 | $^1$H NMR (300 MHz, DMSO-d6 + TFA) δ = 7.98(s, 1H), 7.90(s, 1H), 7.74(bs, 1H), 7.41(t, J = 7.5 Hz, 2H), 7.20(t, J = 6.3 Hz, 1H), 7.08(d, J = 7.5 Hz, 1H), 2.65(m, 2H), 3.45(m, 2H) | B Method 10.33 |
| 20 | $^1$H NMR (300 MHz, DMSO-d6) δ = 8.39(bs, 1H), 7.70-7.62(m, 3H), 7.39(t, J = 7.8 Hz, 2H), 7.16(t, J = 7.2 Hz, 1H), 7.01(bs, 1H), 3.97(bs, 1H), 1.89(bs, 2H), 1.52(bs, 6H) | A Method 9.380 |
| 21 | $^1$H NMR (300 MHz, DMSO-d6 + TFA) δ = 7.94(s, 1H), 7.84(s, 1H), 7.72(bs, 1H), 7.41(t, J = 7.4 Hz, 2H), 7.20(t, J = 6.3 Hz, 1H), 7.08(d, J = 7.5 Hz, 1H), 2.24(m, 4H), 1.79(m, 2H) | A Method 7.58 |
| 22 | $^1$H NMR (300 MHz, DMSO-d6) δ = 8.29(bs, 1H), 7.72-7.59(m, 3H), 7.38(t, J = 7.5 Hz, 2H), 7.16(t, J = 7.2 Hz, 1H), 7.00(bs, 2H), 3.52(bs, 1H), 1.89(bs, 2H), 1.67(bs, 2H), 1.25(bs, 6H) | A Method 9.747 |
| 23 | $^1$H NMR (300 MHz, CD$_3$OD) δ = 8.41(s, 1H), 7.65(bs, 2H), 7.47(bs, 1H) 7.39(t, J = 6.9 Hz, 2H), 7.20(bs, 1H), 7.06(bs, 1H), 3.36(bs, 2H), 3.12(bs, 2H), 2.85(s, 6H), 2.63(bs, 2H), 1.72(bs, 2H) | B Method 7.346 |
| 24 | $^1$H NMR (300 MHz, CD$_3$OD) δ = 8.42(s, 1H), 7.68(bs, 2H), 7.43(bs, 1H), 7.39(t, J = 7.8 Hz, 2H), 7.20(bs, 1H), 7.06(bs, 1H), 3.45(bs, 2H), 3.13(bs, 2H), 2.85(s, 6H), 2.01(bs, 2H) | B Method 7.179 |

TABLE 5

| Compound No. | Structure | Name | Dtctd Mass |
| --- | --- | --- | --- |
| 25 | 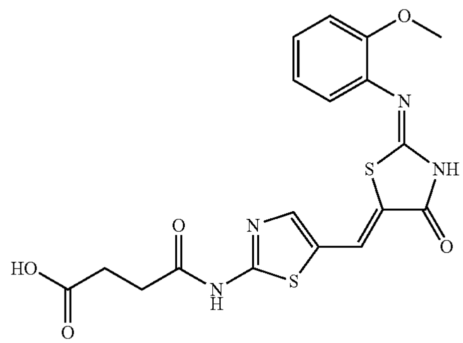 | (2Z,5Z)-5-{N-[5-({2-[(2-methoxyphenyl)azamethylene]-4-oxo-1,3-thiazolidin-5-ylidene}methyl)-1,3-thiazol-2-yl]carbamoyl}propionic acid | 444.8 |
| 26 | 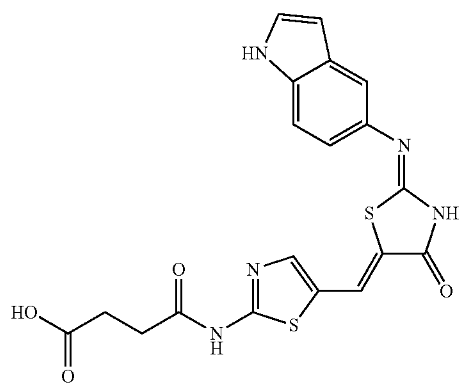 | (5Z)-3-[N-(5-{[2-(indol-5-ylazamethylene)-4-oxo-1,3-thiazolidin-5-ylidene]methyl}-1,3-thiazol-2-yl)carbamoyl]propionic acid | 441.0 |
| 27 | 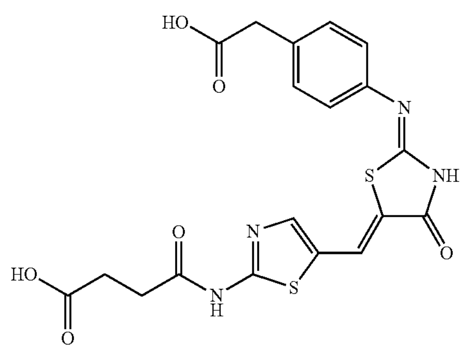 | (2Z,5Z)-3-(N-{5-[(2-{[4-(carboxymethyl)phenyl]azamethylene}-4-oxo-1,3-thiazolidin-5-ylidene)methyl]-1,3-thiazol-2-yl}carbamoyl)propionic acid | 460.8 |
| 28 | 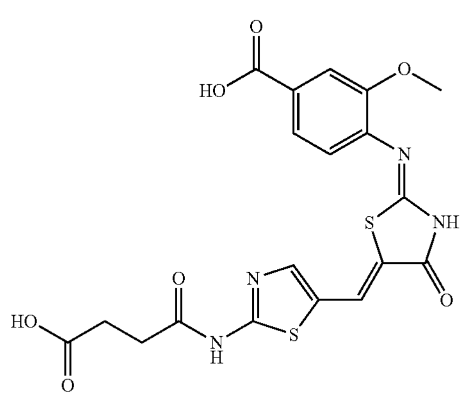 | (2Z,5Z)-4-[(5-{[2-(3-carboxypropanoylamino)(1,3-thiazol-5-yl)]methylene}-4-oxo(1,3-thiazolidin-2-ylidene))azamethyl]-3-methoxybenzoic acid | 476.7 |

TABLE 5-continued

| 29 | 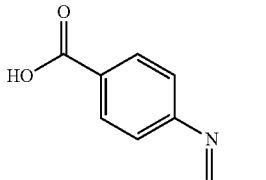 | (2Z,5Z)-4-[(5-{[2-(3-carboxypropanoylamino)(1,3-thiazol-5-yl)]methylene}-4-oxo(1,3-thiazolidin-2-ylidene))azamethyl]benzoic acid | 444.5 |
| 30 | 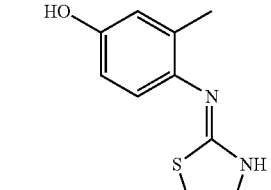 | (2Z,5Z)-5-{N-[5-({2-[(4-hydroxy-2-methylphenyl)azamethylene]-4-oxo-1,3-thiazolidin-5-ylidene}methyl)-1,3-thiazol-2-yl]carbamoyl}propionic acid | 434.4 |
| 31 | 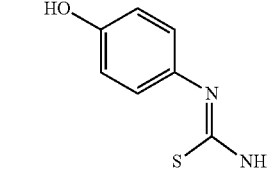 | (2Z,5Z)-3-{N-[5-({2-[(4-hydroxyphenyl)azamethylene]-4-oxo-1,3-thiazolidin-5-ylidene}methyl)-1,3-thiazol-2-yl]carbamoyl}propionic acid | 416.6 |
| 32 | 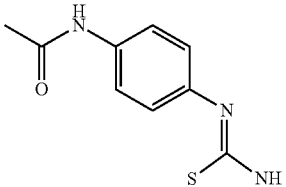 | (2Z,5Z)-3-(N-{5-[(2-{[4-(acetylamino)phenyl]azamethylene}-4-oxo-1,3-thiazolidin-5-ylidene)methyl]-1,3-thiazol-2-yl}carbamoyl)propionic acid | 457.5 |

| Compound No. | 1H NMR | HPLC |
|---|---|---|
| 25 | $^1$H NMR (300 MHz, DMSO-d6) δ = 7.90(s, 1H), 7.76(s, 1H), 7.16(bs, 1H), 7.08(bs, 1H), 6.94(s, 2H), 2.68(m, 2H), 2.56(m, 2H) | A Method 6.85 |
| 26 | $^1$H NMR (300 MHz, DMSO-d6) δ = 12.50(s, 1H), 11.18(s, 1H), 7.97-7.81(m, 2H), 7.44-7.36(m, 3H), 6.90(bs, 1H), 6.46(bs, 1H), 2.71-2.66(m, 2H), 2.62-2.55(m, 2H) | B Method 9.621 |

TABLE 5-continued

| | | | |
|---|---|---|---|
| | 27 | $^1$H NMR (300 MHz, DMSO-d6) δ = 7.82(bs, 1H), 7.72(bs, 1H), 7.57(bs, 1H), 7.26(t, J = 7.5 Hz, 2H), 6.91(bs, 1H), 3.57-3.45(m, 2H), 2.71-2.59(m, 2H), 2.54-2.53(m, 2H) | B Method 9.608 |
| | 28 | No data | B Method 9.600 |
| | 29 | $^1$H NMR (300 MHz, DMSO-d6 + TFA) δ = 7.96-7.90(m, 5H), 7.11(bs, 1H), 2.72-2.48(m, 4H) | B Method 9.610 |
| | 30 | $^1$H NMR (300 MHz, DMSO-d6 + TFA) δ = 7.78(s, 1H), 7.67(s, 1H), 7.52(s, 1H), 6.90-6.58(m, 2H), 2.73-2.48(m, 4H), 2.27(s, 3H) | A Method 6.91 |
| | 31 | $^1$H NMR (300 MHz, DMSO-d6 + TFA) δ = 7.94(d, J = 6.3 Hz, 1H), 7.84(d, J = 9.9 Hz, 1H), 7.52(d, J = 8.7 Hz, 1H), 6.93(d, J = 8.4 Hz, 1H), 6.79(t, J = 8.7 Hz, 2H), 2.67(m, 2H), 2.54(m, 2H) | A Method 6.93 |
| | 32 | $^1$H NMR (300 MHz, DMSO-d6 + TFA) δ = 9.96(s, 1H), 7.86-7.55(m, 4H), 7.02(bs, 1H), 6.93(d, J = 8.4 Hz, 1H), 2.70-2.59(m, 2H), 2.58-2.49(m, 2H), 2.02(s, 3H) | A Method 6.90 |

TABLE 6

| Compound No. | Structure | Name | Dtctd Mass |
|---|---|---|---|
| 33 | 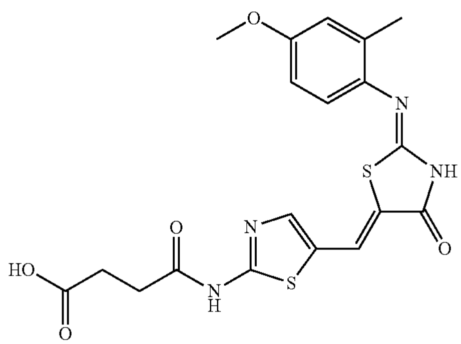 | (2Z,5Z)-3-{N-[5-({2-[(4-methoxy-2-methylphenyl)azamethylene]-4-oxo-1,3-thiazolidin-5-ylidene}methyl)-1,3-thiazol-2-yl]carbamoyl}propionic acid | 446.4 |
| 34 | 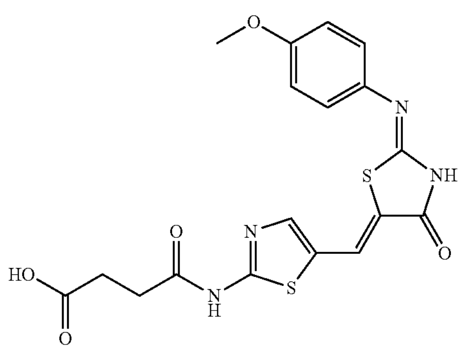 | (2Z,5Z)-3-{N-[5-({2-[(4-methoxyphenyl)azamethylene]-4-oxo-1,3-thiazolidin-5-ylidene}methyl)-1,3-thiazol-2-yl]carbamoyl}propionic acid | 432.5 |
| 35 | 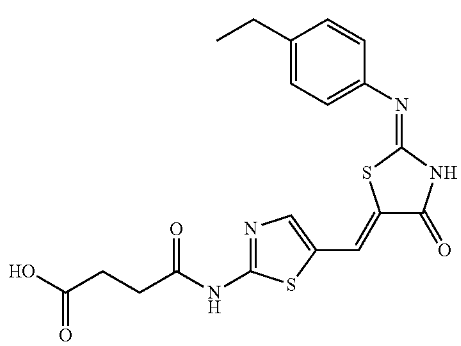 | (2Z,5Z)-3-{N-[5-({2-[(4-ethylphenyl)azamethylene]-4-oxo-1,3-thiazolidin-5-ylidene}methyl)-1,3-thiazol-2-yl]carbamoyl}propionic acid | 430.6 |

| | | | |
|---|---|---|---|
| 36 | 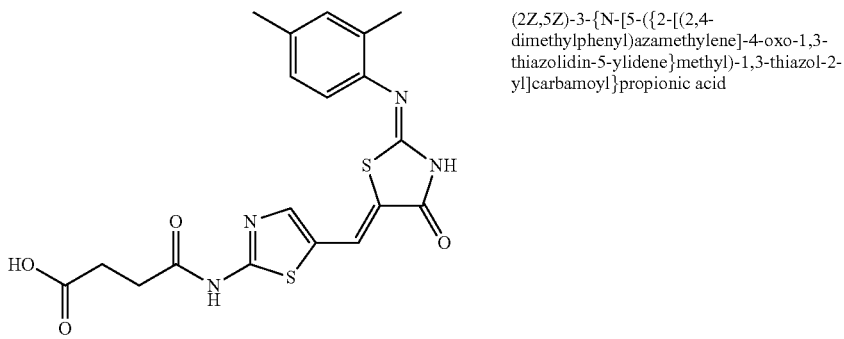 | (2Z,5Z)-3-{N-[5-({2-[(2,4-dimethylphenyl)azamethylene]-4-oxo-1,3-thiazolidin-5-ylidene}methyl)-1,3-thiazol-2-yl]carbamoyl}propionic acid | 430.5 |
| 37 | 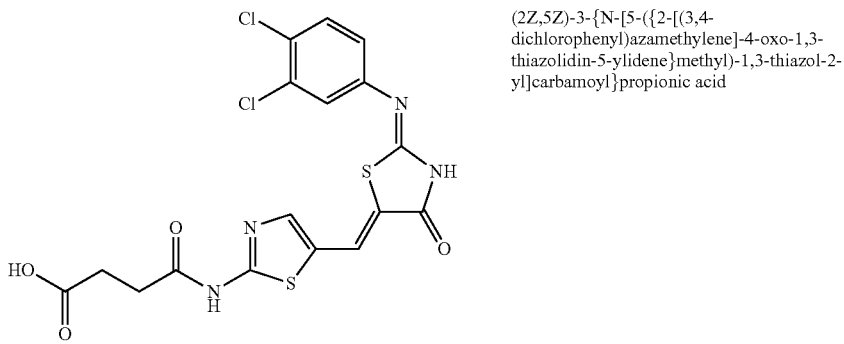 | (2Z,5Z)-3-{N-[5-({2-[(3,4-dichlorophenyl)azamethylene]-4-oxo-1,3-thiazolidin-5-ylidene}methyl)-1,3-thiazol-2-yl]carbamoyl}propionic acid | 469.1 |
| 38 | 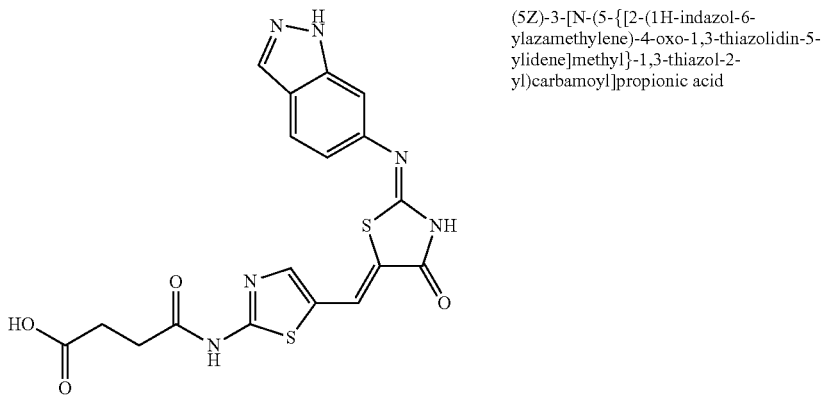 | (5Z)-3-[N-(5-{[2-(1H-indazol-6-ylazamethylene)-4-oxo-1,3-thiazolidin-5-ylidene]methyl}-1,3-thiazol-2-yl)carbamoyl]propionic acid | 442.4 |
| 39 | 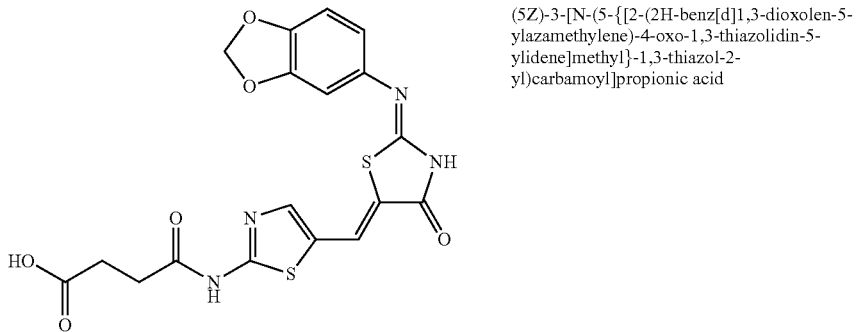 | (5Z)-3-[N-(5-{[2-(2H-benz[d]1,3-dioxolen-5-ylazamethylene)-4-oxo-1,3-thiazolidin-5-ylidene]methyl}-1,3-thiazol-2-yl)carbamoyl]propionic acid | 446.5 |

TABLE 6-continued

| 40 | [structure] | (5Z)-3-[N-(5-{[2-(1H-indazol-5-ylazamethylene)-4-oxo-1,3-thiazolidin-5-ylidene]methyl}-1,3-thiazol-2-yl)carbamoyl]propionic acid | 441.1 |

| Compound No. | 1H NMR | HPLC |
| --- | --- | --- |
| 33 | ¹H NMR (300 MHz, DMSO-d6) δ = 7.95(s, 1H), 7.83(s, 1H), 6.95-6.77(m, 3H), 3.76(s, 3H), 2.72-2.60(m, 2H), 2.57-2.52(m, 2H), 2.12(s, 3H) | B Method 10.794 |
| 34 | ¹H NMR (300 MHz, DMSO-d6) δ = 7.96(d, J = 6.0 Hz, 1H), 7.85(d, J = 9.0 Hz, 1H), 7.63(d, J = 3.6 Hz, 1H), 7.00(bs, 3H), 3.77(s, 3H), 2.72-2.60(m, 2H), 2.57-2.52(m, 2H) | B Method 10.734 |
| 35 | ¹H NMR (300 MHz, DMSO-d6) δ = 7.96(s, 1H), 7.85(s, 1H), 7.64(d, J = 8.1 Hz, 1H), 7.25(bs, 2H), 6.99(d, J = 7.8 Hz, 1H), 2.70-2.49(m, 6H), 1.23-1.14(m, 3H) | B Method 12.186 |
| 36 | ¹H NMR (300 MHz, DMSO-d6) δ = 7.93(bs, 1H), 7.83(s, 1H), 7.09(s, 1H), 7.04(t, J = 8.1 Hz, 1H), 6.83(t, J = 7.2 Hz, 1H), 2.67-2.62(m, 2H), 2.55-2.51(m, 2H), 2.28(s, 3H), 2.09(s, 3H) | B Method 11.566 |
| 37 | ¹H NMR (300 MHz, DMSO-d6 + TFA) δ = 7.98(s, 1H), 7.88(s, 1H), 7.64(d, J = 8.4 Hz, 1H), 7.29(s, 1H) 7.04(d, J = 8.4 Hz, 1H), 2.67(bm, 2H), 2.55(bm, 2H), | B Method 10.00 |
| 38 | ¹H NMR (300 MHz, DMSO-d6) δ = 13.01(bs, 1H), 12.59(bs, 2H), 7.96(s, 1H), 7.93(s, 1H), 7.87(s, 1H), 7.20(d, J = 7.8 Hz, 1H), 7.14(s, 1H), 6.81(d, J = 8.4 Hz, 1H), 2.71-2.62(m, 2H), 2.60-2.55(m, 1H) | B Method 9.705 |
| 39 | ¹H NMR (300 MHz, DMSO-d6) δ = 7.93(s, 1H), 7.79(s, 1H), 6.93(d, J = 8.1 Hz, 1H), 6.64(s, 1H), 6.47(d, J = 7.5 Hz, 1H), 6.06(s, 2H), 2.68-2.65(m, 2H), 2.55-2.52(m, 2H) | B Method 10.687 |
| 40 | ¹H NMR (300 MHz, DMSO-d6 + TFA) δ = 7.80(m, 2H), 7.54-7.26(m, 3H), 6.93(d, J = 8.1 Hz, 1H), 6.53(bm, 1H), 6.44(bs, 1H), 2.68-2.64(m, 2H), 2.52-2.46(m, 2H) | A Method 6.49 |

TABLE 7

| Compound No. | Structure | Name | Dtctd Mass |
| --- | --- | --- | --- |
| 41 | [structure] | (5Z)-3-[N-(5-{[2-(indol-7-ylazamethylene)-4-oxo-1,3-thiazolidin-5-ylidene]methyl}-1,3-thiazol-2-yl)carbamoyl]propionic acid | 441.4 |

TABLE 7-continued

| | | | |
|---|---|---|---|
| 42 | | (5Z)-3-[N-(5-{[2-(indan-4-ylazamethylene)-4-oxo-1,3-thiazolidin-5-ylidene]methyl}-1,3-thiazol-2-yl)carbamoyl]propionic acid | 442.5 |
| 43 | | (5Z)-3-[N-(5-{[2-(benzimidazol-2-ylazamethylene)-4-oxo-1,3-thiazolidin-5-ylidene]methyl}-1,3-thiazol-2-yl)carbamoyl]propionic acid | 443.2 |
| 44 | | (5Z)-3-{N-[5-({2-[(1-methylbenzimidazol-2-yl)azamethylene]-4-oxo-1,3-thiazolidin-5-ylidene}methyl)-1,3-thiazol-2-yl]carbamoyl}propionic acid | 455.4 |
| 45 | | (2Z,5Z)-3-{N-[5-({2-[(2,3-dichlorophenyl)azamethylene]-4-oxo-1,3-thiazolidin-5-ylidene}methyl)-1,3-thiazol-2-yl]carbamoyl}propionic acid | 469.3 |
| 46 | | (2Z,5Z)-3-{N-[5-({2-[(2,4-dichlorophenyl)azamethylene]-4-oxo-1,3-thiazolidin-5-ylidene}methyl)-1,3-thiazol-2-yl]carbamoyl}propionic acid | 469.6 |

TABLE 7-continued

| | | | |
|---|---|---|---|
| 47 | 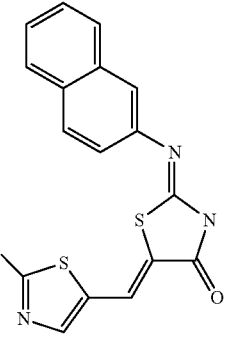 | (5Z)-3-[N-(5-{[2-(2-naphthylazamethylene)-4-oxo-1,3-thiazolidin-5-ylidene]methyl}-1,3-thiazol-2-yl)carbamoyl]propionic acid | 451.4 |
| 48 | 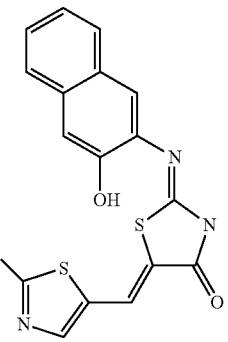 | (5Z)-3-{N-[5-({2-[(3-hydroxy(2-naphthyl))azamethylene]-4-oxo-1,3-thiazolidin-5-ylidene}methyl)-1,3-thiazol-2-yl]carbamoyl}propionic acid | 467.4 |

| Compound No. | 1H NMR | HPLC |
|---|---|---|
| 41 | $^1$H NMR (300 MHz, DMSO-d6) δ = 12.52(s, 1H), 11.06(s, 1H), 7.94(s, 1H), 7.85(s, 1H), 7.40(d, J = 7.8 Hz, 1H), 7.29(s, 1H), 7.02(t, J = 7.5 Hz, 1H), 6.72(d, J = 7.5 Hz, 1H), 6.47(s, 1H), 2.64-2.60(m, 2H), 2.53-2.51(m, 2H) | B Method 10.993 |
| 42 | $^1$H NMR (300 MHz, DMSO-d6) δ = 7.96(s, 1H), 7.85(s, 1H), 7.19-7.08(m, 2H), 6.76(bs, 1H), 2.98-2.90(m, 2H), 2.72-2.60(m, 4H), 2.56-2.47(m, 2H), 2.02-1.97(m, 2H) | B Method 11.953 |
| 43 | $^1$H NMR (300 MHz, DMSO-d6 + TFA) δ = 8.05(s, 1H), 8.02(s, 1H), 7.62-7.57(m, 2H), 7.35-7.32(m, 2H), 2.69(m, 2H), 2.57(m, 2H) | B Method 10.60 |
| 44 | $^1$H NMR (300 MHz, DMSO-d6 + TFA) δ = 8.32(bs, 1H), 8.02(s, 1H), 7.73-7.59(m, 2H), 7.38-7.35(m, 2H), 2.69(m, 2H), 2.58(m, 2H), 2.19(s, 3H) | A Method 6.05 |
| 45 | $^1$H NMR (300 MHz, DMSO-d6 + TFA) δ = 7.99(s, 1H), 7.88(s, 1H), 7.44(dd, J = 8.3 Hz, J = 8.2 Hz, 1H), 7.33(d, J = 8.2 Hz, 1H), 7.18(d, J = 8.3 Hz, 1H), 2.66(bm, 2H), 2.55(bm, 2H), | B Method 10.18 |
| 46 | $^1$H NMR (300 MHz, DMSO-d6 + TFA) δ = 7.99(s, 1H), 7.88(s, 1H), 7.71(bs, 1H), 7.53(m, 1H), 7.14(d, J = 6.7 Hz, 1H), 2.66(bm, 2H), 2.55(bm, 2H) | A Method 7.89 |
| 47 | $^1$H NMR (300 MHz, DMSO-d6 + TFA) δ = 8.04-7.79(m, 5H), 7.57-7.40(m, 4H), 2.73(m, 2H), 2.58(m, 2H) | B Method 12.30 |
| 48 | $^1$H NMR (300 MHz, DMSO-d6 + TFA) δ = 7.95(s, 1H), 7.86(s, 1H), 7.77-7.62(m, 2H), 7.44-7.23(m, 4H), 2.77-2.51(m, 4H) | B Method 11.26 |

TABLE 8

| Compound No. | Structure | Name | Dtctd Mass |
|---|---|---|---|
| 49 | 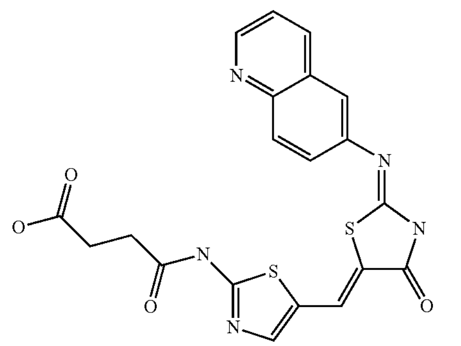 | (5Z)-3-[N-(5-{[4-oxo-2-(6-quinolylazamethylene)-1,3-thiazolidin-5-ylidene]methyl}-1,3-thiazol-2-yl)carbamoyl]propionic acid | 453.6 |
| 50 | 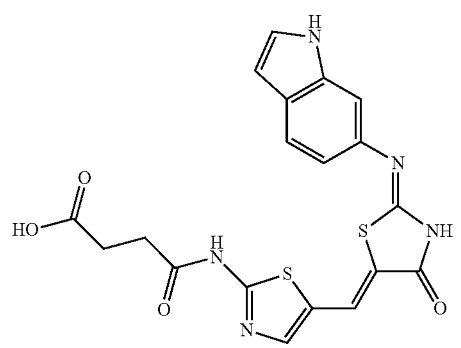 | (5Z)-3-[N-(5-{[2-(indol-6-ylazamethylene)-4-oxo-1,3-thiazolidin-5-ylidene]methyl}-1,3-thiazol-2-yl)carbamoyl]propionic acid | 441.8 |
| 51 | 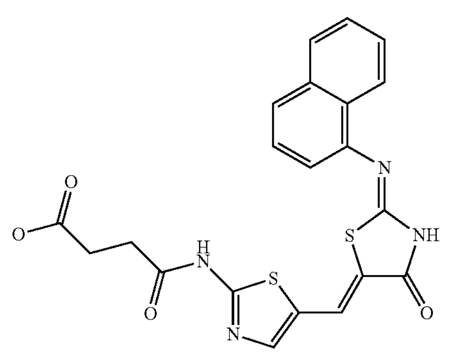 | (5Z)-3-[N-(5-{[2-(naphthylazamethylene)-4-oxo-1,3-thiazolidin-5-ylidene]methyl}-1,3-thiazol-2-yl)carbamoyl]propionic acid | 452.9 |
| 52 | 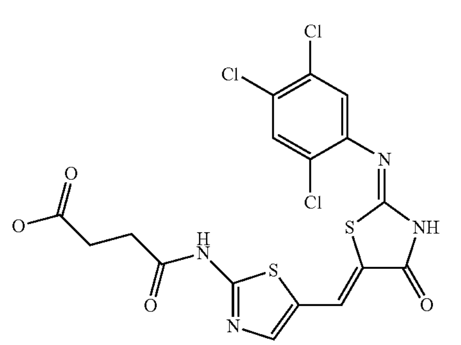 | (2Z,5Z)-3-{N-[5-({4-oxo-2-[(2,4,5-trichlorophenyl)azamethylene]-1,3-thiazolidin-5-ylidene}methyl)-1,3-thiazol-2-yl]carbamoyl}propionic acid | 505.4 |

TABLE 8-continued

| | | | |
|---|---|---|---|
| 53 | 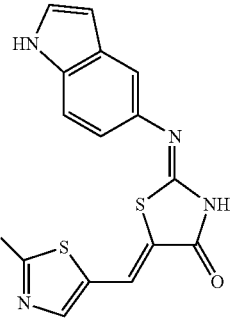 | (5Z)-5-[(2-{[2-(dimethylamino)ethyl]amino}(1,3-thiazol-5-yl))methylene]-2-(indol-5-ylazamethylene)-1,3-thiazolidin-4-one | 412.9 |
| 54 | 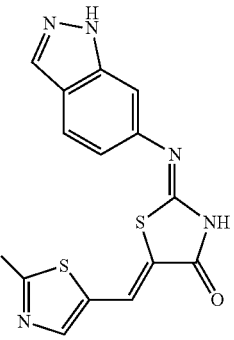 | (5Z)-5-[(2-{[2-(dimethylamino)ethyl]amino}(1,3-thiazol-5-yl))methylene]-2-(1H-indazol-6-ylazamethylene)-1,3-thiazolidin-4-one | 414.4 |
| 55 | 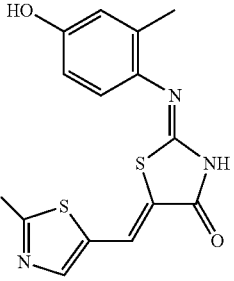 | (2Z,5Z)-5-[(2-{[2-(dimethylamino)ethyl]amino}(1,3-thiazol-5-yl)methylene]-2-[(4-hydroxy-2-methylphenyl)azamethylene]-1,3-thiazolidin-4-one | 404.0 |
| 56 | 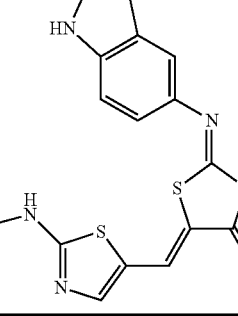 | (5Z)-5-[(2-{[3-(dimethylamino)propyl]amino}(1,3-thiazol-5-yl))methylene]-2-(indol-5-ylazamethylene)-1,3-thiazolidin-4-one | 426.9 |

| Compound No. | 1H NMR | HPLC |
|---|---|---|
| 49 | $^1$H NMR (300 MHz, DMSO-d6 + TFA) δ = 8.81(s, 1H), 8.26-7.79(m, 4H), 7.51-7.38(m, 2H), 7.10(s, 1H), 2.78-2.50(m, 4H) | B Method 8.197 |
| 50 | $^1$H NMR (300 MHz, DMSO-d6) δ = 12.53(s, 1H), 11.20(s, 1H), 8.18(s, 1H), 7.97-7.83(m, 2H), 7.59-7.51(m, 1H), 7.35(s, 1H), 7.17-7.13(m, 1H), 6.76(d, J = 7.8 Hz, 1H), 6.42(d, J = 9.6 Hz, 1H), 2.71-2.69(m, 2H), 2.63-2.58(m, 2H) | B Method 10.639 |
| 51 | $^1$H NMR (300 MHz, DMSO-d6) δ = 12.52(s, 1H), 7.96-7.88(m, 4H), 7.77(d, J = 8.1 Hz, 1H), 7.57-7.50(m, 3H), 7.13(d, J = 7.2 Hz, 1H), 2.62-2.58(m, 2H), 2.55-2.49(m, 2H) | B Method 12.015 |
| 52 | $^1$H NMR (300 MHz, DMSO-d6) δ = 12.62(s, 1H), 8.01(s, 1H), 7.93(bs, 2H), 7.51(s, 1H), 2.66- | B Method 13.317 |

TABLE 8-continued

| | | | |
|---|---|---|---|
| | | 2.64(m, 2H), 2.55-2.49(m, 2H) | |
| | 53 | ¹H NMR (300 MHz, DMSO-d6) δ = 11.19(bs, 1H), 9.42(bs, 1H), 8.06(s, 1H), 7.72-7.58(m, 2H), 7.44-7.28(m, 2H), 6.84(bs, 1H), 6.45(s, 1H), 3.63(bs, 1H), 3.42(bs, 2H), 2.77(bs, 6H) | B Method 6.75 |
| | 54 | ¹H NMR (300 MHz, DMSO-d6 + TFA) δ = 8.03(s, 1H), 7.76-7.60(m, 3H), 7.22(m, 2H), 3.66(bm, 2H), 3.27(bm, 2H), 2.79(s, 6H) | A Method 6.30 |
| | 55 | ¹H NMR (300 MHz, DMSO-d6) δ = 7.63(s, 1H), 7.55(s, 1H), 6.83(d, J = 8.4 Hz, 1H), 6.61(s, 1H), 6.59(dd, J = 2.4 Hz, J = 8.4 Hz, 1H), 3.66(bs, 2H), 3.22(bs, 2H), 2.77(bs, 6H), 2.05(s, 3H) | B Method 6.539 |
| | 56 | ¹H NMR (300 MHz, DMSO-d6) δ = 11.19(bs, 1H), 9.36(bs, 1H), 8.51(bs, 1H), 7.63-7.55(m, 2H), 7.42-7.26(m, 2H), 6.85(bs, 1H), 6.44(s, 1H), 3.21(bs, 2H), 3.12-3.01(m, 2H), 2.71(bs, 6H), 1.89-1.80(m, 2H) | B Method 7.070 |

TABLE 9

| Compound No. | Structure | Name | Dtctd Mass |
|---|---|---|---|
| 57 | 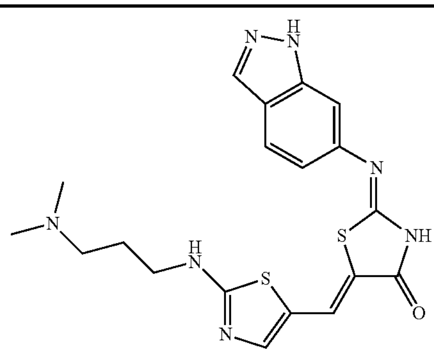 | (5Z)-5-[(2-{[3-(dimethylamino)propyl]amino}(1,3-thiazol-5-yl))methylene]-2-(1H-indazol-6-ylazamethylene)-1,3-thiazolidin-4-one | 428.0 |
| 58 | 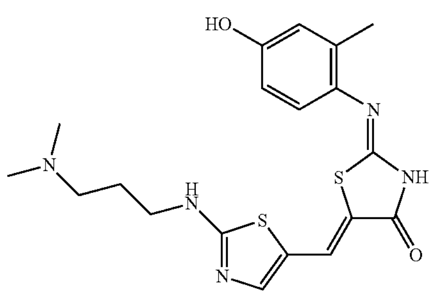 | (2Z,5Z)-5-[(2-{[3-(dimethylamino)propyl]amino}(1,3-thiazol-5-yl)methylene]-2-[(4-hydroxy-2-methylphenyl)azamethylene]-1,3-thiazolidin-4-one | 418.0 |
| 59 | 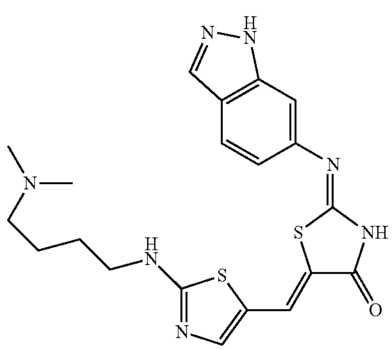 | (5Z)-5-[(2-{[4-(dimethylamino)butyl]amino}(1,3-thiazol-5-yl))methylene]-2-(1H-indazol-6-ylazamethylene)-1,3-thiazolidin-4-one | 442.3 |

TABLE 9-continued

| | | | |
|---|---|---|---|
| 60 | 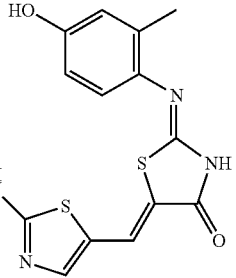 | (2Z,5Z)-5-[(2-{[4-(dimethylamino)butyl]amino}(1,3-thiazol-5-yl)methylene]-2-[(4-hydroxy-2-methylphenyl)azamethylene]-1,3-thiazolidin-4-one | 432.3 |
| 61 | 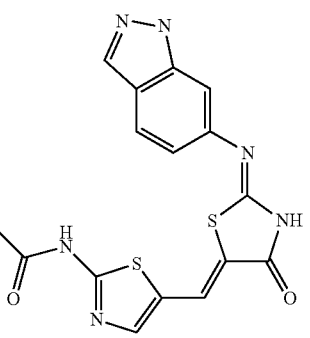 | (5Z)-4-(dimethylamino)-N-(5-{[2-(1H-indazol-6-yl)azamethylene)-4-oxo(1,3-thiazolidin-5-ylidene)]methyl}(1,3-thiazol-2-yl))butylamide | 455.4 |
| 62 | 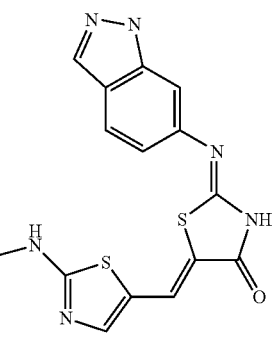 | (5Z)-3-(dimethylamino)-N-(5-{[2-(1H-indazol-6-yl)azamethylene)-4-oxo(1,3-thiazolidin-5-ylidene)]methyl}(1,3-thiazol-2-yl))propionamide | 447.8 |
| 63 | 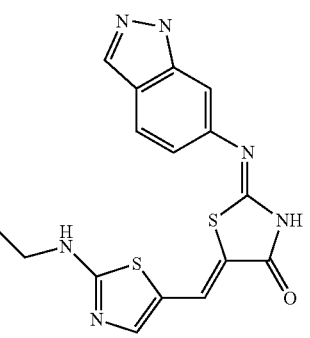 | (5Z)-2-(1H-indazol-6-ylazamethylene)-5-({2-[(3-morpholinopropyl)amino](1,3-thiazolidin-5-yl)}methylene)-1,3-thiazolidin-4-one | 470.0 |
| 64 | 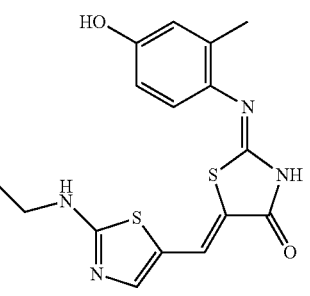 | (2Z,5Z)-2-[(4-hydroxy-2-methylphenyl)azamethylene]-5-({2-[(3-morpholinopropyl)amino](1,3-thiazol-5-yl)}methylene)-1,3-thiazolidin-4-one | 460.2 |

TABLE 9-continued

| Compound No. | 1H NMR | HPLC |
|---|---|---|
| 57 | ¹H NMR (300 MHz, DMSO-d6 + TFA) δ = 8.03(s, 1H), 7.78-7.60(m, 3H), 7.21(m, 2H), 3.24(bm, 2H), 3.08(bm, 2H), 2.73(s, 6H), 1.89(m, 2H) | B Method 6.80 |
| 58 | ¹H NMR (300 MHz, DMSO-d6) δ = 7.73(s, 1H), 7.70(s, 1H), 6.87(d, J = 8.4 Hz, 1H), 6.67(s, 1H), 6.60(d, J = 8.4 Hz, 1H), 3.36(bs, 2H), 3.04(bs, 2H), 2.70(s, 6H), 2.04(s, 3H), 1.90(bs, 2H) | B Method 6.652 |
| 59 | ¹H NMR (300 MHz, DMSO-d6) δ = 8.33(bs, 1H), 8.01(s, 1H), 7.74(s, 1H), 7.71(s, 1H), 7.57(bm, 1H), 7.08(bm, 1H), 3.34(bm, 2H), 2.38-2.04(bm, 6H), 2.73(s, 6H), 1.46(m, 4H) | B Method 7.01 |
| 60 | ¹H NMR (300 MHz, CD3OD) δ = 8.23(bs, 1H), 7.53(s, 1H), 7.48(s, 1H), 6.75(d, J = 8.4 Hz, 1H), 6.64(s, 1H), 6.57(d, J = 8.4 Hz, 1H), 3.21(t, J = 6.9 Hz, 2H), 2.84(s, 3H), 2.37(s, 6H), 2.15(d, J = 6.9 Hz, 2H), 1.44(m, 4H) | B Method 6.76 |
| 61 | ¹H NMR (300 MHz, CD3OD) δ = 13.06(bs, 1H), 8.02(s, 1H), 7.88(d, J = 6.0 Hz, 1H), 7.76(m, 2H), 7.17(d, J = 9.3 Hz, 1H), 6.79(d, J = 8.1 Hz, 1H), 2.48(t, J = 1.8 Hz, 2H), 2.31(m, 2H), 1.78(s, 3H), 1.75(s, 3H), 1.69(m, 2H) | B Method 7.01 |
| 62 | ¹H NMR (300 MHz, CD3OD) δ = 13.02(bs, 1H), 8.02(s, 1H), 7.81-7.42(m, 3H), 7.18(m, 1H), 6.78(bs, 1H), 3.47-3.24(m, 4H), 2.49(s, 6H) | A Method 6.23 |
| 63 | ¹H NMR (300 MHz, DMSO-d6) δ = 9.66(bs, 1H), 8.07(bs, 1H), 7.71(bs, 3H), 7.17(bs, 1H), 6.79(bs, 1H), 3.91(bs, 2H), 3.62(bs, 2H), 3.35(bs, 2H), 3.11(bs, 4H), 1.92(bs, 2H) | B Method 6.718 |
| 64 | ¹H NMR (300 MHz, DMSO-d6) δ = 9.64(bs, 1H), 8.51(bs, 1H), 7.68(s, 1H), 7.63(s, 1H), 6.83(d, J = 3.3 Hz, 1H), 6.68(s, 1H), 6.60(d, J = 7.8 Hz, 1H), 3.92(bs, 2H), 3.58(bs, 2H), 3.34(bs, 4H), 3.15(bs, 4H), 2.06(s, 3H), 1.67-1.63(m, 2H) | B Method 6.593 |

TABLE 10

| Compound No. | Structure | Name | Dtctd Mass |
|---|---|---|---|
| 65 | 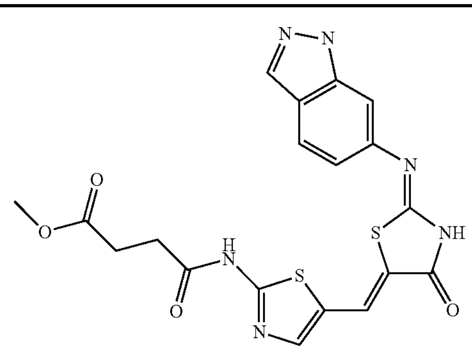 | (5Z)-methyl 3-[N-(5-{[2-(1H-indazol-6-ylazamethylene)-4-oxo-1,3-thiazolidin-5-ylidene]methyl}-1,3-thiazol-2-yl)carbamoyl]propanoate | 457.0 |
| 66 | 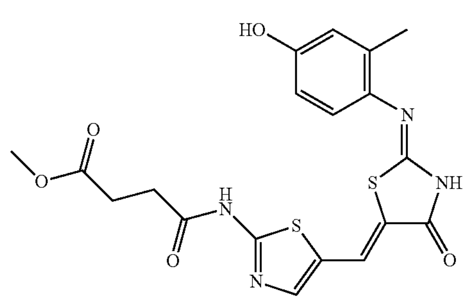 | (2Z,5Z)-methyl 3-{N-[5-({2-[(4-hydroxy-2-methylphenyl)azamethylene]-4-oxo-1,3-thiazolidin-5-ylidene}methyl)-1,3-thiazol-2-yl]carbamoyl}propanoate | 446.9 |

TABLE 10-continued

| 67 | 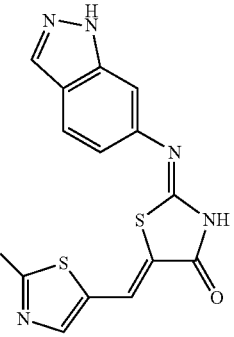 | (5Z)-2-(1H-indazol-6-ylazamethylene)-5-({2-[(3-(1-pyrroridinyl)propyl)amino](1,3-thiazol-5-yl)}methylene)-1,3-thiazolidin-4-one | 454.3 |
| 68 | 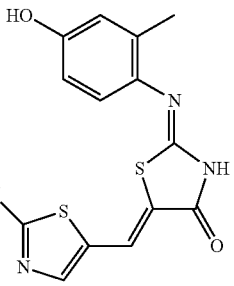 | (2Z,5Z)-2-[(4-hydroxy-2-methylphenyl)azamethylene]-5-({2-[(3-(1-pyrroridinyl)propyl)amino](1,3-thiazol-5-yl)}methylene)-1,3-thiazolidin-4-one | 444.3 |
| 69 | 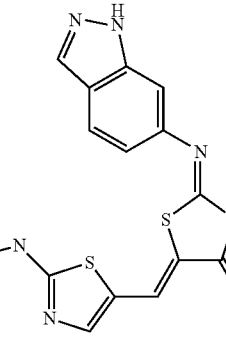 | (5Z)-N-(5-{[2-(1H-indazol-6-ylazamethylene)-4-oxo(1,3-thiazolidin-5-ylidene)]methyl}(1,3-thiazol-2-yl))-2-(4-methylpiperazinyl)acetamide | 483.0 |
| 70 | 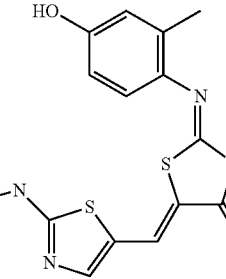 | (2Z,5Z)-N-[5-({2-[(4-hydroxy-2-methylphenyl)azamethylene]-4-oxo(1,3-thiazolidin-5-ylidene)}methyl)(1,3-thiazol-2-yl)]-2-(4-methylpiperazinyl)acetamide | 472.9 |
| 71 | 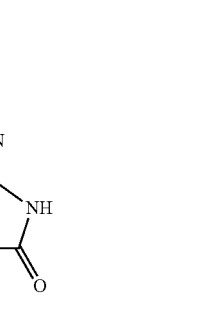 | (5Z)-5-[(2-amino(1,3-thiazol-5-yl))methylene]-2-(1H-indazol-6-ylazamethylene)-1,3-thiazolidin-4-one | 343.1 |

TABLE 10-continued

| | | | |
|---|---|---|---|
| 72 | (structure) | (2Z,5Z)-5-[(2-amino(1,3-thiazol-5-yl))methylene]-2-[(4-hydroxy-2-methylphenyl)azamethylene]-1,3-thiazolidin-4-one | 333.1 |

| Compound No. | 1H NMR | HPLC |
|---|---|---|
| 65 | $^1$H NMR (300 MHz, DMSO-d6) δ = 13.04(bs, 1H), 8.31(bs, 1H), 8.03(bs, 2H), 7.88(bs, 1H), 7.79-7.74(m, 2H), 7.10(bs, 1H), 6.79(d, J = 8.1 Hz, 1H), 3.54(s, 3H), 2.71-2.52(m, 4H) | B Method 10.747 |
| 66 | $^1$H NMR (300 MHz, DMSO-d6) δ = 7.92(s, 1H), 7.79(s, 1H), 6.85(d, J = 8.1 Hz, 1H), 6.69(s, 1H), 6.64(d, J = 8.1 Hz, 1H), 3.57(s, 3H), 2.70-2.64(m, 2H), 2.62-2.59(m, 2H), 2.07(s, 3H) | B Method 10.431 |
| 67 | $^1$H NMR (300 MHz, DMSO-d6) δ = 9.51(bs, 1H), 8.37(bs, 1H), 8.03(s, 1H), 7.75-7.66(m, 2H), 7.11(bs, 1H), 6.80(bs, 1H), 3.50(bs, 2H), 3.31(bs, 2H), 3.14(bs, 2H), 2.95(bs, 2H), 1.96(bs, 6H) | B Method 7.005 |
| 68 | $^1$H NMR (300 MHz, DMSO-d6) δ = 9.48(bs, 1H), 7.71(d, J = 4.2 Hz, 2H), 6.87(d, J = 8.4 Hz, 1H), 6.68(s, 1H), 6.61(dd, J = 2.7 Hz, J = 8.7 Hz, 1H), 3.50(bs, 2H), 3.36(t, J = 6.6 Hz, 2H), 3.16-3.09(m, 2H), 2.94(bs, 2H), 2.06(s, 3H), 1.99-1.81(m, 6H) | B Method 6.711 |
| 69 | $^1$H NMR (300 MHz, DMSO-d6) δ = 8.07-7.88(m, 3H), 7.74(bs, 1H), 7.13(s, 1H), 6.80(d, J = 9.0 Hz, 1H), 4.22(s, 2H), 3.42(bs, 8H), 2.83(s, 3H) | B Method 6.939 |
| 70 | $^1$H NMR (300 MHz, DMSO-d6) δ = 7.98(s, 1H), 7.84(s, 1H), 6.85(d, J = 8.4 Hz, 1H), 6.69(bs, 1H), 6.62(dd, J = 2.4 Hz, J = 8.4 Hz, 1H), 4.26(s, 2H), 3.45(bs, 8H), 2.85(s, 3H), 2.06(s, 3H) | B Method 6.763 |
| 71 | $^1$H NMR (300 MHz, DMSO-d6) δ = 12.96(bs, 1H), 8.30(s, 1H), 8.02(s, 1H), 7.78(bs, 1H), 7.76-7.50(m, 4H), 7.12(s, 1H), 6.76(bs, 1H) | B Method 9.24 |
| 72 | $^1$H NMR (300 MHz, DMSO-d6) δ = 9.36(bs, 1H), 7.72(bs, 2H), 7.62(s, 1H), 7.49(s, 1H), 6.83(d, J = 8.1 Hz, 1H), 6.67(s, 1H), 6.60(d, J = 8.1 Hz, 1H), 2.05(s, 3H) | B Method 8.87 |

TABLE 11

| Compound No. | Structure | Name | Dtctd Mass |
|---|---|---|---|
| 73 | (structure) | (5Z)-cyclopropyl-N-(5-{[2-(1H-indazol-6-ylazamethylene)-4-oxo(1,3-thiazolidin-5-ylidene)]methyl}(1,3-thiazol-2-yl))carboxamide | 41.1 |

TABLE 11-continued

| | | | |
|---|---|---|---|
| 74 | | (2Z,5Z)-5-cyclopropyl-N-[5-({2-[(4-hydroxy-2-methylphenyl)azamethylene]-4-oxo(1,3-thiazolidin-5-ylidene)}methyl)(1,3-thiazol-2-yl)]carboxamide | 401.5 |
| 75 | | (5Z)-N-(5-{[2-(1H-indazol-6-ylazamethylene)-4-oxo-1,3-thiazolidin-5-ylidene]methyl}-1,3-thiazol-2-yl)acetamide | 385.1 |
| 76 | | (5Z)-N-[5-({2-[(1-methyl(1H-indazol-6-yl))azamethylene]-4-oxo-1,3-thiazolidin-5-ylidene}methyl)-1,3-thiazol-2-yl]acetamide | 399.0 |
| 77 | | (5Z)-N-[5-({2-[(1-methylindol-5-yl)azamethylene]-4-oxo-1,3-thiazolidin-5-ylidene}methyl)-1,3-thiazol-2-yl]acetamide | 398.0 |
| 78 | | (5Z)-N-[5-({2-[(1-methylindol-6-yl)azamethylene]-4-oxo-1,3-thiazolidin-5-ylidene}methyl)-1,3-thiazol-2-yl]acetamide | 398.0 |

TABLE 11-continued

| # | Structure | Name | Mass |
|---|---|---|---|
| 79 | 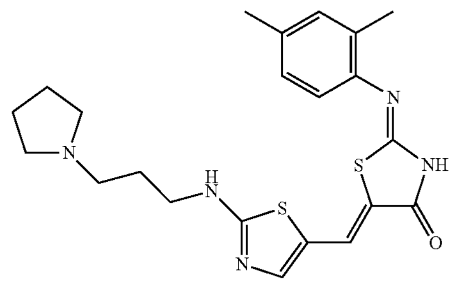 | (2Z,5Z)-2-[(2,4-dimethylphenyl)azamethylene]-5-({2-[(3-pyrrolidinylpropyl)amino](1,3-thiazol-5-yl)}methylene)-1,3-thiazolidin-4-one | 442.2 |
| 80 | 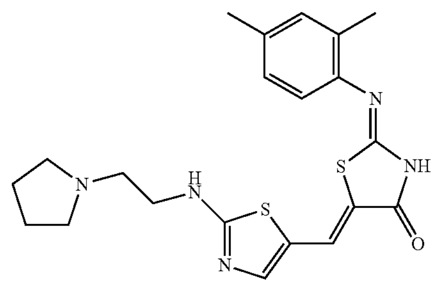 | (2Z,5Z)-2-[(2,4-dimethylphenyl)azamethylene]-5-({2-[(2-pyrrolidinylethyl)amino](1,3-thiazol-5-yl)}methylene)-1,3-thiazolidin-4-one | 428.2 |

| Compound No. | 1H NMR | HPLC |
|---|---|---|
| 73 | $^1$H NMR (300 MHz, DMSO-d6) δ = 13.06(bs, 1H), 13.01(bs, 1H), 12.76(bs, 1H), 8.35(s, 1H), 8.03-7.74(m, 3H), 7.17(bm, 1H), 6.79(bs, 1H), 1.94(m, 1H), 0.88(m, 4H) | A Method 7.60 |
| 74 | $^1$H NMR (300 MHz, DMSO-d6) δ = 9.38(bs, 1H), 7.92(bs, 2H), 7.79(d, J = 1.5, 1H), 6.85(s, 1H), 6.62(d, J = 8.4 Hz, 1H), 2.05(s, 3H), 1.92(m, 1H), 0.89(s, 4H) | A Method 7.45 |
| 75 | $^1$H NMR (300 MHz, DMSO-d6) δ = 8.03(bs, 1H), 7.91-7.70(m, 3H), 7.16(s, 1H), 6.84(bs, 1H), 2.14(s, 3H) | B Method 10.145 |
| 76 | $^1$H NMR (300 MHz, DMSO-d6) δ = 7.99(s, 1H), 7.93-7.84(m, 2H), 7.75(d, J = 8.4 Hz, 1H), 7.23(bs, 1H), 6.83(bs, 1H), 3.99(s, 3H), 2.08(s, 3H) | B Method 11.311 |
| 77 | $^1$H NMR (300 MHz, DMSO-d6) δ = 12.31(bs, 1H), 8.07-7.80(m, 2H), 7.50-7.28(m, 3H), 6.91(s, 1H), 6.46-6.43(m, 1H), 3.81(s, 3H), 2.10(s, 3H) | B Method 11.861 |
| 78 | $^1$H NMR (300 MHz, DMSO-d6) δ = 12.41(bs, 1H), 8.01-7.81(m, 3H), 7.58-7.54(m, 1H), 7.35-7.15(m, 2H), 6.42(bs, 1H), 3.76(s, 3H), 2.13(s, 3H) | B Method 12.086 |
| 79 | $^1$H NMR (300 MHz, CD$_3$OD) δ = 7.66(s, 1H), 7.47(bs, 1H), 7.12(s, 1H) 7.05(d, J = 7.5 Hz, 1H), 6.94(bs, 1H), 3.44(bs, 2H), 3.21(bs, 4H), 2.34(s, 3H), 2.18(bs, 5H), 2.05(bs, 6H) | B Method 10.765 |
| 80 | $^1$H NMR (300 MHz, DMSO-d6) δ = 7.71(s, 1H), 7.64(s, 1H), 7.07(s, 1H), 7.00(d, J = 8.1 Hz, 1H), 6.82(d, J = 7.5 Hz, 1H), 3.64(bs, 2H), 3.56(bs, 2H), 3.35(bs, 2H), 3.02(bs, 2H), 2.26(s, 3H), 2.08(s, 3H), 1.98(bs, 2H), 1.83(bs, 2H) | B Method 10.772 |

TABLE 12

| Compound No. | Structure | Name | Dtctd Mass |
|---|---|---|---|
| 81 | 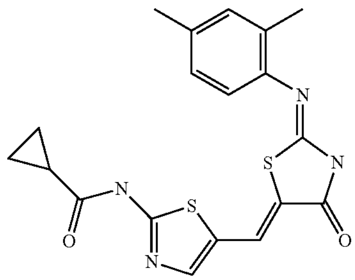 | (2Z,5Z)-N-[5-({2-[(2,4-dimethylphenyl)azamethylene]-4-oxo(1,3-thiazolidin-5-ylidene)}methyl)(1,3-thiazol-2-yl)]cyclopropylcarboxamide | 399.1 |
| 82 | 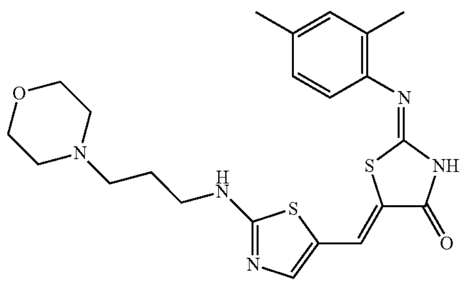 | (2Z,5Z)-2-[(2,4-dimethylphenyl)azamethylene]-5-({2-[(3-morpholinopropyl)amino](1,3-thiazol-5-yl)}methylene)-1,3-thiazolidin-4-one | 458.2 |
| 83 | 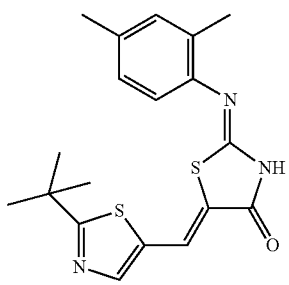 | (2Z,5Z)-5-{[2-(tert-butyl)(1,3-thiazol-5-yl)]methylene}-2-[(2,4-dimethylphenyl)azamethylene]-1,3-thiazolidin-4-one | 372.1 |
| 84 | 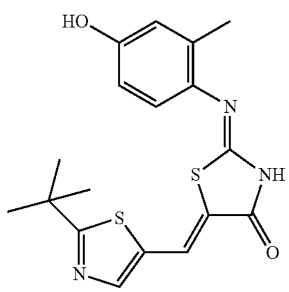 | (2Z,5Z)-5-{[2-tert-butyl)(1,3-thiazol-5-yl)]methylene}-2-[(4-hydroxy-2-methylphenyl)azamethylene]-1,3-thiazolidin-4-one | 374.1 |
| 85 | 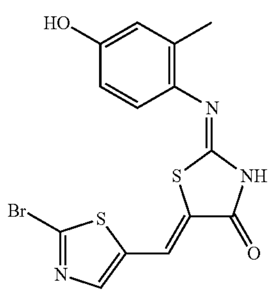 | (2Z,5Z)-5-{[(2-bromo(1,3-thiazol-5-yl))methylene]-2-[(4-hydroxy-2-methylphenyl)azamethylene]-1,3-thiazolidin-4-one | 397.8 |

TABLE 12-continued

| # | Structure | Name | MS |
|---|---|---|---|
| 86 | 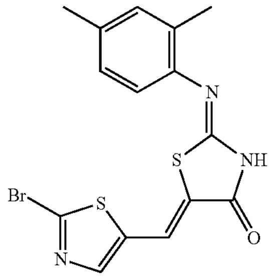 | (2Z,5Z)-2-[(2,4-dimethylphenyl)azamethylene]-5-[(2-bromo(1,3-thiazol-5-yl))methylene]-1,3-thiazolidin-4-one | 395.9 |
| 87 | 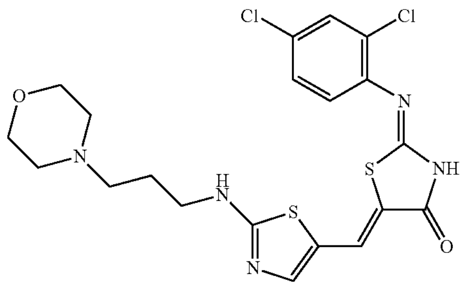 | (2Z,5Z)-2-[(2,4-dichlorophenyl)azamethylene]-5-({2-[(3-morpholinopropyl)amino](1,3-thiazol-5-yl)}methylene)-1,3-thiazolidin-4-one | 498.2 |
| 88 | 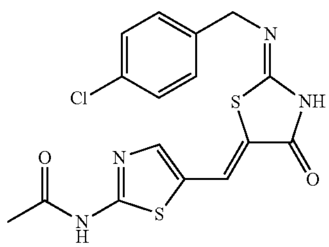 | (2Z,5Z)-N-[5-({2-[2-(4-chlorophenyl)-1-azaethylidene]-4-oxo-1,3-thiazolidin-5-ylidene}methyl)-1,3-thiazol-2-yl]acetamide | 393.1 |

| Compound No. | 1H NMR | HPLC |
|---|---|---|
| 81 | $^1$H NMR (300 MHz, DMSO-d6) δ = 12.80(bs, 1H), 12.21(bs, 1H), 7.97(s, 1H), 7.85(s, 1H), 7.10(s, 1H), 7.04(d, J = 7.8 Hz, 1H), 6.84(d, J = 7.2 Hz, 1H), 2.30(s, 3H), 2.10(s, 3H), 1.94(bs, 1H), 0.91(bs, 4H) | B Method 13.358 |
| 82 | $^1$H NMR (300 MHz, DMSO-d6) δ = 7.70(s, 1H), 7.37(s, 1H), 7.08(s, 1H), 7.05(d, J = 8.1 Hz, 1H), 6.91(d, J = 7.5 Hz, 1H), 3.82(bs, 4H), 3.44(bd, 2H), 2.65(bs, 6H), 2.35(s, 3H), 2.20(s, 3H), 1.93(bs, 2H) | B Method 10.530 |
| 83 | $^1$H NMR (300 MHz, CD$_3$OD) δ = 7.92(s, 1H), 7.83(s, 1H), 7.10(s, 1H), 7.04(d, J = 8.1 Hz, 1H), 6.98(d, J = 8.1 Hz, 1H), 2.32(s, 3H), 2.17(s, 3H), 1.39(s, 9H) | B Method 16.406 |
| 84 | $^1$H NMR (300 MHz, DMSO-d6) δ = 8.02(s, 1H), 7.81(s, 1H), 6.84(d, J = 8.7 Hz, 1H), 6.67(s, 1H), 6.61(d, J = 8.4 Hz, 1H), 2.05(s, 3H), 1.30(s, 9H) | B Method 13.089 |
| 85 | $^1$H NMR (300 MHz, DMSO-d6) δ = 9.53(bs, 1H), 8.18(s, 1H), 8.08(s, 1H), 7.86(s, 2H), 6.64(m, 3H), 2.08(s, 3H) | B Method 12.05 |
| 86 | $^1$H NMR (300 MHz, DMSO-d6) δ = 8.08(s, 1H), 7.86(s, 1H), 7.09(s, 1H), 7.02(d, J = 8.4 Hz, 1H), 6.85(bs, 1H), 2.28(s, 3H), 2.08(s, 3H) | B Method 15.790 |
| 87 | $^1$H NMR (300 MHz, DMSO-d6) δ = 7.76(s, 1H), 7.68(s, 1H), 7.66(bs, 1H), 7.41(dd, J = 3.0 Hz, J = 9.0 Hz, 1H), 7.13(d, J = 6.0 Hz, 1H), 3.92(bs, 2H), 3.60(bs, 2H), 3.42-3.32(m, 4H), 3.12(t, J = 8.1 Hz, 2H), 3.02(bs, 2H), 1.98-1.87(m, 2H) | B Method 11.073 |
| 88 | $^1$H NMR (300 MHz, DMSO-d6) δ = 7.93(s, 1H), 7.79(s, 1H), 7.43(d, J = 8.4 Hz, 1H), 7.34(d, J = 8.4 Hz, 1H), 4.69(s, 2H), 2.16(s, 3H) | A Method 8.02 |

TABLE 13

| Compound No. | Structure | Name | Dtctd Mass |
|---|---|---|---|
| 89 | 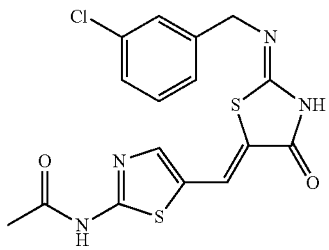 | (2Z,5Z)-N-[5-({2-[2-(3-chlorophenyl)-1-azaethylidene]-4-oxo-1,3-thiazolidin-5-ylidene}methyl)-1,3-thiazol-2-yl]acetamide | 393.3 |
| 90 | 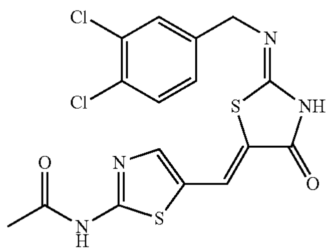 | (2Z,5Z)-N-[5-({2-[2-(3,4-dichlorophenyl)-1-azaethylidene]-4-oxo-1,3-thiazolidin-5-ylidene}methyl)-1,3-thiazol-2-yl]acetamide | 427.0 |
| 91 | 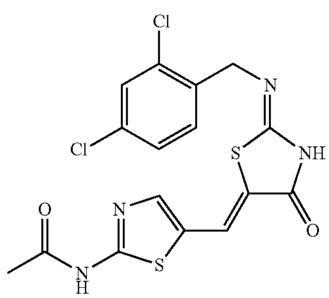 | (2Z,5Z)-N-[5-({2-[2-(2,4-dichlorophenyl)-1-azaethylidene]-4-oxo-1,3-thiazolidin-5-ylidene}methyl)-1,3-thiazol-2-yl]acetamide | 427.0 |
| 92 | 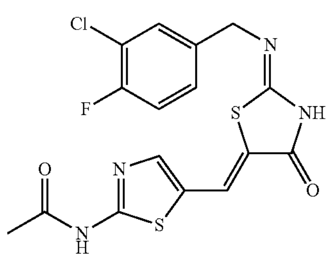 | (2Z,5Z)-N-[5-({2-[2-(3-chloro-4-fluorophenyl)-1-azaethylidene]-4-oxo-1,3-thiazolidin-5-ylidene}methyl)-1,3-thiazol-2-yl]acetamide | 411.1 |
| 93 | 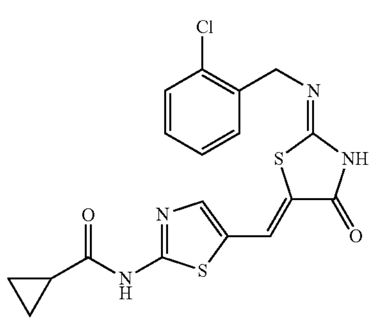 | (2Z,5Z)-N-[5-({2-[2-(2-chlorophenyl)-1-azaethylidene]-4-oxo(1,3-thiazolidin-5-ylidene)}methyl)(1,3-thiazol-2-yl)]cyclopropylcarboxamide | 419.1 |

TABLE 13-continued

| | | | |
|---|---|---|---|
| 94 | 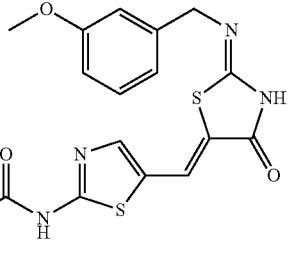 | (2Z,5Z)-cyclopropyl-N-[5-({2-[2-(3-methoxyphenyl)-1-azaethylidene]-4-oxo(1,3-thiazolidin-5-ylidene)}methyl)(1,3-thiazol-2-yl)]carboxamide | 415.1 |
| 95 | 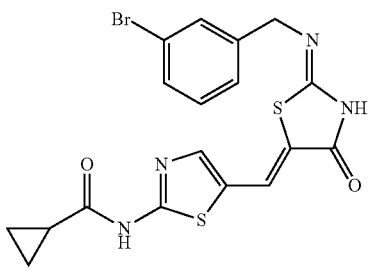 | (2Z,5Z)-N-[5-({2-[2-(3-bromophenyl)-1-azaethylidene]-4-oxo(1,3-thiazolidin-5-ylidene)}methyl)(1,3-thiazol-2-yl)]cyclopropylcarboxamide | 465.2 |
| 96 | 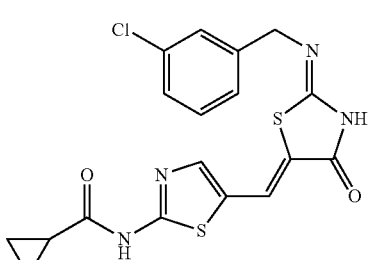 | (2Z,5Z)-N-[5-({2-[2-(3-chlorophenyl)-1-azaethylidene]-4-oxo(1,3-thiazolidin-5-ylidene)}methyl)(1,3-thiazol-2-yl)]cyclopropylcarboxamide | 419.2 |

| Compound No. | 1H NMR | HPLC |
|---|---|---|
| 89 | $^1$H NMR (300 MHz, DMSO-d6) δ = 7.94(s, 1H), 7.93(s, 1H), 7.82-7.27(m, 4H), 4.71(s, 2H), 2.16(s, 3H) | A Method 7.98 |
| 90 | $^1$H NMR (300 MHz, DMSO-d6) δ = 7.92(s, 1H), 7.80(s, 1H), 7.62(s, 1H), 7.60(s, 1H), 7.32(d, J = 8.1 Hz, 1H), 4.70(s, 2H), 2.16(s, 3H) | B Method 12.610 |
| 91 | $^1$H NMR (300 MHz, DMSO-d6) δ = 7.90(s, 1H), 7.79(s, 1H), 7.61(s, 1H), 7.43(s, 2H), 4.74(s, 2H), 2.15(s, 3H) | B Method 12.682 |
| 92 | $^1$H NMR (300 MHz, DMSO-d6) δ = 7.92(s, 1H), 7.80(s, 1H), 7.55(d, J = 6.3 Hz, 1H), 7.38-7.35(m, 2H), 4.69(s, 2H), 2.15(s, 3H) | B Method 12.121 |
| 93 | $^1$H NMR (300 MHz, DMSO-d6) δ = 7.92(s, 1H), 7.78(s, 1H), 7.42-7.32(m, 4H), 4.77(s, 2H), 1.98(m, 1H), 0.93(bs, 4H) | A Method 9.40 |
| 94 | $^1$H NMR (300 MHz, DMSO-d6) δ = 7.93(s, 1H), 7.78(s, 1H), 7.27(t, J = 8.1 Hz, 1H), 6.90-6.85(m, 2H), 4.67(s, 2H), 3.73(s, 3H), 1.96(bs, 1H), 0.92(bs, 4H) | B Method 12.114 |
| 95 | $^1$H NMR (300 MHz, DMSO-d6) δ = 7.94(s, 1H), 7.80(s, 1H), 7.54-7.48(m, 2H), 7.33(bs, 2H), 4.71(s, 2H), 1.98-1.94(m, 1H), 0.92(bs, 4H) | B Method 12.754 |
| 96 | $^1$H NMR (300 MHz, DMSO-d6) δ = 7.94(s, 1H), 7.80(s, 1H), 7.41-7.29(m, 4H), 4.72(s, 2H), 1.98-194(m, 1H), 0.92(bs, 4H) | B Method 12.619 |

TABLE 14

| Compound No. | Structure | Name | Dtctd Mass | 1H NMR | HPLC |
|---|---|---|---|---|---|
| 97 | 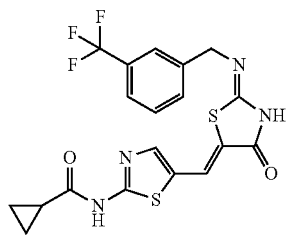 | (2Z,5Z)-cyclopropyl-N-{5-[(4-oxo-2-{2-[3-(trifluoromethyl)phenyl]-1-azaethylidene}(1,3-thiazolidin-5-ylidene))methyl](1,3-thiazol-2-yl)}carboxamide | 453.1 | $^1$H NMR (300 MHz, DMSO-d6) δ = 7.94 (s, 1H), 7.80 (s, 1H), 7.71-7.63 (m, 4H), 4.81 (s, 2H), 1.96 (bs, 1H), 0.92 (bs, 4H) | B Method 12.850 |
| 98 | 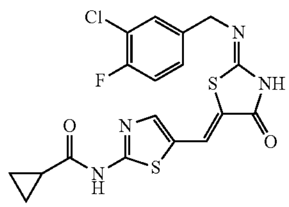 | (2Z,5Z)-N-[5-({2-[2-(3-chloro-4-fluorophenyl)-1-azaethylidene]-4-oxo(1,3-thiazolidin-5-ylidene)}methyl)(1,3-thiazol-2-yl)]cyclopropylcarboxamide | 437.2 | $^1$H NMR (300 MHz, DMSO-d6) δ = 7.94 (s, 1H), 7.80 (s, 1H), 7.57 (d, J = 7.8 Hz, 1H), 7.44-7.33 (m, 2H), 4.70 (s, 2H), 1.98-1.95 (m, 1H), 0.92 (bs, 4H) | B Method 12.719 |
| 99 | 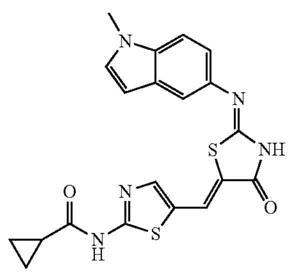 | (5Z)-cyclopropyl-N-[5-({2-[[(1-methylindol-5-yl)azamethylene]-4-oxo(1,3-thiazolidin-5-ylidene)}methyl)-1,3-thiazol-2-yl]carboxamide | 424.3 | $^1$H NMR (300 MHz, DMSO-d6) δ = 7.90 (s, 1H), 7.82 (s, 1H), 7.48-7.27 (m, 3H), 6.92 (dd, J = 1.8 Hz, J = 8.7 Hz, 1H), 6.43 (bs, 1H), 3.79 (s, 3H), 1.91-1.87 (m, 1H), 0.85 (bs, 4H) | B Method 12.479 |
| 100 | 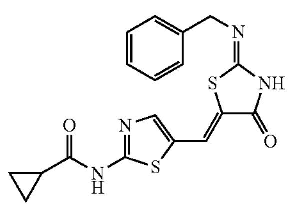 | (2Z,5Z)-cyclopropyl-N-(5-{[4-oxo-2-(2-phenyl-1-azaethylidene)(1,3-thiazolidin-5-ylidene)]methyl}(1,3-thiazol-2-yl))carboxamide | 385.2 | $^1$H NMR (300 MHz, DMSO-d6) δ = 8.15(s, 1H), 8.05(s, 1H), 7.84(s, 1H), 6.87 (m, 2H), 6.69-6.60(m, 3H), 1.98(m, 1H), 0.93(bs, 4H) | A Method 8.02 |
| 101 | 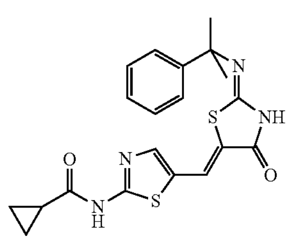 | (2Z,5Z)-cyclopropyl-N-(5-{[2-(2-methyl-2-phenyl-1-azapropylidene)-4-oxo(1,3-thiazolidin-5-ylidene)]methyl}(1,3-thiazol-2-yl))-carboxamide | 412.8 | No data | A Method 8.42 |
| 102 | 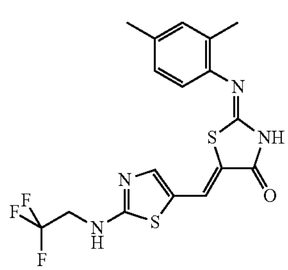 | (2Z,5Z)-2-[(2,4-dimethylphenyl)azamethylene]-5-({2-[(2,2,2-trifluoroethyl)amino](1,3-thiazol-5-yl)}methylene)-1,3-thiazolidin-4-one | 413.1 | $^1$H NMR (300 MHz, DMSO-d6) δ = 7.68 (s, 1H), 7.60 (s, 1H), 6.99 (d, J = 7.5 Hz, 1H), 6.81 (d, J = 7.5 Hz, 1H), 4.17 (m, 2H), 2.25 (s, 3H), 2.07 (s, 3H) | A Method 8.74 |

TABLE 14-continued

| Compound No. | Structure | Name | Dtctd Mass | 1H NMR | HPLC |
|---|---|---|---|---|---|
| 103 | 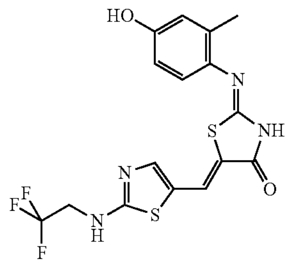 | (2Z,5Z)-2-[(4-hydroxy-2-methylphenyl)azamethylene]-5-({2-[(2,2,2-trifluoroethyl)amino}(1,3-thiazol-5-yl)}methylene)-1,3-thiazolidin-4-one | 415.1 | ¹H NMR (300 MHz, DMSO-d6) δ = 7.66 (s, 1H), 7.60 (s, 1H), 6.85 (d, J = 8.4 Hz, 1H), 6.68 (d, J = 2.7 Hz, 1H), 6.60 (dd, J = 3.0 Hz, J = 8.4 Hz, 1H), 4.17 (m, 2H), 2.05 (s, 3H) | A Method 7.63 |
| 104 | 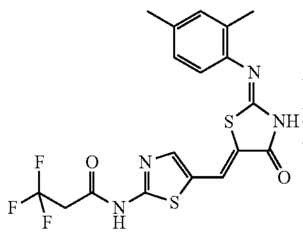 | (2Z,5Z)-N-[5-({2-[(2,4-dimethylphenyl)azamethylene]-4-oxo(1,3-thiazolidin-5-ylidene)}methyl)(1,3-thiazol-2-yl]-3,3,3-trifluoropropionamide | 441.2 | ¹H NMR (300 MHz, DMSO-d6) δ = 7.95 (s, 1H), 7.84 (s, 1H), 7.06 (s,1H), 7.03 (d, J = 6.0 Hz, 1H), 6.83 (d, J = 6.0 Hz, 1H), 3.68-3.58 (m, 2H), 2.26 (s, 3H), 2.08 (s, 3H) | B Method 13.035 |

TABLE 15

| Compound No. | Structure | Name | Dtctd Mass | 1H NMR | HPLC |
|---|---|---|---|---|---|
| 105 | 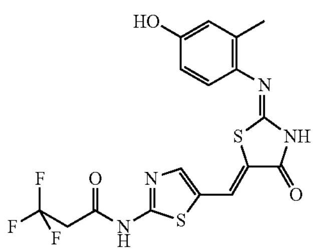 | (2Z,5Z)-3,3,3-trifluoro-N-[5-({2-[(4-hydroxy-2-methylphenyl)azamethylene]-4-oxo(1,3-thiazolidin-5-ylidene)}methyl)(1,3-thiazol-2-yl)]propionamide | 442.1 | ¹H NMR (300 MHz, DMSO-d6) δ = 8.32 (s, 1H), 8.08 (s, 1H), 6.90-6.64 (m, 3H), 4.23 (m, 2H), 2.08 (s, 3H) | B Method 10.03 |
| 106 | 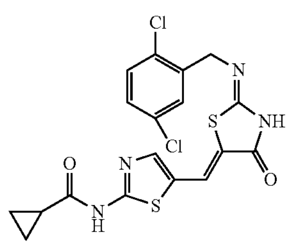 | (2Z,5Z)-N-[5-({2-[2-(2,5-dichlorophenyl)-1-azaethylidene]-4-oxo(1,3-thiazolidin-5-ylidene)}methyl)(1,3-thiazol-2-yl)]cyclopropylcarboxamide | 453.2 | ¹H NMR (300 MHz, DMSO-d6) δ = 7.92 (s, 1H), 7.80 (s, 1H), 7.52-7.42 (m, 3H), 4.75 (s, 2H), 1.98-1.92 (m, 1H), 0.92 (bs, 4H) | B Method 13.025 |
| 107 | 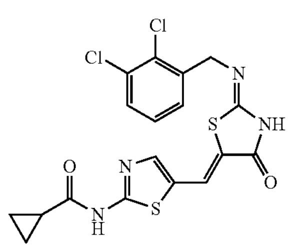 | (2Z,5Z)-N-[5-({2-[2-(2,3-dichlorophenyl)-1-azaethylidene]-4-oxo(1,3-thiazolidin-5-ylidene)}methyl)(1,3-thiazol-2-yl)]cyclopropylcarboxamide | 453.2 | ¹H NMR (300 MHz, DMSO-d6) δ = 7.93 (s, 1H), 7.80 (s, 1H), 7.59 (bs, 1H), 7.39 (bs, 2H), 4.80 (s, 2H), 1.96 (bs, 1H), 0.91 (bs, 4H) | B Method 13.066 |

TABLE 15-continued

| Compound No. | Structure | Name | Dtctd Mass | 1H NMR | HPLC |
|---|---|---|---|---|---|
| 108 | 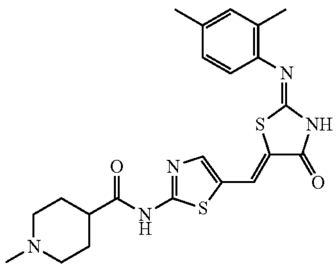 | (2Z,5Z)-N-[5-({2-[(2,4-dimethylphenyl)azamethylene]-4-oxo(1,3-thiazolidin-5-ylidene)}methyl)(1,3-thiazol-2-yl)](1-methyl(4-piperidyl))carboxamide | 456.3 | $^1$H NMR (300 MHz, DMSO-d6) δ = 7.91 (s, 1H), 7.79 (s, 1H), 7.08 (bs, 1H), 7.03 (d, J = 8.4 Hz, 1H), 6.81 (d, J =7.8 Hz, 1H), 2.80 (s, 2H), 2.44 (bs, 1H), 2.36 (s, 3H), 2.28 (s, 3H), 2.23 (s, 3H), 1.89 (t, J = 10.5 Hz, 2H), 1.75 (bs, 2H), 1.63 (bs, 2H) | A Method 7.08 |
| 109 | 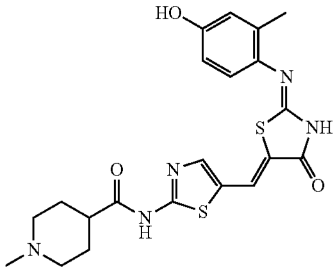 | (2Z,5Z)-N-[5-({2-[(4-hydroxy-2-methylphenyl)azamethylene]-4-oxo(1,3-thiazolidin-5-ylidene)}methyl)(1,3-thiazol-2-yl)](1-methyl(4-piperidyl))carboxamide | 458.4 | $^1$H NMR (300 MHz, DMSO-d6) δ = 7.93 (s, 1H), 7.80 (s, 1H), 6.91 (m, 2H), 6.81 (m, 1H), 3.77 (s, 3H), 2.79 (bs, 2H), 2.42 (bs, 1H), 2.16 (s, 3H), 2.12 (s, 3H), 1.87 (t, J = 10.5 Hz, 2H), 1.72 (bs, 2H), 1.61 (bs, 2H) | A Method 6.41 |
| 110 | 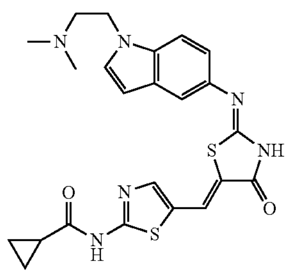 | (5Z)-N-(5-{[2-({1-[2-(dimethylamino)ethyl]indol-5-yl}azamethylene)-4-oxo(1,3-thiazolidin-5-ylidene)]methyl}(1,3-thiazol-2-yl))cyclopropylcarboxamide | 481.3 | $^1$H NMR (300 MHz, DMSO-d6) δ = 9.63 (bs, 1H), 7.92 (s, 1H), 7.83 (s, 1H), 7.60 (bs, 1H), 7.48-7.43 (m, 1H), 7.28 (bs, 1H), 6.95 (dd, J = 2.1 Hz, J = 9.0 Hz, 1H), 6.52 (d, J = 2.7 Hz, 1H), 4.57 (bs, 2H), 3.57-3.51 (m, 2H), 2.85 (bs, 2H), 1.99-1.87 (m, 1H), 0.94-0.82 (m, 4H) | B Method 10.443 |
| 111 | 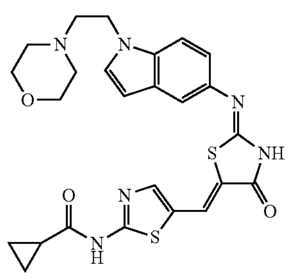 | (5Z)-cyclopropyl-N-{5-[(2-{[1-(2-morpholinoethyl)indol-5-yl]azamethylene}-4-oxo(1,3-thiazolidin-5-ylidene))methyl](1,3-thiazol-2-yl)}carboxamide | 523.1 | $^1$H NMR (300 MHz, DMSO-d6) δ = 7.92 (s, 1H), 7.80 (s, 1H), 7.50 (m, 2H), 7.44 (m, 2H), 6.45 (m, 1H), 4.29 (m, 4H), 3.57-3.48 (m, 2H), 2.69 (m, 2H), 2.41 (m, 4H), 2.01-1.86 (m, 1H), 0.94-0.82 (m, 4H) | A Method 6.96 |
| 112 | 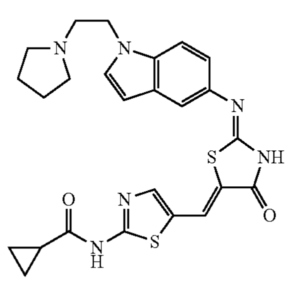 | (5Z)-cyclopropyl-N-{5-[(4-oxo-2-{[1-(2-(1-pyrrolidinyl)ethyl)indol-5-yl]azamethylene}-(1,3-thiazolidin-5-ylidene))methyl](1,3-thiazol-2-yl)}carboxamide | 507.4 | $^1$H NMR (300 MHz, DMSO-d6) δ = 7.91 (s, 1H), 7.79 (s, 1H), 7.51 (m, 2H), 7.44 (m, 2H), 6.45 (m, 1H), 4.29 (m, 2H), 2.83 (m, 2H), 2.49 (m, 4H), 1.94 (m, 1H), 1.64 (bs, 4H), 0.94-0.82 (m, 4H) | A Method 7.08 |

TABLE 16

| Compound No. | Structure | Name | Dtctd Mass | 1H NMR | HPLC |
|---|---|---|---|---|---|
| 113 | 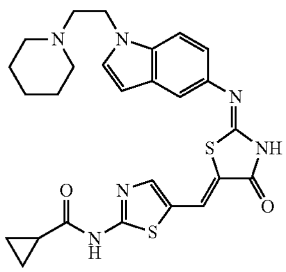 | (5Z)-cyclopropyl-N-{5-[(4-oxo-2-{[1-(2-piperidinoethyl)indol-5-yl]azamethylene}-(1,3-thiazolidin-5-ylidene))methyl](1,3-thiazol-2-yl)}carboxamide | 521.3 | ¹H NMR (300 MHz, DMSO-d6) δ = 7.92 (s, 1H), 7.80 (s, 1H), 7.50 (m, 2H), 7.43 (m, 2H), 6.44 (m, 1H), 4.25 (m, 2H), 2.57 (m, 2H), 2.48 (m, 4H), 1.94 (m, 1H), 1.45 (bs, 4H), 1.35 (bs, 2H), 0.94-0.82 (m, 4H) | A Method 7.17 |
| 114 | 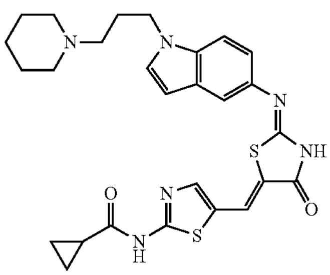 | (5Z)-cyclopropyl-N-{5-[(4-oxo-2-{[1-(3-piperidinopropyl)indol-5-yl]azamethylene}-(1,3-thiazolidin-5-ylidene))methyl](1,3-thiazol-2-yl)}carboxamide | 535.5 | ¹H NMR (300 MHz, DMSO-d6) δ = 7.91 (s, 1H), 7.78 (s, 1H), 7.50 (m, 2H), 7.43 (m, 2H), 6.44 (m, 1H), 4.18 (m, 2H), 2.48 (m, 4H), 2.24 (m, 2H), 1.90 (m, 3H), 1.49 (bs, 4H), 1.35 (bs, 2H), 0.94-0.82 (m, 4H) | A Method 7.26 |
| 115 | 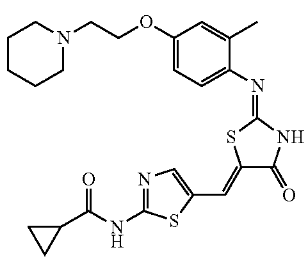 | (2Z,5Z)-cyclopropyl-N-{5-[(2-{[2-methyl-4-(2-piperidinoethoxy)phenyl]azamethylene}-4-oxo(1,3-thiazolidin-5-ylidene))methyl](1,3-thiazol-2-yl)}carboxamide | 512.5 | ¹H NMR (300 MHz, DMSO-d6) δ = 7.97 (s, 1H), 7.85 (s, 1H), 6.96-6.88 (m, 3H), 4.36-4.33 (m, 2H), 3.56-3.48 (m, 4H), 3.06-2.96 (m, 2H), 2.12 (s, 3H), 1.98-1.88 (m, 1H), 1.80 (bs, 2H), 1.75-1.62 (m, 2H), 1.45-1.37 (m, 2H), 0.96-0.82 (m, 4H) | B Method 10.734 |
| 116 | 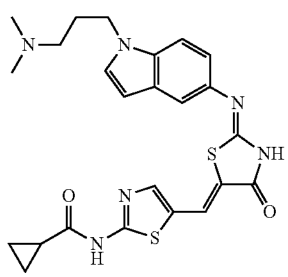 | (5Z)-N-(5-{[2-({1-[3-(dimethylamino)propyl]indol-5-yl}azamethylene)-4-oxo(1,3-thiazolidin-5-ylidene)]methyl}(1,3-thiazol-2-yl))cyclopropylcarboxamide | 495.4 | ¹H NMR (300 MHz, DMSO-d6) δ = 8.14 (s, 1H), 7.92 (s, 1H), 7.86 (s, 1H), 7.56 (m, 2H), 7.43 (m, 2H), 6.48 (m, 1H), 4.25 (m, 2H), 3.12 (m, 2H), 2.75 (bs, 6H), 1.15 (m, 2H), 1.93 (bs, 1H), 0.91 (m, 4H) | A Method 6.85 |
| 117 | 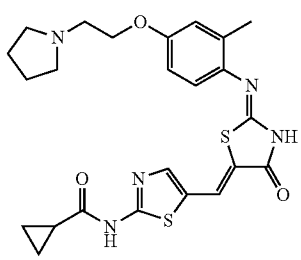 | (2Z,5Z)-cyclopropyl-N-{5-[(2-{[2-methyl-4-(2-(1-pirroridinyl)ethoxy)phenyl]azamethylene}-4-oxo(1,3-thiazolidin-5-ylidene))methyl](1,3-thiazol-2-yl)}carboxamide | 498.6 | ¹H NMR (300 MHz, DMSO-d6) δ = 7.91 (s, 1H), 7.82 (s, 1H), 6.92-6.88 (m, 3H), 4.29 (bs, 2H), 2.58-3.49 (m, 4H), 3.14 (bs, 2H), 2.11 (s, 3H), 2.02-1.86 (m, 4H), 1.59 (bs, 1H), 0.90-0.84 (m, 4H) | B Method 10.481 |

TABLE 16-continued

| Compound No. | Structure | Name | Dtctd Mass | 1H NMR | HPLC |
|---|---|---|---|---|---|
| 118 | 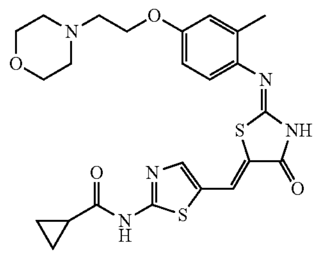 | (2Z,5Z)-cyclopropyl-N-{5-[(2-{[2-methyl-4-(2-morpholinoethoxy)phenyl]azamethylene}-4-oxo(1,3-thiazolidin-5-ylidene))methyl](1,3-thiazol-2-yl)}carboxamide | 514.5 | ¹H NMR (300 MHz, DMSO-d6) δ = 7.95 (s,1H), 7.84 (s, 1H), 6.95-6.89 (m, 3H), 4.36 (bs, 2H), 3.95 (bs, 2H), 3.71 (bs, 2H), 3.57 (bs, 4H), 3.12 (bs, 2H), 2.12 (s, 3H), 1.96-1.91 (m, 1H), 0.92-0.85 (m, 4H) | B Method 10.333 |
| 119 | 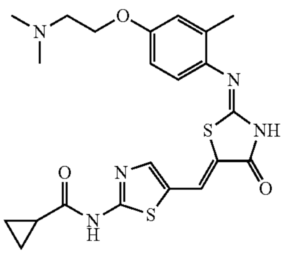 | (2Z,5Z)-N-(5{[2-({4-[2-(dimethylamino)ethoxy]-2-methylphenyl}azamethylene)-4-oxo(1,3-thiazolidin-5-ylidene)]methyl}(1,3-thiazol-2-yl))cyclopropylcarboxamide | 472.5 | ¹H NMR (300 MHz, DMSO-d6) δ = 7.94 (s, 1H), 7.82 (s, 1H), 6.93-6.80 (m, 3H), 4.09 (t, J = 5.9 Hz, 2H), 2.75 (t, J = 5.7 Hz, 2H), 2.31 (bs, 6H), 2.11 (s, 3H), 1.94-1.90 (m, 1H), 0.92-0.88 (m, 4H) | B Method 10.251 |
| 120 | 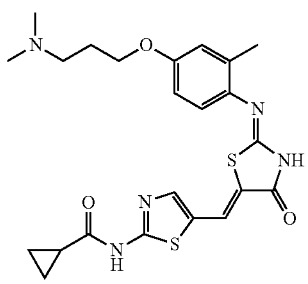 | (2Z,5Z)-N-(5{[2-({4-[3-(dimethylamino)propoxy]-2-methylphenyl}azamethylene)-4-oxo(1,3-thiazolidin-5-ylidene)]methyl}(1,3-thiazol-2-yl))cyclopropylcarboxamide | 486.2 | ¹H NMR (300 MHz, DMSO-d6) δ = 7.92 (s, 1H), 7.82 (s, 1H), 6.91 (d, J = 8.7 Hz, 1H), 6.86 (s, 1H), 6.80 (dd, J = 2.4 Hz, J = 8.4 Hz, 1H), 4.05 (t, J = 5.7 Hz, 2H), 3.25-3.21 (m, 2H), 2.80 (bs, 6H), 2.10 (bs, 5H), 1.93 (bs, 1H), 0.93-0.86 (m, 4H) | B Method 10.511 |

TABLE 17

| Compound No. | Structure | Name | Dtctd Mass | 1H NMR | HPLC |
|---|---|---|---|---|---|
| 121 | 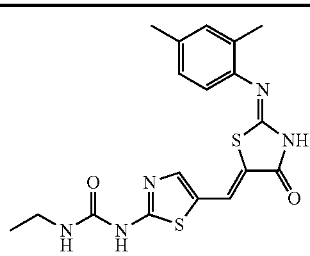 | (2Z,5Z)-N-[5-({2-[(2,4-dimethylphenyl)azamethylene]-4-oxo(1,3-thiazolidin-5-ylidene)}methyl)(1,3-thiazol-2-yl)](ethylamino)carboxamide | 402.4 | ¹H NMR (300 MHz, DMSO-d6) δ = 7.81 (s, 1H), 7.77 (s, 1H), 7.03 (d, J = 7.8 Hz, 1H), 6.83 (d, J = 7.8 Hz, 1H), 6.57 (m, 1H), 3.1 (q, J = 6.9 Hz, 2H), 2.28 (s, 3H), 2.08 (s, 3H), 1.01 (t, J = 6.9 Hz, 2H) | B Method 11.76 |
| 122 | 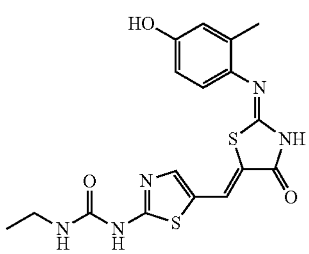 | (2Z,5Z)-(ethylamino)-N-[5-{(2-[(4-hydroxy-2-methylphenyl)azamethylene]-4-oxo(1,3-thiazolidin-5-ylidene)}methyl)(1,3-thiazol-2-yl)]carboxamide | 404.2 | ¹H NMR (300 MHz, DMSO-d6) δ = 8.30 (s, 1H), 8.06 (s, 1H), 6.90-6.84 (m, 3H), 3.0 (m, 2H), 2.27 (s, 3H), 2.07 (s, 3H), 1.01 (t, J = 6.9 Hz, 2H) | B Method 9.31 |

TABLE 17-continued

| Compound No. | Structure | Name | Dtctd Mass | 1H NMR | HPLC |
|---|---|---|---|---|---|
| 123 | 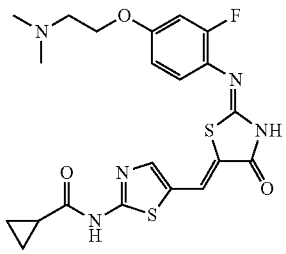 | (2Z,5Z)-N-(5{[2-({4-[2-(dimethylamino) ethoxy]-2-fluorophenyl)azamethylene)-4-oxo(1,3-thiazolidin-5-ylidene)]methyl}(1,3-thiazol-2-yl))cyclopropyl-carboxamide | 476.4 | ¹H NMR (300 MHz, DMSO-d6) δ = 7.99 (s, 1H), 7.89 (s, 1H), 7.14-7.00 (m, 2H), 6.89 ((d, J = 6.3 Hz, 1H), 4.37-4.34 (m, 2H), 3.51 (bs, 2H), 2.87 (bs, 6H), 1.98-1.93 (m, 1H), 0.93-0.83 (m, 4H) | B Method 10.316 |
| 124 | 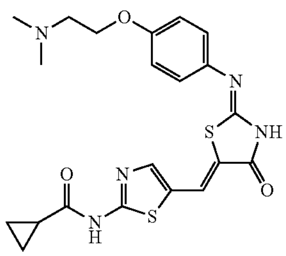 | (2Z,5Z)-N-(5-{[2-({4-[2-(dimethylamino)ethoxy]phenyl}azamethylene)-4-oxo(1,3-thiazolidin-5-ylidene)]methyl}(1,3-thiazol-2-yl))cyclopropyl-carboxamide | 458.4 | ¹H NMR (300 MHz, DMSO-d6) δ = 7.92 (s, 1H), 7.82 (s, 1H), 7.68 (d, J = 8.7 Hz, 1H), 7.03 (bs, 3H), 4.34-4.30 (m, 2H), 3.50 (bs, 2H), 2.84 (bs, 6H), 1.93 (bs, 1H), 0.92-0.80 (m, 4H) | B Method 10.221 |
| 125 | 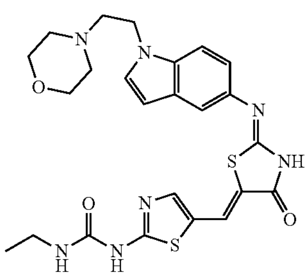 | (5Z)-(ethylamino)-N-{5-[(2-{[1-(2-morpholinoethyl)indol-5-yl]azamethylene}-4-oxo(1,3-thiazolidin-5-ylidene))methyl](1,3-thiazol-2-yl)}carboxamide | 526.4 | No data | A Method 6.78 |
| 126 | 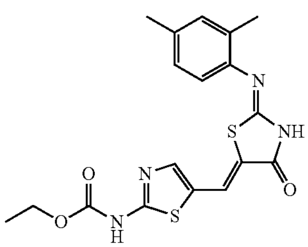 | (5Z)-N-[5-({2-[(2,4-dimethylphenyl)azamethylene]-4-oxo(1,3-thiazolidin-5-ylidene)}methyl)(1,3-thiazol-2-yl)]ethoxycarboxamide | 403.4 | ¹H NMR (300 MHz, DMSO-d6) δ = 7.85 (s, 1H), 7.80 (s, 1H), 7.07 (s, 1H), 7.02 (d, J = 8.1 Hz, 1H), 6.82 (d, J = 7.8 Hz, 1H), 4.21-4.10 (m, 2H), 2.27 (s, 3H), 2.08 (s, 3H), 1.20 (t, J = 7.1 Hz, 3H) | B Method 12.889 |
| 127 | 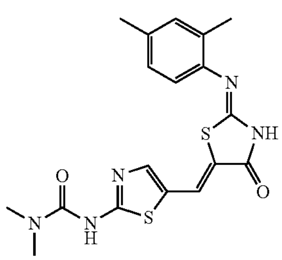 | (2Z,5Z)-(dimethylamino)-N-[5-({2-[(2,4-dimethylphenyl)azamethylene]-4-oxo(1,3-thiazolidin-5-ylidene)}methyl)(1,3-thiazol-2-yl)]carboxamide | 402.4 | ¹H NMR (300 MHz, DMSO-d6) δ = 7.84 (s, 1H), 7.77 (s, 1H), 7.07 (s, 1H), 7.03 (d, J = 7.8 Hz, 1H), 6.82 (d, J = 7.5 Hz, 1H), 2.91 (bs, 6H), 2.27 (s, 3H), 2.09 (s, 3H) | B Method 12.325 |
| 128 | 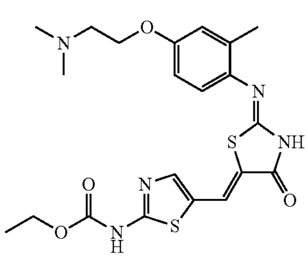 | (2Z,5Z)-N-(5-{[2-({4-[2-(dimethylamino)ethoxy]-2-methylphenyl}azamethylene)-4-oxo(1,3-thiazolidin-5-ylidene)]methyl}(1,3-thiazol-2-yl))ethoxy carboxamide | 476.4 | ¹H NMR (300 MHz, DMSO-d6) δ = 7.88 (s, 1H), 7.82 (s, 1H), 6.94-6.83 (m, 3H), 4.33 (bs, 2H), 4.18-4.12 (m, 2H), 3.52 (bs, 2H), 2.88 (bs, 6H), 2.13 (s, 3H), 1.21 (t, J = 6.9 Hz, 3H) | B Method 10.284 |

TABLE 18

| Compound No. | Structure | Name | Dtctd Mass | 1H NMR | HPLC |
|---|---|---|---|---|---|
| 129 | 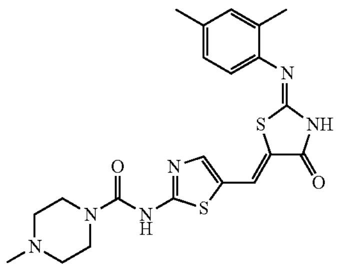 | (2Z,5Z)-N-[5-({2-[(2,4-dimethylphenyl)azamethylene]-4-oxo(1,3-thiazolidin-5-ylidene)}methyl)(1,3-thiazol-2-yl)](1-(4-methyl)piperazinyl)carboxamide | 457.4 | ¹H NMR (300 MHz, DMSO-d6) δ = 7.85 (s, 1H), 7.76 (s, 1H), 7.06 (s, 1H), 7.01 (d, J = 7.8 Hz, 1H), 6.81 (d, J = 7.8 Hz, 1H), 4.30 (bs, 2H), 3.41 (d, J = 10.5 Hz, 2H), 3.15 (t, J = 12.5 Hz, 2H), 2.99 (bs, 2H), 2.77 (s, 3H), 2.26 (s, 3H), 2.08 (s, 3H) | B Method 10.415 |
| 130 | 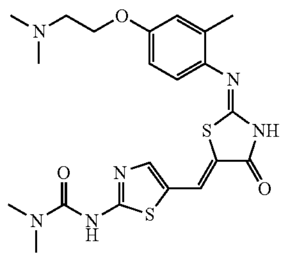 | (2Z,5Z)-(dimethylamino)-N-(5-{[2-({4-[2-(dimethylamino)ethoxy]-2-methylphenyl}azamethylene)-4-oxo(1,3-thiazolidin-5-ylidene)]methyl}(1,3-thiazol-2-yl)carboxamide | 475.2 | ¹H NMR (300 MHz, DMSO-d6) δ = 7.86 (s, 1H), 7.79 (s, 1H), 6.95-6.86 (m, 3H), 4.33 (bs, 2H), 3.51 (bs, 2H), 2.91 (bs, 6H), 2.88 (bs, 6H), 2.12 (s, 3H) | B Method 9.929 |
| 131 | 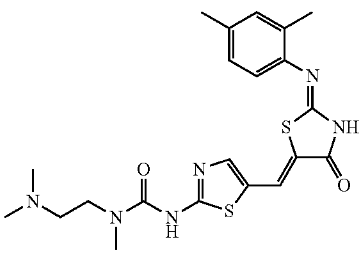 | (2Z,5Z)-{2-(dimethylamino)ethyl]methylamino}-N-[5-({2-[(2,4-dimethylphenyl)azamethylene]-4-oxo(1,3-thiazolidin-5-ylidene)}methyl)(1,3-thiazol-2-yl)]carboxamide | 459.2 | ¹H NMR (300 MHz, DMSO-d6) δ = 9.23 (bs, 1H), 7.87 (s, 1H), 7.78 (s, 1H), 7.07 (s, 1H), 7.02 (d, J = 8.1 Hz, 1H), 6.82 (d, J = 8.1 Hz, 1H), 3.65 (t, J = 5.9 Hz, 2H), 3.23 (d, J = 5.1 Hz, 2H), 2.98 (s, 3H), 2.80 (bs, 6H), 2.27 (s, 3H), 2.08 (s, 3H) | B Method 10.597 |
| 132 | 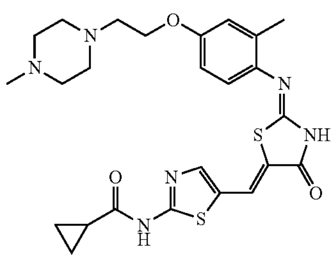 | (2Z,5Z)-cyclopropyl-N-(5-{[2-({2-methyl-4-[2-(1-(4-methyl)piperazinyl)ethoxy]phenyl}azamethylene)-4-oxo(1,3-thiazolidin-5-ylidene)]methyl}(1,3-thiazol-2-yl)carboxamide | 527.5 | ¹H NMR (300 MHz, DMSO-d6) δ = 7.92 (s, 1H), 7.79 (s, 1H), 6.91-6.75 (m, 3H), 4.05 (t, J = 5.4 Hz, 2H), 2.67 (t, J = 6.0 Hz, 2H), 2.48 (bs, 4H), 2.34 (bs, 4H), 2.15 (s, 3H), 2.09 (s, 3H), 1.83 (m, 1H), 0.90 (m, 4H) | B Method 9.68 |
| 133 | 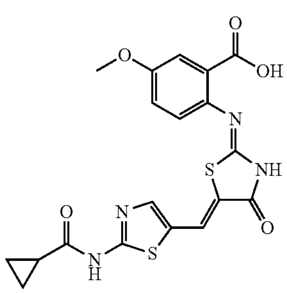 | (2Z,5Z)-2-[(5-{[2-(cyclopropyl-carbonylamino)(1,3-thiazol-5-yl)]methylene}-4-oxo(1,3-thiazolidin-2-ylidene))azamethyl]-5-methoxybenzoic acid | 445.3 | ¹H NMR (300 MHz, DMSO-d6) δ = 12.80 (s, 1H), 12.60 (bs, 1H), 7.96 (s, 1H), 7.84 (s, 1H), 7.36 (s, 1H), 7.17 (dd, J = 2.7 Hz, J = 9.0 Hz, 1H), 6.99 (d, J = 7.5 Hz, 1H), 3.80 (s, 3H), 1.92 (bs, 1H), 0.89 (bs, 4H) | B Method 11.600 |

TABLE 18-continued

| Compound No. | Structure | Name | Dtctd Mass | 1H NMR | HPLC |
|---|---|---|---|---|---|
| 134 | 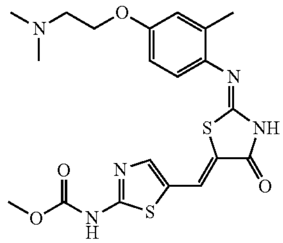 | (2Z,5Z)-N-(5-{[2-({4-[2-(dimethylamino)ethoxy]-2-methylphenyl}azamethylene)-4-oxo(1,3-thiazolidin-5-ylidene)]methyl}(1,3-thiazol-2-yl))methoxycarboxamide | 462.3 | ¹H NMR (300 MHz, CD₃OD) δ = 8.50 (bs, 1H), 7.79 (s, 1H), 7.68 (s, 1H), 7.05-6.94 (m, 3H), 4.33-4.32 (m, 2H), 3.81 (s, 3H), 2.42 (bs, 2H), 2.85 (bs, 6H), 2.22 (s, 3H) | B Method 9.862 |
| 135 | 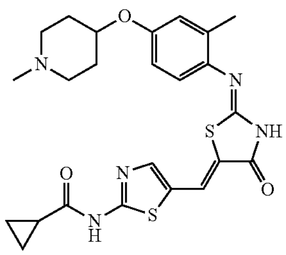 | (2Z,5Z)-cyclopropyl-N-{5-[(2-{[2-methyl-4-(1-methyl(4-piperidyloxy))phenyl]azamethylene}-4-oxo(1,3-thiazolidin-5-ylidene))methyl](1,3-thiazol-2-yl)}carboxamide | 498.5 | ¹H NMR (300 MHz, DMSO-d6) δ = 7.92 (s,1H), 7.79 (s, 1H), 6.85 (bs, 2H), 6.80 (dd, J = 2.4 Hz, J = 8.4 Hz, 1H), 4.38-4.32 (m, 1H), 2.65-2.63 (m, 2H), 2.40 (bs, 5H), 2.10 (s, 3H), 1.92 (bs, 3H), 1.66-1.62 (m, 2H), 0.89 (bs, 4H) | B Method 10.387 |
| 136 | 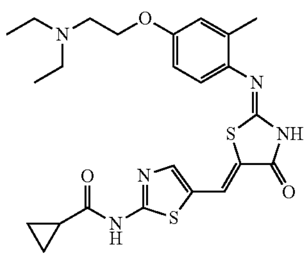 | (2Z,5Z)-N-(5-{[2-({4-[2-(diethylamino)ethoxy]-2-methylphenyl}azamethylene)-4-oxo(1,3-thiazolidin-5-ylidene)]methyl}(1,3-thiazol-2-yl))cyclopropylcarboxamide | 500.0 | ¹H NMR (300 MHz, DMSO-d6) δ = 7.92 (s, 1H), 7.79 (s, 1H), 6.91-6.87 (m, 2H), 6.79 (dd, J =3.0 Hz, J =9.0 Hz, 1H), 4.03 (t, J = 6.0 Hz, 2H), 2.78 (t, J = 6.2 Hz, 2H), 2.62-2.49 (m, 4H), 2.10 (s, 3H), 1.94-1.89 (m, 1H), 1.01-0.95 (m, 6H), 0.89 (bs, 4H) | B Method 10.518 |

TABLE 19

| Compound No. | Structure | Name | Dtctd Mass | 1H NMR | HPLC |
|---|---|---|---|---|---|
| 137 | 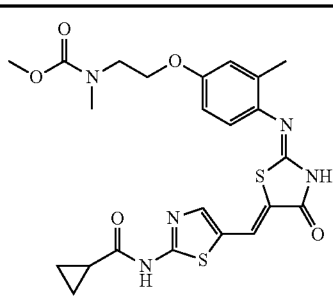 | (2Z,5Z)-N-(2-{4-[(5-{[2-(cyclopropylcarbonylamino)(1,3-thiazol-5-yl)]methylene}-4-oxo(1,3-thiazolidin-2-ylidene))azamethyl]-3-methylphenoxy}ethyl)methoxy-N-methylcarboxamide | 516.4 | ¹H NMR (300 MHz, DMSO-d6) δ = 7.96 (s, 1H), 7.82 (s, 1H), 6.89-6.78 (m, 3H), 4.08 (t, J = 5.4 Hz, 2H), 3.58 (s, 3H), 3.30 (bs, 2H), 2.92 (bs, 3H), 2.14 (s, 3H), 1.93 (m, 1H), 0.89 (bs, 4H) | B Method 11.49 |
| 138 | 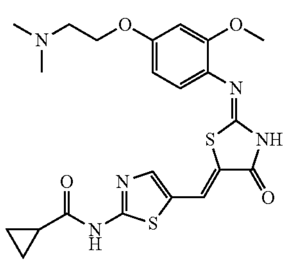 | (2Z,5Z)-N-(5-{[2-{(4-[2-(dimethylamino)ethoxy]-2-methoxyphenyl}azamethylene)-4-oxo(1,3-thiazolidin-5-ylidene]methyl}(1,3-thiazol-2-yl))cyclopropylcarboxamide | 488.4 | ¹H NMR (300 MHz, DMSO-d6) δ = 7.93 (s, 1H), 7.83 (s, 1H), 7.03 (t, J = 9.0 Hz, 2H), 6.81-6.57 (m, 2H), 4.18 (s, 2H), 3.76 (s, 3H), 2.57 (m, 2H), 2.15 (s, 6H), 1.94 (m, 1H), 0.89 (bs, 4H) | A Method 6.02 |

TABLE 19-continued

| Compound No. | Structure | Name | Dtctd Mass | 1H NMR | HPLC |
|---|---|---|---|---|---|
| 139 | 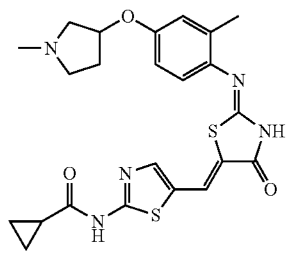 | (2Z,5Z)-cyclopropyl-N-{5-[(2-{[2-methyl-4-(1-methylpyrrolidin-3-yloxy)phenyl]azamethylene}-4-oxo(1,3-thiazolidin-5-ylidene))methyl](1,3-thiazol-2-yl)}carboxamide | 484.5 | $^1$H NMR (300 MHz, DMSO-d6) δ = 7.92 (s, 1H), 7.79 (s, 1H), 6.88 (d, J = 8.4 Hz, 1H), 6.80 (bs, 1H), 6.73 (d, J = 8.7 Hz, 1H), 4.86 (bs, 1H), 2.82-2.77 (m, 2H), 2.71-2.60 (m, 2H), 2.41-2.30 (m, 2H), 2.27 (bs, 3H), 2.10 (s, 3H), 1.94-1.90 (m, 1H), 0.89 (bs, 4H) | B Method 10.121 |
| 140 | 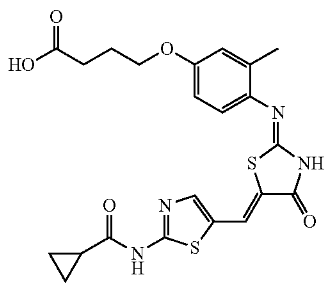 | (2Z,5Z)-4-{4-[(5-{[2-(cyclopropyl-carbonylamino)(1,3-thiazol-5-yl)]methylene}-4-oxo(1,3-thiazolidin-2-ylidene))azamethyl]-3-methylphenoxy}butyric acid | 487.5 | $^1$H NMR (300 MHz, DMSO-d6) δ = 7.93 (s, 1H), 7.80 (s, 1H), 6.91-6.87 (m, 2H), 6.79 (d, J = 8.4 Hz, 1H), 3.98 (t, J = 6.0 Hz, 2H), 2.40 (t, J = 7.1 Hz, 2H), 2.11 (s, 3H), 1.94 (bs, 3H), 0.89 (s, 4H) | B Method 11.200 |
| 141 | 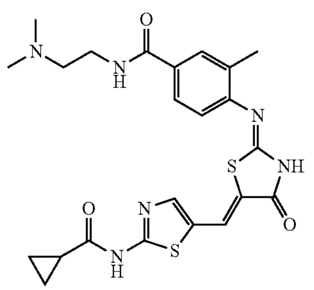 | (2Z,5Z)-N-[2-(dimethylamino)ethyl](4-[(5-{[2-(cyclopropyl-carbonylamino)(1,3-thiazol-5-yl)]methylene]-4-oxo(1,3-thiazolidin-2-ylidene))azamethyl]-3-methylphenyl}carboxamide | 499.6 | $^1$H NMR (300 MHz, DMSO-d6) δ = 8.36 (bs, 1H), 7.91 (s, 1H), 7.77 (s, 1H), 7.71 (s, 1H), 7.65 (d, J = 7.5 Hz, 1H), 6.94 (d, J = 7.2 Hz, 2H), 3.6-3.2 (m, 2H), 2.58 (t, J = 6.3 Hz, 2H), 2.31 (s, 6H), 2.14 (s, 3H), 1.93 (m, 1H), 0.88 (m, 4H) | A Method 7.63 |
| 142 | 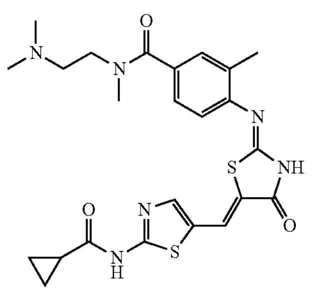 | (2Z,5Z)-N-[2-(dimethylamino)ethyl](4-[5-{[2-(cyclopropyl-carbonylamino)(1,3-thiazol-5-yl)]methylene}-4-oxo(1,3-thiazolidin-2-ylidene))azamethyl]-3-methylphenyl}-N-methylcarboxamide | 513.5 | $^1$H NMR (300 MHz, DMSO-d6) δ = 7.92 (s, 1H), 7.80 (s, 1H), 7.27 (s, 1H), 7.21 (d, J = 8.1 Hz, 1H), 6.73 (d, J = 7.8 Hz, 2H), 3.6-3.2 (m, 2H), 2.94 (s, 3H), 2.58 (m, 2H), 2.48 (s, 6H), 2.12 (s, 3H), 1.93 (m, 1H), 0.88 (m, 4H) | B Method 9.16 |
| 143 | 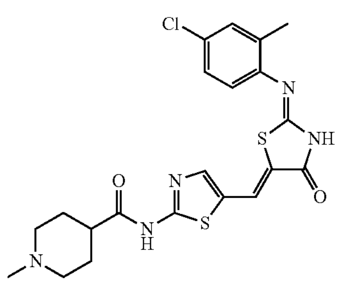 | (2Z,5Z)-N-[5-({2-[(4-chloro-2-methylphenyl)azamethylene]-4-oxo(1,3-thiazolidin-5-ylidene}methyl)(1,3-thiazol-2-yl)](1-methyl(4-piperidinyl))}carboxamide | 476.4 | $^1$H NMR (300 MHz, DMSO-d6) δ = 9.39 (bs, 1H), 7.90 (bs, 1H), 7.32 (bs, 2H), 6.91 (bs, 1H), 2.94 (bs, 3H), 2.77 (bs, 4H), 2.11 (bs, 6H), 1.80 (bs, 2H) | B Method 10.610 |

TABLE 19-continued

| Compound No. | Structure | Name | Dtctd Mass | 1H NMR | HPLC |
|---|---|---|---|---|---|
| 144 | 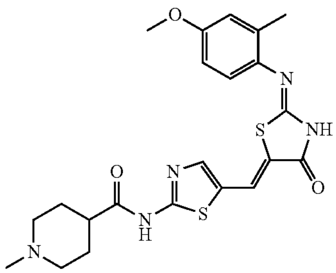 | (2Z,5Z)-N-[5-({2-[(4-methoxy-2-methylphenyl)azamethylene]-4-oxo(1,3-thiazolidin-5-ylidene)}methyl)(1,3-thiazol-2-yl)](1-methyl(4-piperidyl)}carboxamide | 472.4 | $^1$H NMR (300 MHz, DMSO-d6) δ = 7.93 (s, 1H), 7.80 (s, 1H), 6.94-6.87 (m, 2H), 6.81 (dd, J = 2.7 Hz, J = 8.4 Hz, 1H), 3.77 (s, 3H), 2.79 (bs, 2H), 2.42 (bs, 1H), 2.16 (s, 3H), 2.12 (s, 3H), 1.87 (t, J = 10.5 Hz, 2H), 1.72 (bs, 2H), 1.61 (bs, 2H) | B Method 9.987 |

TABLE 20

| Compound No. | Structure | Name | Dtctd Mass | 1H NMR | HPLC |
|---|---|---|---|---|---|
| 145 | 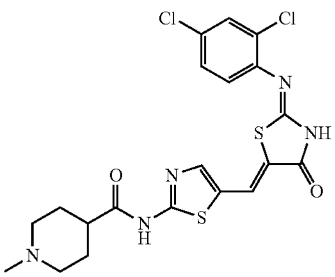 | (2Z,5Z)-N-[5-({2-[(2,4-dochlorophenyl)azamethylene]-4-oxo(1,3-thiazolidin-5-ylidene)}methyl)(1,3-thiazol-2-yl)](1-methyl(4-piperidyl)}carboxamide | 496.4 | $^1$H NMR (300 MHz, DMSO-d6) δ = 8.02 (s,1H), 7.93 (s, 1H), 7.70 (s,1H), 7.47 (d, J = 8.7 Hz, 1H), 7.18 (d, J = 8.4 Hz, 1H), 3.49-3.45 (m, 2H), 2.97-2.93 (m, 2H), 2.76 (bs, 4H), 2.06-2.02 (m, 2H), 1.83-1.75 (m, 2H) | B Method 10.750 |
| 146 | 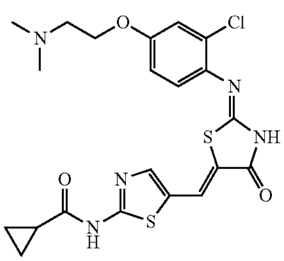 | (2Z,5Z)-N-(5-{[2-({4-[2-(dimethylamino)ethoxy]-2-chlorophenyl}azamethylene)-4-oxo(1,3-thiazolidin-5-ylidene)]methyl}(1,3-thiazol-2-yl))cyclopropylcarboxamide | 492.3 | $^1$H NMR (300 MHz, DMSO-d6) δ = 7.95 (s, 1H), 7.83 (s, 1H), 7.13 (d, J = 7.2 Hz, 1H), 7.02 (bs, 1H), 6.96 (dd, J = 2.7 Hz, J = 8.7 Hz, 1H), 4.12 (t, J = 2.7 Hz, 2H), 2.73 (t, J = 5.6 Hz, 2H), 2.30 (s, 6H), 1.94-1.89 (m, 1H), 0.89 (bs, 4H) | B Method 10.151 |
| 147 | 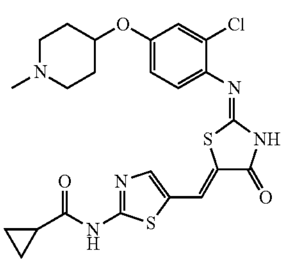 | (2Z,5Z)-N-{5-[(2-{[2-chloro-4-(1-methyl(4-piperidyloxy))phenyl]azamethylene}-4-oxo(1,3-thiazolidin-5-ylidene))methyl](1,3-thiazol-2-yl)}cyclopropylcarboxamide | 518.3 | $^1$H NMR (300 MHz, DMSO-d6) δ = 7.94 (s, 1H), 7.81 (s, 1H), 7.12 (d, J = 2.4 Hz, 1H), 7.01 (bs, 1H), 6.96 (dd, J = 2.1 Hz, H = 8.4 Hz, 1H), 4.43 (bs, 1H), 2.70 (bs, 2H), 2.25 (bs, 5H), 1.93 (bs, 3H), 1.71-1.65 (m, 2H), 0.89 (bs, 4H) | B Method 10.393 |

TABLE 20-continued

| Compound No. | Structure | Name | Dtctd Mass | 1H NMR | HPLC |
|---|---|---|---|---|---|
| 148 | 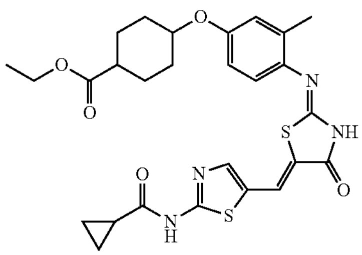 | (2Z,5Z)-ethyl-4-{4-[(5-{[2-(cyclopropyl-carbonylamino)(1,3-thiazol-5-yl)]methylene}-4-oxo(1,3-thiazolidin-2-ylidene))azamethyl]-3-methylphenoxy}cyclohexane-carboxylate | 555.5 | $^1$H NMR (300 MHz, DMSO-d6) δ = 8.05 (s, 1H), 7.81 (s, 1H), 6.86-6.80 (m, 3H), 4.37 (bs, 1H), 4.05 (m,3H), 2.09 (s, 3H), 2.0-1.32 (m, 9H), 1.18 (bs, 3H), 0.94 (m, 4H) | A Method 8.84 |
| 149 | 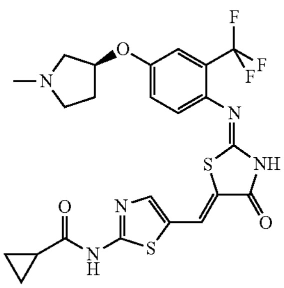 | (2Z,5Z)-N-{5-[(2-{[4-((3S)-1-methylpyrrolidin-3-yloxy)-2-(trifluoromethyl)phenyl]azamethylene}-4-oxo(1,3-thiazolidin-5-ylidene))methyl](1,3-thiazol-2-yl)}cyclopropyl-carboxamide | 538.5 | $^1$H NMR (300 MHz, DMSO-d6) δ = 7.93 (s, 1H), 7.81 (s, 1H), 7.24-7.07 (m, 3H), 4.98 (bs, 1H), 2.91-2.74 (m, 4H), 2.37-2.24 (m, 5H), 1.96-1.78 (m, 3H), 0.87 (m, 4H) | B Method 9.71 |
| 150 | 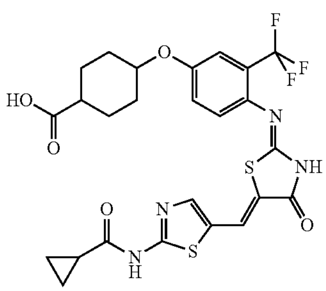 | (2Z,5Z)-4-{4-[(5-{[2-(cyclopropyl-carbonylamino)(1,3-thiazol-5-yl)]methylene}-4-oxo(1,3-thiazolidin-2-ylidene))azamethyl]-3-(trifluoromethyl)phenyloxy}cyclohexane-carboxylic acid | 581.3 | $^1$H NMR (300 MHz, DMSO-d6) δ = 7.85 (s, 1H), 7.68 (s, 1H), 7.24 (d, J = 7.5 Hz, 1H), 7.16 (s, 1H), 7.03 (d, J = 8.1 Hz, 1H), 4.39 (bs, 1H), 2.98 (m, 1H), 2.1-1.35 (m, 9H), 0.94 (m, 4H) | A Method 7.23 |
| 151 | 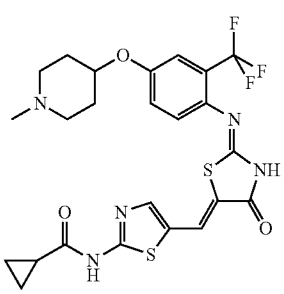 | (2Z,5Z)-cyclopropyl-N-{5-[(2-{[4-(1-methyl(4-piperidyloxy))-2-(trifluoromethyl)phenyl]azamethylene}-4-oxo(1,3-thiazolidin-5-ylidene))methyl](1,3-thiazol-2-yl)}carboxamide | 552.2 | $^1$H NMR (300 MHz, DMSO-d6) δ = 7.93 (s, 1H), 7.81 (s, 1H), 7.28 (d, J = 8.4 Hz, 1H), 7.22 (s, 1H), 7.10 (d, J = 8.7 Hz, 1H), 4.50 (bs, 1H), 2.73-2.7 (m, 2H), 2.49-2.52 (m, 2H), 2.28 (s, 3H), 1.93 (bs, 3H), 1.76-1.65 (m, 2H), 0.90 (bs, 4H) | B Method 10.568 |
| 152 | 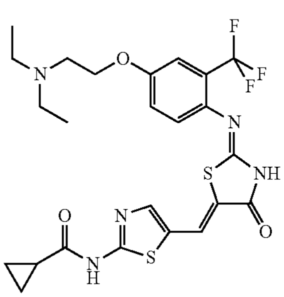 | (2Z,5Z)-N-(5-{[2-({4-[2-(diethylamino)ethoxy]-2-(trifluoromethyl)phenyl}azamethylene)-4-oxo(1,3-thiazolidin-5-ylidene)]methyl}(1,3-thiazol-2-yl))cyclopropyl-carboxamide | 554.1 | $^1$H NMR (300 MHz, DMSO-d6) δ = 9.26 (bs, 1H), 8.00 (s, 1H), 7.90 (s, 1H), 7.30 (bs, 2H), 7.19 (d, J = 9.0 Hz, 1H), 4.41 (bs, 2H), 3.53 (bs, 2H), 3.28-3.21 (m, 4H), 1.94 (bs, 1H), 1.24 (t, J = 7.1 Hz, 6H), 0.84 (bs, 4H) | B Method 10.671 |

TABLE 21

| Compound No. | Structure | Name | Dtctd Mass | 1H NMR | HPLC |
|---|---|---|---|---|---|
| 153 | 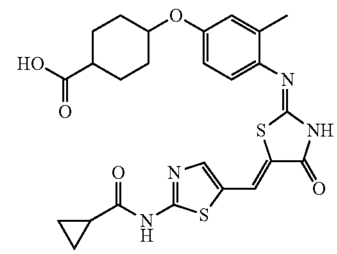 | (2Z,5Z)-4-{4-[(5-{[2-(cyclopropylcarbonylamino)(1,3-thiazol-5-yl)]methylene}-4-oxo(1,3-thiazolidin-2-ylidene)azamethyl]-3-methylphenoxy}cyclohexanecarboxylic acid | 527.3 | 1H NMR (300 MHz, DMSO-d6) δ = 7.93 (s, 1H), 7.81 (s, 1H), 6.89-6.78 (m, 3H), 4.35 (bs, 1H), 2.09 (s, 3H), 2.0-1.32 (m, 9H), 0.94 (m, 4H) | A Method 7.56 |

TABLE 22

| Compound No. | Structure | Name | Dtctd Mass | 1H NMR | HPLC |
|---|---|---|---|---|---|
| 199 | 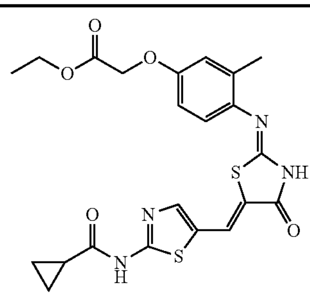 | (2Z,5Z)-ethyl-2-{4-[(5-{[2-cyclopropylcarbonylamino)(1,3-thiazol-5-yl)]methylene}-4-oxo(1,3-thiazolidin-2-ylidene)azamethyl]-3-methylphenoxy}acetate | 487.3 | 1H NMR (300 MHz, DMSO-d6) δ = 12.78 (s, 1H), 7.95 (s, 1H), 7.83 (s, 1H), 6.88 (bs, 2H), 6.80 (bs, 1H), 4.78 (s, 2H), 4.21-4.14 (m, 2H), 2.11 (s, 3H), 1.93 (bs, 1H), 1.23-1.19 (m, 3H), 0.90 (bs, 4H) | B Method 11.421 |
| 200 | 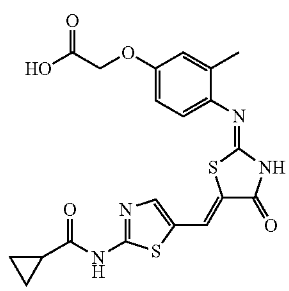 | (2Z,5Z)-2-{4-[(5-{[2-(cyclopropylcarbonylamino)(1,3-thiazol-5-yl)]methylene}-4-oxo(1,3-thiazolidin-2-ylidene)azamethyl]3-methoxyphenoxy}acetic acid | 458.3 | 1H NMR (300 MHz, DMSO-d6) δ = 12.32 (bs, 1H), 7.96 (s, 1H), 7.84 (s, 1H), 6.88 (bs, 2H), 6.80 (bs, 1H), 4.79 (s, 2H), 2.12 (s, 3H), 1.93 (bs, 1H), 0.89 (bs, 4H) | A Method 7.24 |
| 201 | 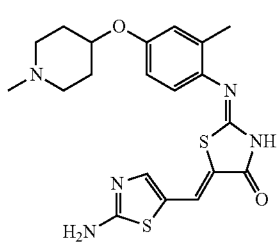 | (2Z,5Z)-5-[(2-amino(1,3-thiazol-5-yl))methylene]-2-}2-methyl-4-(1-methyl(4-piperidyloxy))phenyl]azamethylene}-1,3-thiazolidin-4-one | 430.2 | 1H NMR (300 MHz, DMSO-d6) δ = 7.74 (bs, 2H), 7.64 (s, 1H), 7.51 (1H), 6.87 (bs, 2H), 6.80 (bs, 1H), 4.32 (bs, 1H), 2.80 (bs, 2H), 2.18 (bs, 5H), 2.09 (s, 3H), 1.91 (bs, 2H), 1.64 (bs, 2H) | B Method 8.721 |
| 202 | 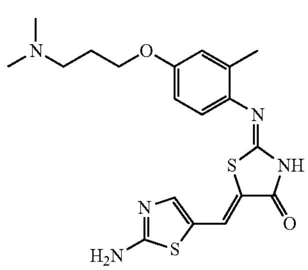 | (2Z,5Z)-5-[(2-amino(1,3-thiazol-5-yl))methylene]-2-({4-[3-(dimethylamino)propoxy]-2-methylphenyl}azamethylene-1,3-thiazolidin-4-one | 418.2 | 1H NMR (300 MHz, DMSO-d6) δ = 7.73 (bs, 2H), 7.64 (s, 1H), 7.51 (s, 1H), 6.90-6.85 (m, 2H), 6.76 (dd, J = 2.7 Hz, J = 8.7 Hz, 1H), 3.97 (t, J = 6.5 Hz, 2H), 2.37 (t, J = 7.1 Hz, 2H), 2.16 (s, 6H), 2.10 (s, 3H), 1.84 (t, J = 6.9 Hz, 2H) | B Method 8.713 |

TABLE 22-continued

| Compound No. | Structure | Name | Dtctd Mass | 1H NMR | HPLC |
|---|---|---|---|---|---|
| 203 | 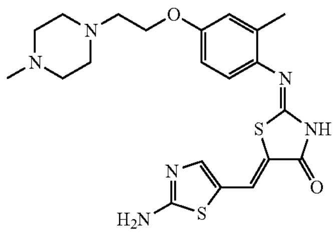 | (2Z,5Z)-5-[(2-amino(1,3-thiazol-5-yl))methylene]-2-({2-methyl-4-[2-(4-methylpiperazinyl)ethoxy]phenyl}azamethylene)-1,3-thiazolidin-4-one | 459.3 | ¹H NMR (300 MHz, DMSO-d6) δ = 7.69 (s, 1H), 7.66 (s, 1H), 6.94 (bs, 2H), 6.88 (bs, 1H), 4.34 (bs, 2H), 3.65 (bs, 10H), 2.90 (s, 3H), 2.12 (s, 3H) | B Method 8.136 |

TABLE 23

| Compound No. | Structure | Name | Dtctd Mass | 1H NMR | HPLC |
|---|---|---|---|---|---|
| 204 | 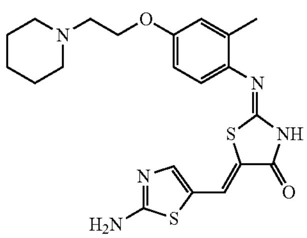 | (2Z,5Z)-5-[2-amino(1,3-thiazol-5-yl))methylene]-2-{[2-chloro-4-(2-piperidylethoxy)phenyl]azamethylene}-1,3-thiazolidin-4-one | 465.1 | ¹H NMR (300 MHz, DMSO-d6) δ = 7.95 (s, 1H), 7.73 (s, 1H), 7.01-6.89 (m, 3H), 4.36 (m, 2H), 3.56-3.49 (m, 4H), 3.06-2.96 (m, 2H), 1.98-1.88 (m, 1H), 1.80 (bs, 2H), 1.75-1.62 (m, 2H), 1.45-1.37 (m, 2H) | B Method 8.724 |
| 205 | 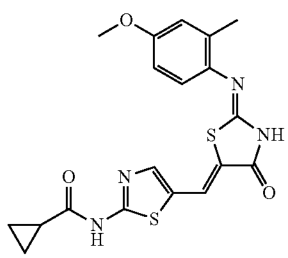 | (2Z,5Z)-cyclopropyl-N-[5-({2-[(4-methoxy-2-methyl-phenyl)azamethylene]-4-oxo(1,3-thiazolidin-5-ylidene)}methyl)(1,3-thiazol-2-yl)]carboxamide | 415.6 | ¹H NMR (300 MHz, DMSO-d6) δ = 7.92 (s, 1H), 7.81 (s, 1H), 6.92-6.80 (m, 3H), 4.09 (s, 3H), 2.11 (s, 3H), 1.94-1.90 (m, 1H), 0.92-0.88 (m, 4H) | A Method 8.23 |
| 206 | 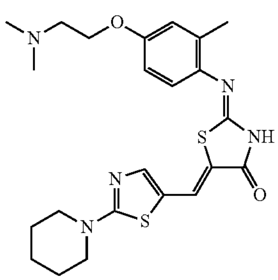 | (2Z,5Z)-2-({4-[2-(dimethylamino)ethoxy]-2-methylphenyl}azamedthylene)-5-[(2-piperidyl(1,3-thiazol-5-yl))methylene]-1,3-thiazolidin-4-one | 472.3 | ¹H NMR (300 MHz, CD3OD) δ = 8.48 (s, 1H), 7.71 (s, 1H), 7.50 (s, 1H), 7.01 (d, J = 8.4 Hz, 1H), 6.88 (m, 2H), 4.30 (t, J = 5.12 Hz, 2H), 3.60 (bs, 2H), 3.58 (bs, 2H), 3.44 (bs, 2H), 2.87 (s, 6H), 2.20 (bs, 3H), 1.58-1.75 (bs, 6H) | A Method |
| 207 | 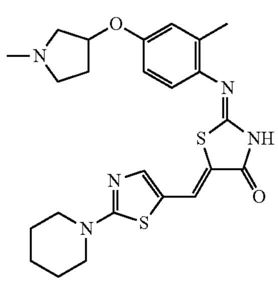 | (2Z,5Z)-2-{[2-methyl-4-(1-methylpyrrolidin-3-yloxy)phenyl]azamethylene}-5-[(2-piperidyl(1,3-thiazol-5-yl))methylene]-1,3-thiazolidin-4-one | 484.3 | ¹H NMR (300 MHz, CD3OD) δ = 8.48 (s, 1H), 7.71 (s, 1H), 7.51 (s, 1H), 7.00 (d, J = 8.7 Hz, 1H), 6.89 (d, J = 2.2 Hz, 1H), 6.82 (m, 1H), 5.13 (s, 1H), 3.65-3.20 (m, 8H), 2.87 (s, 3H), 2.52 (m, 1H), 2.2-2.38 (bs, 5H), 1.66 (bs, 6H) | A Method 6.017 |

TABLE 23-continued

| Compound No. | Structure | Name | Dtctd Mass | 1H NMR | HPLC |
|---|---|---|---|---|---|
| 208 | 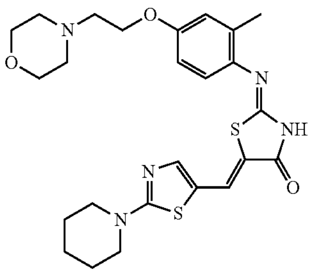 | (2Z,5Z)-2-{[2-methyl-4-(2-morpholin-4-ylethoxy)phenyl]azamethylene}-5-[(2-piperidyl(1,3-thiazol-5-yl))methylene]-1,3-thiazolidin-4-one | 514.3 | $^1$H NMR (300 MHz, CD3OD) δ = 8.26 (s, 1H), 7.70 (s, 1H), 7.50 (s, 1H), 6.97 (d, J = 8.4 Hz, 1H), 6.89 (d, J = 1.8, 1H), 6.82 (d, J = 8.43, 1H), 4.25 (bs, 2H), 3.84 (bs, 4H), 3.59 (bs, 1H), 3.47 (bs, 3H), 3.20 (s, 2H), 3.02 (bs, 4H), 2.26 (s, 3H), 1.69 (bs, 6H) | A Method 6.330 |
| 209 | 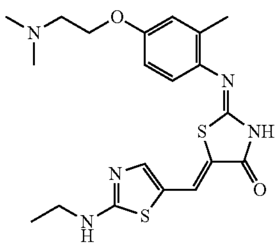 | (2Z,5Z)-2-({4-[2-(dimethylamino)ethoxy]-2-methylphenyl}azamethylene)-5-{[2-(ethylamino)(1,3-thiazol-5-yl)methylene]-1,3-thiazolidin-4-one | 432.2 | $^1$H NMR (300 MHz, CD3OD) δ = 8.29 (s, 1H), 7.66 (s, 1H), 7.57 (s, 1H), 6.95-6.75 (m, 3H), 4.06 (s, 2H), 2.73 (s, 2H), 2.47 (bs, 2H), 2.38 (s, 6H), 2.09 (bs, 3H), 1.10 (t, J = 6.9, 3H) | A Method 5.692 |

TABLE 24

| Compound No. | Structure | Name | Dtctd Mass | 1H NMR | HPLC |
|---|---|---|---|---|---|
| 210 | 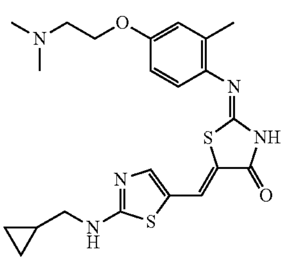 | (2Z,5Z)-2-({4-[2-(dimethylamino)ethoxy]-2-methylphenyl}azamethylene)-5-{[2-(cyclopropylmethyl)amino](1,3-thiazol-5-yl)}methylene)-1,3-thiazolidin-4-one | 458.3 | $^1$H NMR (300 MHz, CD3OD) δ = 8.40 (s, 1H), 7.66 (s, 1H), 7.56 (s, 1H), 6.95-6.75 (m, 3H), 4.06 (s, 2H), 3.10 (t, J = 5.5, 2H), 2.81 (bs, 2H), 2.32 (s, 6H), 2.05 (bs, 3H), 0.99 (m, 1H), 0.41 (d, J = 8.0, 2H), 0.18 (d, J = 4.4, 2H) | A Method 5.910 |
| 211 | 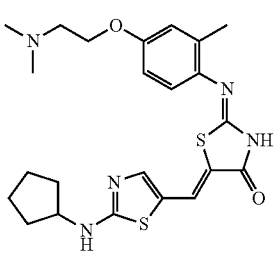 | (2Z,5Z)-2-({4-[2-(dimethylamino)ethoxy]-2-methylphenyl}azamethylene)-5-{[2-(cyclopentylamino)(1,3-thiazol-5-yl)]methylene}-1,3-thiazolidin-4-one | 472.3 | $^1$H NMR (300 MHz, DMSO-d6) δ = 8.34 (d, J =6.2, 1H), 7.65 (s, 1H), 7.57 (s, 1H), 6.95-6.74 (m, 3H), 4.01 (t, J = 6.22, 2H), 3.94 (m, 1H), 2.67 (bs, 2H), 2.25 (s, 6H), 2.09 (s, 3H), 1.84 (m, 2H), 1.66-1.38 (m, 6H) | A Method 5.943 |
| 212 | 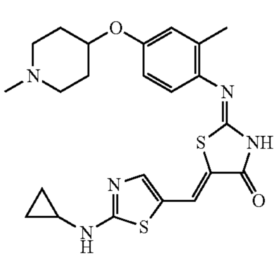 | (2Z,5Z)-5-{[2-(cyclopropylamino)(1,3-thiazol-5-yl)]methylene}-2-{[2-methyl-4-(1-methyl(4-piperidyloxy))phenyl]azamethylene}-1,3-thiazolidin-4-one | 470.8 | 1H NMR (300 MHz, CDCl3) δ = 7.74 (s, 1H), 7.42 (s, 1H), 7.09-6.64 (m, 3H), 4.87 (s, 1H), 4.32 (s, 1H), 3.84 (s, 1H), 2.78 (bs, 2H), 2.50 (bs, 3H), 2.21 (s, 2H), 2.03 (s, 3H), 1.89 (bm, 2H), 1.50 (bs, 2H), 1.25 (s, 3), 0.88-0.82 (m, 4H) | A Method 5.845 |

In Tables 26 to 29, $R_{1a}$ and $R_3$ represent, respectively, $R_{1a}$ and $R_3$ described in the following formula.

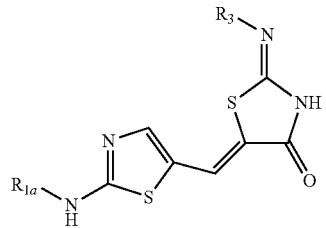

HPLC of the compounds shown in Tables 26 to 29 below was conducted under the following conditions. Cadenza CD-C18, 3 mm, 2×50 mm (Intact) was used as an HPLC column,

TABLE 25

| Mobile phase |
|---|
| A: 10 mM Formic acid aqueous solution<br>B: 10 mM Formic acid MeOH solution |

| Gradient | | |
|---|---|---|
| Time (min) | Flow rate (ml/min) | B % |
| 0-0.5 | 5 | 5 |
| 0.5-2.5 | 5 | 5-95 |
| 2.5-4 | 5 | 95 |

Furthermore, $^1$H-NMR and MS of the compounds shown in Tables 26-29 were conducted under the following conditions.
$^1$H-NMR (400 MHz, DMSO-d6): δ (ppm) as a numerical value.
MS (EMI): [M+H$^+$] as a numerical value.

TABLE 26

| Compound No. | $R_{1a}$ | $R_3$ | Name | 1H-NMR | Dtctd Mass | HPLC |
|---|---|---|---|---|---|---|
| 154 | | | (5Z)-N-(5-{[2-(indol-5-ylazamethylene)-4-oxo-1,3-thiazolidin-5-ylidene]methyl}-1,3-thiazol-2-yl)acetamide | 2.1-2.2 (m, 3H), 6.48 (s, 1H), 6.9 (br, 0.5H), 7.3-7.5 (m, 3H), 7.8-8.1 (m, 2.5H), 11.2 (br, 1H), 12.5 (br, 1H) | 383.7 | 3.1 min |
| 155 | | | (2Z,5Z)-N-(5-{[2-(azapentylidene)-4-oxo-1,3-thiazolidin-5-ylidene]methyl}-1,3-thiazol-2-yl)acetamide | 0.90 (t, 3H, J = 7.2 Hz), 1.3-1.4 (m, 2H), 1.5-1.6 (m, 2H), 3.5-3.6 (m, 2H), 7.78 (s, 1H), 7.94 (s, 1H), 9.5 (br, 1H), 12.5 (br, 1H) | 324.7 | 3.2 min |
| 156 | | | (2Z,5Z)-N-[5-({2-[2-(2-chlorophenyl)-1-azaethylidene]-4-oxo-1,3-thiazolidin-5-ylidene}methyl)-1,3-thiazol-2-yl]acetamide | 2.18 (s, 3H), 4.79 (d, 2H, J = 4.4 Hz), 7.3-7.6 (m, 4H), 7.82 (s, 1H), 7.96 (s, 1H), 10.0 (br, 1H), 12.5 (br, 1H) | 392.7 | 3.3 min |
| 157 | | | (5Z)-N-(5-{[2-(indanylazamethylene)-4-oxo-1,3-thiazolidin-5-ylidene]methyl}-1,3-thiazol-2-yl)acetamide | 1.9-2.0 (m, 1H), 2.1-2.2 (m, 4H), 2.5-3.1 (m, 3H), 7.2-7.4 (m, 4H), 7.83 (s, 1H), 7.96 (s, 1H), 9.90 (d, 1H, J = 7.6 Hz), 12.5 (s, 1H) | 384.8 | 3.3 min |
| 158 | | | (5Z)-N-(5-{[2-(indol-6-ylazamethylene)-4-oxo-1,3-thiazolidin-5-ylidene]methyl}-1,3-thiazol-2-yl)acetamide | 2.1-2.2 (m, 3H), 6.3-6.4 (m, 1H), 7.1-7.2 (m, 1H), 7.34 (s, 1H), 7.5-7.6 (m, 1H), 7.8-8.2 (m, 3H), 11.2 (br, 1H), 11.4 (br, 1H), 12.5 (br, 1H) | 383.7 | 3.3 min |
| 159 | | | (2Z,5Z)-N-[5-({2-[(2,4-dimethylphenyl)azamethylene]-4-oxo-1,3-thiazolidin-5-ylidene}methyl)-1,3-thiazol-2-yl]acetamide | 2.1-2.3 (m, 6H), 2.31 (s, 3H), 6.8 (br, 1H), 7.0-7.1 (m, 2H), 7.86 (s, 1H), 7.96 (s, 1H), 12.3 (br, 1H), 12.5 (s, 1H) | 372.8 | 3.4 min |
| 160 | | | (2Z,5Z)-N-[5-({2-[(4-hydroxy-2-methylphenyl)azamethylene]-4-oxo-1,3-thiazolidin-5-ylidene}methyl)-1,3-thiazol-2-yl]acetamide | 2.1-2.2 (m, 6H), 6.6-6.9 (m, 3H), 7.83 (s, 1H), 7.94 (s, 1H), 9.5 (br, 1H), 12.5 (br, 1H) | 374.7 | 3.0 min |
| 161 | | | (2Z,5Z)-N-[5-({2-[(2,4-dimethoxyphenyl)azamethylene]-4-oxo-1,3-thiazolidin-5-ylidene}methyl)-1,3-thiazol-2-yl]acetamide | 2.1-2.2 (m, 3H), 3.7-3.9 (m, 6H), 6.6-6.7 (m, 2H), 7.8-8.0 (m, 3H), 12.5 (s, 1H) | 404.7 | 3.2 min |

TABLE 26-continued

| Compound No. | R₁ₐ | R₃ | Name | 1H-NMR | Dtctd Mass | HPLC |
|---|---|---|---|---|---|---|
| 162 | (pivaloyl group) | 3-(hydroxymethyl)-2-methylphenyl | (2Z,5Z)-N-{5-[(2-{[3-(hydroxymethyl)-2-methylphenyl]azamethylene}-4-oxo-1,3-thiazolidin-5-ylidene)methyl]-1,3-thiazol-2-yl}acetamide | 2.0-2.2 (m, 6H), 4.53 (d, 2H, J = 5.6 Hz), 5.1-5.2 (m, 1H), 6.8 (br, 1H), 7.2-7.3 (m, 2H), 7.86 (s, 1H), 7.98 (s, 1H), 12.4 (br, 1H), 12.5 (s, 1H) | 388.7 | 3.1 min |
| 163 | (pivaloyl group) | 4-methoxy-2-methylphenyl | (2Z,5Z)-N-[5-({2-[(4-methoxy-2-methylphenyl]azamethylene]-4-oxo-1,3-thiazolidin-5-ylidene}methyl)-1,3-thiazol-2-yl]acetamide | 2.1-2.2 (m, 6H), 3.7-3.8 (m, 3H), 6.8-7.1 (m, 3H), 7.85 (s, 1H), 7.96 (s, 1H), 12.5 (s, 1H) | 388.8 | 3.3 min |
| 164 | (pivaloyl group) | 2-(isopropyl)phenyl | (2Z,5Z)-N-{5-[(2-{[2-(isopropyl)phenyl]azamethylene}-4-oxo-1,3-thiazolidin-5-ylidene)methyl-1,3-thiazol-2-yl]acetamide | 1.15 (d, 6H, J = 6.8 Hz), 2.14 (s, 3H), 3.0 (m, 1H), 6.9 (br, 1H), 7.2-7.4 (m, 3H), 7.87 (s, 1H), 7.97 (s, 1H), 12.4 (br, 1H), 12.5 (s, 1H) | 386.8 | 3.4 min |
| 165 | (pivaloyl group) | 2,3-dimethylphenyl | (2Z,5Z)-N-[5-({2-[(2,3-dimethylphenyl)azamethylene]-4-oxo-1,3-thiazolidin-5-ylidene}methyl)-1,3-thiazol-2-yl]acetamide | 2.06 (s, 3H), 2.14 (s, 3H), 2.28 (s, 3H), 6.8 (br, 1H), 7.0-7.2 (m, 2H), 7.86 (s, 1H), 7.96 (s, 1H), 12.3 (br, 1H), 12.5 (s, 1H) | 372.8 | 3.4 min |
| 166 | (pivaloyl group) | indan-4-yl | (5Z)-N-{5-[(2-(indan-4-ylazamethylene)-4-oxo-1,3-thiazolidin-5-ylidene]methyl}-1,3-thiazol-2-yl)acetamide | 2.06 (s, 3H), 2.14 (s, 3H), 2.28 (s, 3H), 6.8 (br, 1H), 7.0-7.2 (m, 2H), 7.86 (s, 1H), 7.96 (s, 1H), 12.3 (br, 1H), 12.5 (s, 1H) | 384.8 | 3.4 min |

TABLE 27

| Compound No. | R₁ₐ | R₃ | Name | 1H-NMR | Dtctd Mass | HPLC |
|---|---|---|---|---|---|---|
| 167 | (pivaloyl group) | 3-methoxy-2-methylphenyl | (2Z,5Z)-N-[5-({2-[(3-methoxy-2-methylphenyl)azamethylene]-4-oxo-1,3-thiazolidin-5-ylidene}methyl)-1,3-thiazol-2-yl]acetamide | 1.98 (s, 3H), 2.14 (s, 3H), 3.83 (s, 3H), 6.6 (br, 1H), 6.8-6.9 (m, 1H), 7.2-7.3 (m, 1H), 7.86 (s, 1H), 7.96 (s, 1H), 12.4 (br, 1H), 12.51 (s, 1H) | 388.8 | 3.3 min |
| 168 | (pivaloyl group) | 2H-benzo[3,4-d]1,3-dioxolan-5-yl | (5Z)-N-(5-{[2-(2H-benzo[3,4-d]1,3-dioxolan-5-ylazamethylene)-4-oxo-1,3-thiazolidin-5-ylidene]methyl}-1,3-thiazol-2-yl)acetamide | 2.1-2.2 (m, 3H), 6.0-6.1 (m, 2H), 6.5-6.7 (m, 1H), 6.9-7.1 (m, 2H), 7.8-8.0 (m, 2H), 12.5 (br, 1H) | 388.7 | 3.2 min |
| 169 | H | indol-6-yl | (5Z)-5-[(2-amino(1,3-thiazol-5-yl))methylene]-2-(indol-6-ylazamethylene)-1,3-thiazolidin-4-one | 6.3-6.4 (m, 1H), 7.1-7.4 (m, 2H), 7.5-7.6 (m, 2H), 7.6-8.2 (m, 4H), 11.1-11.3 (m, 2H) | 342.1 | 3.1 min |
| 170 | (pivaloyl group) | 3-hydroxy-2-methylphenyl | (2Z,5Z)-N-[5-({2-[(3-hydroxy-2-methylphenyl)azamethylene]-4-oxo-1,3-thiazolidin-5-ylidene}methyl)-1,3-thiazol-2-yl]acetamide | 1.9-2.0 (m, 3H), 2.1-2.2 (m, 3H), 3.83 (s, 1H), 6.3-6.6 (m, 1H), 6.6-6.9 (m, 1H), 7.0-7.3 (m, 1H), 7.86 (s, 1H), 7.96 (s, 1H), 9.5 (br, 1H), 12.50 (s, 1H) | 374.7 | 3.1 min |

TABLE 27-continued

| Compound No. | R$_{1a}$ | R$_3$ | Name | 1H-NMR | Dtctd Mass | HPLC |
|---|---|---|---|---|---|---|
| 171 | H | (4-hydroxy-2-methylphenyl) | (2Z,5Z)-5-[(2-amino(1,3-thiazol-5-yl))methylene]-2-[(4-hydroxy-2-methylphenyl)azamethylene]-1,3-thiazolidin-4-one | 2.1-2.2 (m, 3H), 6.5-6.7 (m, 2H), 6.9 (br, 1H), 7.52 (s, 1H), 7.65 (s, 1H), 7.7-7.9 (n, 2H), 9.4 (m, 1H) | 332.7 | 2.8 min |
| 172 | H | (2,4-dimethoxyphenyl) | (2Z,5Z)-5-[(2-amino(1,3-thiazol-5-yl))methylene]-2-[(2,4-dimethyoxyphenyl)azamethylene]-1,3-thiazolidin-4-one | 3.7-3.9 (m, 6H), 6.4-6.7 (m, 2H), 7.53 (s, 1H), 7.66 (s, 1H), 7.7-8.3 (m, 3H) | 362.7 | 3.0 min |
| 173 | H | (indan-4-yl) | (5Z)-5-[(2-amino(1,3-thiazol-5-yl))methylene]-2-(indan-4-ylazamethylene)-1,3-thiazolidin-4-one | 2.0-2.1 (m, 2H), 2.6-2.8 (m, 2H), 2.9-3.0 (m, 2H), 6.7-7.2 (m, 2H), 7.54 (s, 1H), 7.69 (s, 1H), 7.7-7.8 (m, 1H), 8.30 (s, 2H), 9.61 (s, 1H) | 343.1 | 3.3 min |
| 174 | H | (3-methoxy-2-methylphenyl) | (2Z,5Z)-5-[(2-amino(1,3-thiazol-5-yl))methylene]-2-[(3-methoxy-2-methylphenyl)azamethylene]-1,3-thiazolidin-4-one | 1.96 (s, 3H), 3.81 (s, 3H), 6.5-7.2 (m, 2H), 7.5-8.0 (m, 3H), 8.32 (s, 2H), 9.61 (s, 1H) | 346.7 | 3.2 min |
| 175 | H | (4-methoxy-2-methylphenyl) | (2Z,5Z)-5-[(2-amino(1,3-thiazol-5-yl))methylene]-4-[(4-methoxy-2-methylphenyl)azamethylene]-1,3-thiazolidin-4-one | 2.1-2.2 (m, 3H), 3.76 (s, 3H), 6.8-7.0 (m, 3H), 7.53 (s, 1H), 7.67 (s, 1H), 7.78 (s, 2H) | 347.1 | 3.1 min |
| 176 | pivaloyl | (2-methyl-4-nitrophenyl) | (2Z,5Z)-N-[5-({2-[(2-methyl-4-nitrophenyl)azamethylene]-4-oxo-1,3-thiazolidin-5-ylidene}methyl)-1,3-thiazol-2-yl]acetamide | 2.14 (s, 3H), 2.25 (s, 3H), 7.1-7.2 (m, 1H), 7.93 (s, 1H), 8.00 (s, 1H), 8.0-8.1 (m, 1H), 8.21 (s, 1H), 12.55 (s, 1H), 12.6 (br, 1H) | 403.7 | 3.4 min |
| 177 | pivaloyl | (indol-7-yl) | (5Z)-N-(5-{[2-(indol-7-ylazamethylene)-4-oxo-1,3-thiazolidin-5-ylidene]methyl}-1,3-thiazol-2-yl)acetamide | 2.1-2.2 (m, 3H), 6.4-6.5 (m, 1H), 6.71 (d, 1H, J = 7.2 Hz), 6.99 (t, 1H, J = 7.6 Hz), 7.2-7.3 (m, 1H), 7.38 (d, 1H, J = 8.0 Hz), 7.79 (s, 1H), 7.90 (s, 1H), 11.0 (br, 1H) | 383.7 | 3.3 min |
| 178 | pivaloyl | (benzimidazol-5-yl) | (5Z)-N-(5-{[2-(benzimidazol-5-ylazamethylene)-4-oxo-1,3-thiazolidin-5-ylidene]methyl}-1,3-thiazol-2-yl)acetamide | 2.1-2.2 (m, 3H), 6.9-7.7 (m, 3H), 7.8-8.0 (m, 2H), 8.2-8.3 (m, 2H), 12.5 (m, 2H) | 384.7 | 2.7 min |
| 179 | pivaloyl | (benzotriazol-5-yl) | (5Z)-N-(5-{[2-(benzotriazol-5-ylazamethylene)-4-oxo-1,3-thiazolidin-5-ylidene]methyl}-1,3-thiazol-2-yl)acetamide | 2.1-2.2 (m, 3H), 7.0-7.5 (m, 1H), 7.89 (s, 1H), 7.97 (s, 1H), 8.0-8.1 (m, 1H), 8.5-8.6 (m, 1H), 12.5-12.6 (m, 1H) | 385.7 | 3.0 min |

TABLE 28

| Compound No. | R$_{1a}$ | R$_3$ | Name | 1H-NMR | Dtctd Mass | HPLC |
|---|---|---|---|---|---|---|
| 180 | ketone (tBu-C(=O)-) | 2-hydroxyphenyl | (2Z,5Z)-N-[5-({2-[(2-hydroxyphenyl)azamethylene]-4-oxo-1,3-thiazolidin-5-ylidene}methyl)-1,3-thiazol-2-yl]acetamide | 2.1-2.2 (m, 3H), 6.8-6.9 (m, 1H), 6.9-7.0 (m, 1H) 7.0-7.2 (m, 1H), 7.85 (s, 1H), 7.9-8.0 (m, 1H), 12.5 (br, 1H) | 360.8 | 3.1 min |
| 181 | H | 2-chlorophenyl | (2Z,5Z)-5-[(2-amino(1,3-thiazol-5-yl))methylene]-2-[2-(2-chlorophenyl)-1-azaethylidene]-1,3-thiazolidin-4-one | 4.7-4.8 (m, 2H), 7.3-7.5 (m, 4H), 7.53 (s, 1H), 7.66 (s, 1H), 7.85 (s, 1H), 9.8 (br, 1H) | 350.7 | 3.1 min |
| 182 | ketone (tBu-C(=O)-) | 2-bromophenyl | (2Z,5Z)-N-[5-({2-[(2-bromophenyl)azamethylene]-4-oxo-1,3-thiazolidin-5-ylidene}methyl)-1,3-thiazol-2-yl]acetamide | 2.14 (s, 3H), 7.1-7.2 (m, 2H), 7.3-7.4 (m, 1H), 7.6-7.7 (m, 1H), 7.88 (s, 1H), 7.97 (s, 1H), 12.5-12.7 (m, 2H) | 424.5 | 3.3 min |
| 183 | H | 2,3-dimethylphenyl | (2Z,5Z)-5-[(2-amino(1,3-thiazol-5-yl))methylene]-2-[(2,3-dimethylphenyl)azamethylene]-1,3-thiazolidin-4-one | 2.09 (s, 3H), 2.28 (s, 3H), 6.8-6.9 (m, 1H), 7.0-7.2 (m, 2H), 7.54 (s, 1H), 7.67 (s, 1H), 7.79 (s, 2H), 12.1 (br, 1H) | 331.2 | 3.2 min |
| 184 | H | 2,4-dimethylphenyl | (2Z,5Z)-5-[(2-amino(1,3-thiazol-5-yl))methylene]-2-[(2,4-dimethylphenyl)azamethylene]-1,3-thiazolidin-4-one | 2.04 (s, 3H), 2.27 (s, 3H), 6.75 (d, 1H, J = 7.6 Hz), 6.99 (d, 1H, J = 7.6 Hz), 7.09 (t, 1H, J = 7.6 Hz), 7.51 (s, 1H), 7.65 (s, 1H), 7.75 (s, 2H) | 331.1 | 3.2 min |
| 185 | ketone (tBu-C(=O)-) | 4-[2-(dimethylamino)ethoxy]-2-methylphenyl | (2Z,5Z)-N-(5-{[2-({4-[2-(dimethylamino)ethoxy]-2-methylphenyl}azamethylene)-4-oxo-1,3-thiazolidin-5-ylidene]methyl}-1,3-thiazol-2-yl)acetamide | 2.0-2.3 (m, 12H), 2.5-2.6 (m, 2H), 4.0-4.1 (m, 2H), 6.7-6.9 (m, 3H), 7.70 (s, 1H), 7.86 (s, 1H) | 445.8 | 2.6 min |
| 186 | ketone (tBu-C(=O)-) | 2-methyl-4-(2-(1-pyrrolidinyl)ethoxy)phenyl | (2Z,5Z)-N-{5-[(2-{[2-methyl-4-(2-(1-pyrrolidinyl)ethoxy)phenyl]azamethylene}-4-oxo-1,3-thiazolidin-5-ylidene)methyl]-1,3-thiazol-2-yl}acetamide | 1.7-1.8 (m, 4H), 2.1-2.2 (m, 6H), 2.5-2.6 (m, 4H), 2.8-2.9 (m, 2H), 4.0-4.1 (m, 2H), 6.8-7.0 (m, 3H), 7.80 (s, 1H), 7.93 (s, 1H), 12.3 (br, 1H) | 472.2 | 2.7 min |

TABLE 28-continued

| Compound No. | R$_{1a}$ | R$_3$ | Name | 1H-NMR | Dtctd Mass | HPLC |
|---|---|---|---|---|---|---|
| 187 | (pivaloyl) | 4-[3-(dimethylamino)propoxy]-2-methylphenyl | (2Z,5Z)-N-(5-{[2-({4-[3-(dimethylamino)propoxy]-2-methylphenyl}azamethylene)-4-oxo-1,3-thiazolidin-5-ylidene]methyl}-1,3-thiazol-2-yl)acetamide | 1.8-1.9 (m, 2H), 2.1-2.2 (m, 12H), 2.4-2.5 (m, 2H), 4.0-4.1 (m, 2H), 6.8-6.9 (m, 3H), 7.80 (s, 1H), 7.92 (s, 1H), 12.4 (br, 1H) | 460.3 | 2.7 min |
| 188 | (pivaloyl) | 4-(2-methoxymethoxy)-2-methylphenyl | (2Z,5Z)-N-{5-[(2-{[4-(2-methoxymethoxy)-2-methylphenyl]azamethylene}-4-oxo-1,3-thiazolidin-5-ylidene)methyl]-1,3-thiazol-2-yl}acetamide | 2.1-2.2 (m, 6H), 3.32 (s, 3H), 3.6-3.7 (m, 1H), 4.0-4.1 (m, 1H), 6.8-7.0 (m, 3H), 7.84 (s, 1H), 7.95 (s, 1H), 12.5 (br, 1H) | 433.1 | 3.2 min |
| 189 | (pivaloyl) | 4-acetamido-3-methylphenyl | (2Z,5Z)-N-{4-[(5-{[2-(acetylamino)(1,3-thiazol-5-yl)]methylene}-4-oxo(1,3-thiazolidin-2-ylidene))azamethyl]-3-methylphenyl}acetamide | 2.0-2.2 (m, 9H), 6.8-6.9 (m, 1H), 7.4-7.5 (m, 2H), 7.80 (s, 1H), 7.92 (s, 1H), 9.9-10.0 (m, 1H), 12.2 (br, 1H) | 415.7 | 3.0 min |
| 190 | (pivaloyl) | 4-(2-hydroxyethoxy)-2-methylphenyl | (2Z,5Z)-N-{5-[(2-{[4-(2-hydroxyethoxy)-2-methylphenyl]azamethylene}-4-oxo-1,3-thiazolidin-5-ylidene)methyl]-1,3-thiazol-2-yl}acetamide | 2.1-2.2 (m, 6H), 3.7-3.8 (m, 2H), 4.0-4.1 (m, 2H), 4.8-4.9 (m, 1H), 6.8-6.9 (m, 3H), 7.85 (s, 1H), 8.00 (s, 1H), 12.5 (br, 1H) | 418.7 | 3.0 min |
| 191 | (pivaloyl) | 4-(3-hydroxypropoxy)-2-methylphenyl | (2Z,5Z)-N-{5-[(2-{[4-(3-hydroxypropoxy)-2-methylphenyl]azamethylene}-4-oxo-1,3-thiazolidin-5-ylidene)methyl]-1,3-thiazol-2-yl}acetamide | 1.8-1.9 (m, 2H), 2.1-2.2 (m, 6H), 2.5-2.6 (m, 2H), 4.0-4.1 (m, 2H), 4.5-4.6 (m, 1H), 6.8-6.9 (m, 3H), 7.85 (s, 1H), 7.96 (s, 1H), 12.5 (br, 1H) | 432.8 | 3.1 min |
| 192 | (pivaloyl) | 4-hydroxy-2,3-dimethylphenyl | (2Z,5Z)-N-[5-({2-[(4-hydroxy-2,3-dimethylphenyl)azamethylene]-4-oxo-1,3-thiazolidin-5-ylidene}methyl)-1,3-thiazol-2-yl]acetamide | 2.0-2.2 (m, 9H), 6.7-6.8 (m, 2H), 7.82 (s, 1H), 7.94 (s, 1H), 12.5 (br, 1H) | 388.8 | 3.1 min |

TABLE 29

| Compound No. | $R_{1a}$ | $R_3$ | Name | 1H-NMR | Dtctd Mass | HPLC |
|---|---|---|---|---|---|---|
| 193 | pivaloyl | 2-chloro-4-hydroxyphenyl | (2Z,5Z)-N-[5-{(2-[(2-chloro-4-hydroxyphenyl)azamethylene]-4-oxo-1,3-thiazolidin-5-ylidene}methyl)-1,3-thiazol-2-yl]acetamide | 2.1-2.2 (m, 3H), 6.7-7.0 (m, 3H), 7.86 (s, 1H), 7.96 (s, 1H), 9.8 (br, 1H), 12.5 (br, 1H) | 394.7 | 3.1 min |
| 194 | pivaloyl | 2-methyl-4-(2-morpholinoethoxy)phenyl | (2Z,5Z)-N-{5-[(2-{[2-methyl-4-(2-morpholinoethoxy)phenyl]azamethylene}-4-oxo-1,3-thiazolidin-5-ylidene)methyl]-1,3-thiazol-2-yl}acetamide | 2.1-2.2 (m, 6H), 2.7-2.8 (m, 2H), 3.5-3.6 (m, 4H), 4.0-4.1 (m, 2H), 6.8-7.0 (m, 3H), 7.85 (s, 1H), 7.95 (s, 1H), 12.1 (br, 1H), 12.6 (br, 1H) | 488.2 | 2.7 min |
| 195 | pivaloyl | 4-hydroxy-2-(trifluoromethyl)phenyl | (2Z,5Z)-N-{5-[(2-{[4-hydroxy-2-(trifluoromethyl)phenyl]azamethylene}-4-oxo-1,3-thiazolidin-5-ylidene)methyl]-1,3-thiazol-2-yl}acetamide | 2.1-2.2 (m, 3H), 7.0-7.1 (m, 3H), 7.87 (s, 1H), 7.97 (s, 1H), 10.0 (br, 1H), 12.5 (br, 1H) | 428.8 | 3.6 min |
| 196 | pivaloyl | 3-fluoro-4-hydroxyphenyl | (2Z,5Z)-N-[5-({2-[(3-fluoro-4-hydroxyphenyl)azamethylene]-4-oxo-1,3-thiazolidin-5-ylidene}methyl)-1,3-thiazol-2-yl]acetamide | 2.1-2.2 (m, 3H), 6.7-7.0 (m, 1H), 7.0-7.1 (m, 1H), 7.2-7.3 (m, 0.5H), 7.7-7.8 (m, 0.5H), 7.8-8.0 (m, 2H), 9.8-10.0 (m, 1H), 12.5 (br, 1H) | 378.7 | 3.1 min |
| 197 | pivaloyl | 2-methyl-4-(methylamino)phenyl | (2Z,5Z)-N-{5-[(2-{[2-methyl-4-(methylamino)phenyl]azamethylene}-4-oxo-1,3-thiazolidin-5-ylidene)methyl]-1,3-thiazol-2-yl}acetamide | 2.1-2.2 (m, 6H), 2.6-2.7 (m, 3H), 5.8-5.9 (m, 0.5H), 6.4-6.5 (m, 2H), 6.9-7.0 (m, 0.5H), 7.81 (s, 1H), 7.93 (s, 1H), 12.5 (br, 1H) | 388.2 | 3.0 min |
| 198 | pivaloyl | 4-(dimethylamino)-2-methylphenyl | (2Z,5Z)-N-{5-[(2-{[4-(dimethylamino)-2-methylphenyl]azamethylene}-4-oxo-1,3-thiazolidin-5-ylidene)methyl]-1,3-thiazol-2-yl}acetamide | 2.1-2.2 (m, 6H), 2.9-3.0 (m, 6H), 6.6-6.7 (m, 2H), 6.9-7.0 (m, 1H), 7.79 (s, 1H), 7.92 (s, 1H), 12.2 (br, 1H) | 402.2 | 3.2 min |

CDC7 Protein Kinase Inhibitory Action of Thiazolidinone Derivatives

CDC7 protein kinase inhibitory action of the thiazolidinone derivatives shown Table 2 to 21 and 26 to 29 were evaluated according to the following procedure.

As a substrate for evaluating the enzymatic activity, mouse MCM2-4(his)-6-7(his) conjugated protein was synthesized. Firstly, the following genes were cloned into the pAcUW31 vector (Pharmingen).

Mouse MCM2 (Genbank/EMBL No. D86725);
N-His-mouse MCM4 (Genbank/EMBL No. D26089, a His6 tag was added to the N-terminus);
Mouse MCM6 (Genbank/EMBL No. D86726), and
N-His-mouse MCM7 (Genbank/EMBL No. D26091, a His6 tag was added to the N-terminus).

The Mouse MCM2 gene and the N-His-mouse MCM7 gene were inserted into the BamHI site and the EcoRI site of the pAcUW31 vector (Mom2-7 Vector), respectively. The mouse MCM6 gene and the N-His-mouse MCM4 gene were inserted into the BamHI site and the EcoRI site of the pAcUW31 vector (MGm4-6 Vector), respectively. Then, in order to produce recombinant mouse MCM2-7 (his) and mouse MCM4 (his)-6 baculovirus, BaculoGold AcNPV Baculovirus DNA (BD/Pharmingen) and the Mcm2-7 or Mcm4-6 vector were cotransfected into Sf9 insect cells. The Mcm2-7 and Mom4-6 virus thus obtained were coinfected into Hi5 insect cells. Thereby, the mouse MCM2-4(his)-6-7 (his) conjugated protein was obtained. Purified mouse MCM2-4(his)-6-7(his) conjugated protein (0.5 µg) was used as a substrate.

The substrate (mouse MCM2-4(his)-6-7(his) conjugated protein) (0.5 µg) and a kinase enzyme (human Gdc7/human ASK conjugated protein, CARNA BIOSCIENCES) (0.1 µg) were mixed in a microtube. A kinase reaction buffer containing 0.1 µL of γ-$^{32}$P ATP (Perkin Elmer) was added as a tracer into the same microtube. The composition of the kinase buffer is as follows.

40 mM HEPES-KOH buffer, pH 7.6;
0.5 mM EDTA;
0.5 mM EGTA;
1 mM β-glycerophosphate;
1 mM NaF;
2 mM Dithiothreitol; and
0.1 mM ATP Furthermore, 0.5 µL each of the test compounds (thiazolidinone derivatives at 10 µM, 100 µM, and 1000 µM, respectively) was added and reacted at 30° C. for 45 minutes. After the reaction, the substrate was separated by the SDS-PAGE method, and proteins were stained by the silver staining method (2D-silver staining reagent II "Daiichi", Daiichi Pure Chemicals Co., Ltd.).

The radioactivity of $^{32}$P-labeled MCM2 protein was detected by autoradiography, and the radioactivity of the band of MCM2 protein was measured by the liquid scintillation counter (LSC-6100, ALOKA). For the Cdc7-ASK kinase activity, the radioactivity at the time of addition of each of the test compounds was calculated in percent, when the radioactivity at the time of addition of DMSO (0.5 µL) instead of the test compound (0.5 µL) added immediately before the above-mentioned reaction was set to be 100%. Based on the obtained results, the IC 50 value of each test compound was calculated. IC50 for Cdc7-ASK kinase of the major thiazolidinone derivatives shown in Tables 2 to 21 were ranging from 15 nM to 100 nM.

Cell Proliferation Inhibitory Activity of Thiazolidinone Derivatives

Cell proliferation inhibitory activity of the thiazolidinone derivatives shown in Tables 2 to 21 and 26 to 29 were evaluated according to the following procedure.

HeLa cells (ATCC) were cultured in a medium (DMEM-10% FCS-Penicillin/Streptomycin) on 10-cm dishes. The medium was removed from the HeLa cells (ATCC) in healthy growth conditions (70 to 90% confluent), the cells were detached by treating with 2 ml of trypsin (TrypL Express, GIBCO), and then the cells were collected using the same medium.

NHDF cells (Cryo NHDF-NeoCC-2509, SANKO ZYUNYAKU) were cultured in the medium (Bullet Kit FGM2, CLCC-3132) in 10-cm dishes. The medium was removed from the NHDF cells in healthy growth conditions (70 to 90% confluent), the cells were washed with 5 mL of HEPES-buffered saline attached to the reagent kit for subculture (CLCC-5034, SANKO ZYUNYAKU). After removing HEPES-buffered saline, the whole dish was treated with 3 mL of Trypsin-EDTA attached to the reagent kit. After detaching cells by tapping the dish, the cells were collected by adding 3 mL of trypsin neutralization solution contained in the kit.

After the collected cells were suspended in the medium at a concentration of $5 \times 10^4$ cells/mL, 100 µL, each of the cells were seeded on 96-well plates (FALCON, 3530) at a concentration of $5 \times 10^3$ cells/mL per well. Each medium alone without cells was added to the blank wells. The wells were incubated in a 5% $CO_2$ incubator. The culture media used are as follows.

HeLa cells: DMEM-10% FCS-Penicillin/Streptomycin,
NHDF cells: Bullet Kit FGM2, CLCC-3132.

The following day after the start of culturing, the medium was replaced with that including candidate compounds. At the beginning, the candidate compounds were diluted with DMSO, and a 10-step dilution series from 0 µM to 12.5 mM was prepared. 249 µL of the medium was added to 1.5-ml tubes. Then, 1 µL of the compound diluted with DMSO was added thereto at each concentration, and this was mixed. By this procedure, the ratio of DMSO included becomes 1/250. More specifically, in case of the following dilution series, the final concentrations of candidate compounds are as follows.

| Dilution series | Final concentration of candidate compound |
|---|---|
| DMSO only (0 µM) | 0 |
| 0.5 µM | 0.002 µM |
| 2.5 µM | 0.01 µM |
| 12.5 µM | 0.05 µM |
| 25 µM | 0.1 µM |
| 125 µM | 0.5 µM |
| 250 µM | 1.0 µM |
| 0.5 mM | 2.0 µM |
| 1.25 mM | 5 µM |
| 2.5 mM | 10 µM |
| 12.5 mM | 50 µM |

After removing the medium in wells, each candidate compound was added in duplicate to each well at a volume of 100 µL per one concentration. 100 µL of medium only was added to the blank wells. After addition of candidate compounds, the dishes were lid-closed and returned to the $CO_2$ incubator.

On the next day or the day after the next day (24 to 48 hours later), 10 µL of Cell Proliferation Reagent WST-1 (ROCHE) was added to each well. Cell Proliferation Reagent WST-1 was dissolved and used for measurement after returned to room temperature just before use. Dissolved Cell Proliferation Reagent WST-1 was dispensed using Multipette plus (EPPENDORF) and 1.0 mL of combitips plus (EPPENDORF). WST-1 is reduced by reducing action of surviving cells, and thus forms a pigment. The formed pigment can be assayed by measuring the absorbance at 450 nm. After incubation for an hour in a $CO_2$ incubator, the absorbance at 450 nm was measured using a microplate reader. The values were evaluated by subtracting the blank value, and plotted by curve-fitting using the Prism software, and IC50 was calculated.

The results of assessing the cell proliferation-inhibiting effect of the compounds of the present invention are shown in FIG. 1. The results for compounds 119, 137 and 139 are shown.

As is clear from these results, the thiazolidinone derivatives of the present invention inhibit cell proliferation in a concentration-dependent manner. For example, compounds 119, 137 and 139 have a strong inhibitory effect.

Industrial Applicability

Novel thiazolidinone derivatives provided by the present invention are useful as CDC7 protein kinase inhibitors. The CDC7 protein kinase is a molecule that plays an important role in DNA replication. Therefore, compounds that inhibit the action of CDC7 protein kinase can be used as agents for suppressing cell proliferation.

The invention claimed is:
1. A compound represented by the following formula (I), a geometric isomer or a tautomer thereof, or a salt thereof:

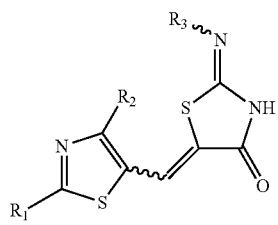

wherein
$R_1$ is selected from the group consisting of a hydrogen atom, a linear or branched lower alkyl group, a halogen, a hydroxyl group, an amino group that may have a substituent, and a nonaromatic heterocyclic group that may have a substituent;
$R_2$ is a hydrogen atom, or a linear or branched lower alkyl group;
$R_3$ is selected from the group consisting of a linear or branched lower alkyl group, a cycloalkyl group that may have a substituent, an aryl group that may have a substituent, an arylalkyl group that may have a substituent, a nonaromatic heterocyclic group that may have a substituent, a heteroaryl group that may have a substituent, and a fused ring group that may have a substituent; and
a wavy line denotes trans, cis or a mixture thereof.

2. The compound, a geometric isomer or a tautomer thereof, or a salt thereof according to claim 1, wherein $R_1$ is a group independently selected from A below:
A:
a hydrogen atom;
a halogen;
a hydroxyl group;
a linear or branched lower alkyl group;
a group represented by —$NR_{11}R_{12}$ (wherein $R_{11}$ and $R_{12}$ are each independently selected from a hydrogen atom, a linear or branched lower alkyl group that may optionally be substituted by one to three halogen atoms or a cycloalkyl group, or a cycloalkyl group; or $R_{11}$ and $R_{12}$, together with the nitrogen atom to which they are attached, form a nonaromatic heterocyclic ring);
a group represented by —$N(R_{13})[(CH_2)_x—NR_{14}R_{15}]$ (wherein x is 2 to 4; $R_{13}$ is a hydrogen atom or a lower alkyl group; $R_{14}$ and $R_{15}$ are each a hydrogen atom or a lower alkyl group, or $R_{14}$ and $R_{15}$, together with the nitrogen atom to which they are attached, form a nonaromatic heterocyclic ring);
a group represented by —NHCO—$(CH_2)_y$—$NR_{16}R_{17}$ (wherein y is 0 to 3; $R_{16}$ and $R_{17}$ are each a hydrogen atom or a lower alkyl group that may optionally be substituted by an amino group substituted by one or two lower alkyl groups, or $R_{16}$ and $R_{17}$, together with the nitrogen atom to which they are attached, form a nonaromatic heterocyclic ring); and
a group represented by —NHCO—$(CH_2)_z$—$R_{18}$ (wherein z is 0 to 3; $R_{18}$ is a lower alkyl group that may optionally be substituted by one to three halogen atoms, a lower alkoxyl group, a lower alkoxycarbonyl group, a carboxyl group, a cycloalkyl group, a nonaromatic heterocyclic group that may optionally be substituted by a lower alkyl group, or an aminocarbonyl group that may be substituted by one or two lower alkyl groups).

3. The compound, a geometric isomer or a tautomer thereof, or a salt thereof according to claim 1 or 2, wherein $R_3$ is an aryl group or a heteroaryl group that may optionally be substituted by one to three groups independently selected from B below:
B:
a linear or branched lower alkyl group that may optionally be substituted by a group selected from the group consisting of one to three halogen atoms, a hydroxyl group, an amino group substituted by one or two lower alkyl groups, and a nonaromatic heterocyclic group;
a lower alkoxy group;
a hydroxyl group;
a halogen;
a nitro group;
an amino group that may optionally be substituted by one or two lower alkyl groups;
a lower alkylcarbonylamino group;
a group represented by a formula: —$(CH_2)_k COOH$ (wherein k is 0 to 2);
a group represented by a formula: —O—$R_{31}$—$R_{32}$ (wherein $R_{31}$ is a single bond, a lower alkylene group or a cycloalkylene group; $R_{32}$ is a group selected from a hydroxyl group, a carboxyl group, a lower alkoxyl group, a lower alkoxycarbonyl group, an amino group substituted by two lower alkyl groups or by one a lower alkyl group and one lower alkoxycarbonyl group, and a nonaromatic heterocyclic group that may optionally be substituted by a lower alkyl group; and
a group represented by a formula: —$CON(R_{33})[(CH_2)_m$—$R_{34}]$ (wherein m is 0 to 2; $R_{33}$ is a hydrogen atom or a lower alkyl group; $R_{34}$ is an amino group substituted by one or two lower alkyl groups).

4. The compound, a geometric isomer or a tautomer thereof, or a salt thereof according to claim 3, wherein said aryl group or heteroaryl group is a phenyl group, a naphthyl group, an indolyl group, an indazolyl group, a quinolyl group, a benzimidazolyl group or a benzotriazolyl group.

5. The compound, a geometric isomer or a tautomer thereof, or a salt thereof according to claim 1 or 2, wherein said $R_3$ is a benzyl group having a substituent, and wherein the benzene ring of said benzyl group is substituted with halogen, a lower alkyl group that may optionally be substituted by one to three halogen atoms, or a lower alkoxy group, or wherein the methylene group of said benzyl group is substituted by one or two lower alkyl groups.

6. The compound, a geometric isomer or a tautomer thereof, or a salt thereof according to claim 1 or 2, wherein said $R_3$ is an indanyl group or a 1,3-benzodioxolyl group.

7. A pharmaceutical composition comprising a compound, a geometric isomer or a tautomer thereof, or a salt thereof according to any one of claim 1 or 2, and a pharmaceutically acceptable carrier.

8. A process for producing the compound according to claim 1, by reacting a compound represented by the following formula (II) with a compound represented by the following formula (III) in which an imino group has been modified in advance:
Formula (II):
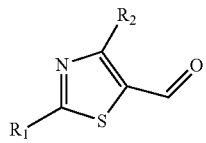
Formula (III):
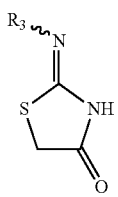
wherein $R_1$, $R_2$ and $R_3$ are the same as $R_1$, $R_2$ and $R_3$ in claim 1.
* * * * *